（12）United States Patent
Soula et al.

US010881716B2

(10) Patent No.: US 10,881,716 B2
(45) Date of Patent: *Jan. 5, 2021

(54) RAPID-ACTING INSULIN FORMULATION COMPRISING A SUBSTITUTED ANIONIC COMPOUND

(71) Applicant: ADOCIA, Lyons (FR)

(72) Inventors: Gérard Soula, Meyzieu (FR); Bertrand Alluis, Genas (FR)

(73) Assignee: Adocia, Lyons (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/848,640

(22) Filed: Apr. 14, 2020

(65) Prior Publication Data

US 2020/0237877 A1 Jul. 30, 2020

Related U.S. Application Data

(63) Continuation of application No. 16/687,339, filed on Nov. 18, 2019, now Pat. No. 10,646,551, which is a continuation of application No. 15/609,670, filed on May 31, 2017, now Pat. No. 10,583,175, which is a continuation of application No. 14/079,516, filed on Nov. 13, 2013, now Pat. No. 9,700,599.

(60) Provisional application No. 61/726,349, filed on Nov. 14, 2012, provisional application No. 61/725,775, filed on Nov. 13, 2012.

(30) Foreign Application Priority Data

Nov. 13, 2012 (FR) ..................... 12 60808
Nov. 14, 2012 (FR) ..................... 12 60855

(51) Int. Cl.
| | |
|---|---|
| A61K 38/28 | (2006.01) |
| C07H 3/06 | (2006.01) |
| C08B 37/02 | (2006.01) |
| C07H 15/18 | (2006.01) |
| A61K 47/18 | (2017.01) |
| A61K 47/34 | (2017.01) |
| A61K 47/12 | (2006.01) |
| A61K 47/02 | (2006.01) |
| A61K 47/36 | (2006.01) |
| A61K 9/00 | (2006.01) |
| C07K 5/00 | (2006.01) |
| A61K 47/26 | (2006.01) |

(52) U.S. Cl.
CPC ............ A61K 38/28 (2013.01); A61K 9/0019 (2013.01); A61K 47/02 (2013.01); A61K 47/12 (2013.01); A61K 47/183 (2013.01); A61K 47/26 (2013.01); A61K 47/34 (2013.01); A61K 47/36 (2013.01); C07H 3/06 (2013.01); C07H 15/18 (2013.01); C07K 5/00 (2013.01); C08B 37/0021 (2013.01)

(58) Field of Classification Search
None
See application file for complete search history.

(56) References Cited

U.S. PATENT DOCUMENTS

| | | |
|---|---|---|
| 2,387,201 A | 10/1945 | Weiner |
| 2,847,385 A | 8/1958 | Hiler |
| 4,006,059 A | 2/1977 | Buller |
| 4,011,137 A | 3/1977 | Thompson et al. |
| 4,126,628 A | 11/1978 | Paquet |
| 4,395,399 A | 7/1983 | Ovchinnkov |
| 4,438,029 A | 3/1984 | Erickson et al. |
| 4,472,385 A | 9/1984 | Brange et al. |
| 4,476,118 A | 10/1984 | Brange et al. |
| 4,826,818 A | 5/1989 | Mori et al. |
| 4,839,341 A | 6/1989 | Massey et al. |
| 4,873,322 A | 10/1989 | Fechtgi |
| 4,885,164 A | 12/1989 | Thurow |
| 5,164,366 A | 11/1992 | Balschmidt et al. |
| 5,204,366 A | 4/1993 | Lavanish et al. |
| 5,310,937 A | 5/1994 | Lavanish et al. |
| 5,474,978 A | 12/1995 | Bakaysa et al. |
| 5,716,927 A | 2/1998 | Balschmidt et al. |
| 5,859,217 A | 1/1999 | Tokiwa et al. |
| 5,866,538 A | 2/1999 | Norup et al. |
| 5,929,027 A | 7/1999 | Takama et al. |

(Continued)

FOREIGN PATENT DOCUMENTS

| | | |
|---|---|---|
| CN | 1045586 A | 9/1990 |
| CN | 01111268 A | 11/1995 |

(Continued)

OTHER PUBLICATIONS

U.S. Appl. No. 14/079,516, Rapid-acting insulin formulation comprising a substituted anionic compound, filed Nov. 13, 2013 Issued, U.S. Pat. No. 9,700,599.
U.S. Appl. No. 15/609,670, Rapid-acting insulin formulation comprising a substituted anionic compound, filed May 31, 2017, Issued, U.S. Pat. No. 10,583,175.
U.S. Appl. No. 16/687,339, Rapid-acting insulin formulation comprising a substituted anionic compound, filed Nov. 18, 2019, Issued, U.S. Pat. No. 10,646,551.
U.S. Appl. No. 14/581,239, Rapid-acting insulin formulation comprising an oligosaccharide, filed Dec. 23, 2014, Issued, U.S. Pat. No. 9,492,467.

(Continued)

Primary Examiner — Dale R Miller
(74) Attorney, Agent, or Firm — Goodwin Procter LLP

(57) ABSTRACT

A composition in aqueous solution includes insulin and at least one substituted anionic compound chosen from substituted anionic compounds consisting of a backbone formed from a discrete number u of between 1 and 8 ($1 \le u \le 8$) of identical or different saccharide units, linked via identical or different glycoside bonds, the saccharide units being chosen from the group consisting of hexoses, in cyclic form or in open reduced form, said compound comprising partially substituted carboxyl functional groups, the unsubstituted carboxyl functional groups being salifiable. A pharmaceutical formulation including the composition is also set forth.

7 Claims, 11 Drawing Sheets

(56) References Cited

U.S. PATENT DOCUMENTS

Figure 1:
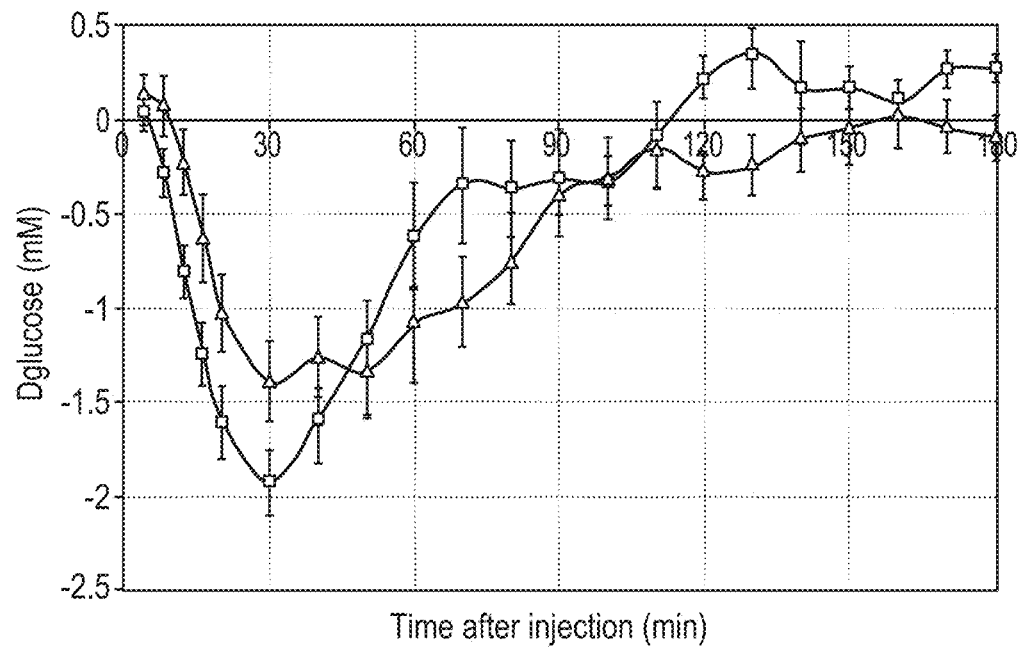

| | | |
|---|---|---|
| 6,991,798 B1 | 1/2006 | Gschneidner et al. |
| 7,279,457 B2 | 10/2007 | Pohl et al. |
| 7,696,162 B2 | 4/2010 | Boderke |
| 7,713,929 B2 | 5/2010 | Steiner et al. |
| 7,713,930 B2 | 5/2010 | Brunner-Schwarz et al. |
| 7,718,609 B2 | 5/2010 | Steiner et al. |
| 8,084,420 B2 | 12/2011 | Steiner et al. |
| 8,241,620 B2 | 8/2012 | Dahri-Correia et al. |
| 8,318,154 B2 | 11/2012 | Frost et al. |
| 8,637,458 B2 | 1/2014 | Pohl et al. |
| 8,933,023 B2 | 1/2015 | Pohl et al. |
| 9,060,927 B2 | 6/2015 | Steiner et al. |
| 9,089,476 B2 | 7/2015 | Soula et al. |
| 9,381,247 B2 | 7/2016 | Pohl et al. |
| 9,399,065 B2 | 7/2016 | Pohl et al. |
| 9,439,952 B2 | 9/2016 | Christe et al. |
| 9,492,467 B2 | 11/2016 | Soula et al. |
| 9,700,599 B2 | 7/2017 | Soula et al. |
| 9,795,678 B2 | 10/2017 | Soula et al. |
| 9,901,623 B2 | 2/2018 | Akers et al. |
| 9,993,555 B2 | 6/2018 | Akers et al. |
| 10,172,922 B2 | 1/2019 | Christe et al. |
| 10,583,175 B2 | 3/2020 | Soula et al. |
| 10,646,551 B2 | 5/2020 | Soula et al. |
| 2004/0131583 A1 | 7/2004 | Barritault et al. |
| 2004/0234616 A1 | 11/2004 | Sabetsky |
| 2005/0175611 A1 | 8/2005 | Mahler et al. |
| 2005/0282903 A1 | 12/2005 | Wade et al. |
| 2007/0020681 A1 | 1/2007 | Masada et al. |
| 2007/0086952 A1 | 4/2007 | Steiner et al. |
| 2007/0191757 A1 | 8/2007 | Steiner et al. |
| 2007/0235365 A1 | 10/2007 | Pohl et al. |
| 2008/0014250 A1 | 1/2008 | Soula et al. |
| 2008/0039365 A1 | 2/2008 | Steiner et al. |
| 2008/0039368 A1 | 2/2008 | Steiner et al. |
| 2008/0085298 A1 | 4/2008 | Pohl et al. |
| 2008/0090753 A1 | 4/2008 | Pohl et al. |
| 2008/0096800 A1 | 4/2008 | Pohl et al. |
| 2008/0234227 A1 | 9/2008 | Soula et al. |
| 2008/0248999 A1 | 10/2008 | Steiner |
| 2009/0048412 A1 | 2/2009 | Soula et al. |
| 2009/0175840 A1 | 7/2009 | Kashyap et al. |
| 2009/0192075 A1 | 7/2009 | Steiner |
| 2009/0221805 A1 | 9/2009 | Dahri-Correia et al. |
| 2009/0291114 A1 | 11/2009 | Soula et al. |
| 2009/0312236 A1* | 12/2009 | Beals .................. A61K 38/28 514/1.1 |
| 2010/0069292 A1 | 3/2010 | Pohl et al. |
| 2010/0137456 A1 | 6/2010 | Soula et al. |
| 2010/0166867 A1 | 7/2010 | Soula et al. |
| 2010/0167990 A1 | 7/2010 | Poulsen et al. |
| 2010/0167991 A1 | 7/2010 | Soula et al. |
| 2010/0184965 A1 | 7/2010 | Soula et al. |
| 2010/0227795 A1 | 9/2010 | Steiner et al. |
| 2010/0249020 A1 | 9/2010 | Soula et al. |
| 2011/0014189 A1 | 1/2011 | Soula et al. |
| 2011/0159068 A1 | 6/2011 | Soula et al. |
| 2011/0172166 A1 | 7/2011 | Charvet et al. |
| 2011/0195025 A1 | 8/2011 | Kett et al. |
| 2011/0195913 A1 | 8/2011 | Charvet et al. |
| 2011/0212901 A1 | 9/2011 | Akiyoshi et al. |
| 2011/0244530 A1 | 10/2011 | Toda et al. |
| 2011/0250653 A1 | 10/2011 | Toda et al. |
| 2011/0318429 A1 | 12/2011 | Ko |
| 2012/0041079 A1 | 2/2012 | Soula et al. |
| 2012/0094902 A1 | 4/2012 | Soula et al. |
| 2012/0178675 A1 | 7/2012 | Pohl et al. |
| 2012/0295833 A1 | 11/2012 | Charvet et al. |
| 2012/0309680 A1 | 12/2012 | Charvet et al. |
| 2013/0011378 A1 | 1/2013 | Yang et al. |
| 2013/0022592 A1 | 1/2013 | Vaughn et al. |
| 2013/0065826 A1 | 3/2013 | Soula et al. |
| 2013/0231281 A1 | 9/2013 | Soula et al. |
| 2013/0302275 A1 | 11/2013 | Wei et al. |
| 2014/0113856 A1 | 4/2014 | Pohl et al. |
| 2014/0135682 A1 | 5/2014 | Frost et al. |
| 2014/0142034 A1 | 5/2014 | Soula et al. |
| 2014/0187499 A1 | 7/2014 | Soula et al. |
| 2014/0336610 A1 | 11/2014 | Michel et al. |
| 2014/0357554 A1 | 12/2014 | Pohl et al. |
| 2014/0378373 A2 | 12/2014 | Soula et al. |
| 2015/0065423 A1 | 3/2015 | Laulicht et al. |
| 2015/0231160 A1 | 8/2015 | Soula et al. |
| 2015/0273022 A1 | 10/2015 | Wilson et al. |
| 2016/0015814 A1 | 1/2016 | Soula et al. |
| 2016/0082106 A1 | 3/2016 | Soula et al. |
| 2017/0136097 A1 | 5/2017 | Soula et al. |
| 2017/0143835 A1 | 5/2017 | Soula et al. |
| 2017/0368146 A1 | 12/2017 | Soula et al. |
| 2018/0140676 A1 | 5/2018 | Akers et al. |
| 2018/0236080 A1 | 8/2018 | Soula |
| 2019/0231851 A1 | 8/2019 | Akers et al. |

FOREIGN PATENT DOCUMENTS

| | | |
|---|---|---|
| CN | 1613862 A | 5/2005 |
| CN | 101316607 A | 12/2008 |
| CN | 101631804 A | 1/2010 |
| CN | 101835493 A | 9/2010 |
| CN | 101920019 A | 12/2010 |
| CN | 102216334 | 10/2011 |
| CN | 102300586 A | 12/2011 |
| CN | 102369019 A | 3/2012 |
| DE | 10355251 A1 | 6/2005 |
| EP | 0093551 A2 | 11/1983 |
| EP | 0190041 A2 | 8/1986 |
| EP | 0214826 A2 | 3/1987 |
| EP | 0280534 A2 | 8/1988 |
| EP | 0441563 A2 | 8/1991 |
| EP | 0608445 A1 | 8/1994 |
| EP | 0648495 A2 | 4/1995 |
| EP | 0681833 A2 | 11/1995 |
| EP | 0700683 A1 | 3/1996 |
| EP | 0787497 A2 | 8/1997 |
| EP | 1623979 A1 | 2/2006 |
| EP | 2300046 A2 | 3/2011 |
| EP | 2319500 A1 | 5/2011 |
| EP | 2403520 A1 | 1/2012 |
| EP | 2500020 A1 | 9/2012 |
| EP | 2711077 A1 | 3/2014 |
| EP | 2838506 A1 | 2/2015 |
| EP | 3372238 A1 | 9/2018 |
| FR | 2224164 A1 | 10/1974 |
| FR | 2914305 A1 | 10/2008 |
| FR | 2936800 A1 | 4/2010 |
| FR | 2943538 A1 | 10/2010 |
| FR | 2980796 A1 | 4/2013 |
| GB | 797959 A | 7/1958 |
| JP | S47-22571 U | 11/1972 |
| JP | S61-12899 A | 1/1986 |
| JP | H03-153653 A | 7/1991 |
| JP | H07-82225 A | 3/1995 |
| JP | H09-143194 A | 6/1997 |
| JP | H10-251287 A | 9/1998 |
| JP | 2007177182 A | 7/2007 |
| JP | 2007177185 A | 7/2007 |
| JP | 2010235477 A | 10/2010 |
| JP | 2011207798 A | 10/2011 |
| JP | 2012504697 A | 2/2012 |
| JP | 2012125162 A | 7/2012 |
| JP | 2015010075 A | 1/2015 |
| PL | 149145 B1 | 1/1990 |
| PT | 103003 A | 2/2005 |
| RU | 94026279 A | 6/1996 |
| WO | WO-198806599 | 9/1988 |
| WO | WO-199010645 | 9/1990 |
| WO | WO-1991009617 | 7/1991 |
| WO | WO-199633699 | 10/1996 |
| WO | WO-199717945 | 5/1997 |
| WO | WO-199733531 | 9/1997 |
| WO | WO-199749386 | 12/1997 |
| WO | WO-199934821 | 7/1999 |
| WO | WO-200043034 A2 | 7/2000 |
| WO | WO-2000064845 A1 | 11/2000 |

(56) References Cited

FOREIGN PATENT DOCUMENTS

| | | | |
|---|---|---|---|
| WO | WO-2001035943 A2 | 5/2001 | |
| WO | WO-2001052937 A1 | 7/2001 | |
| WO | WO-200220466 A1 | 3/2002 | |
| WO | WO-2002053190 A2 | 7/2002 | |
| WO | WO-2003000202 A2 | 1/2003 | |
| WO | WO-2003014371 A1 | 2/2003 | |
| WO | WO-2003057650 A2 | 7/2003 | |
| WO | WO-03094956 A1 | 11/2003 | |
| WO | WO-2004050620 A2 | 6/2004 | |
| WO | WO-2004056314 A2 | 7/2004 | |
| WO | WO-2004093833 A2 | 11/2004 | |
| WO | WO-2005072803 A1 | 8/2005 | |
| WO | WO-2005089722 A1 | 9/2005 | |
| WO | WO-2007038773 A1 | 4/2007 | |
| WO | WO-2007041481 A1 | 4/2007 | |
| WO | WO-2007074133 A2 | 7/2007 | |
| WO | WO-2007074456 A2 | 7/2007 | |
| WO | WO-2007116143 A1 | 10/2007 | |
| WO | WO-2007121256 A2 | 10/2007 | |
| WO | WO-2008038111 A1 | 4/2008 | |
| WO | WO-2008062466 A2 | 5/2008 | |
| WO | WO-2008084237 A2 | 7/2008 | |
| WO | WO-2008124522 A2 | 10/2008 | |
| WO | WO-2008152106 A1 | 12/2008 | |
| WO | WO-2009048945 A1 | 4/2009 | |
| WO | WO-2009048959 A1 | 4/2009 | |
| WO | WO-2009106386 A1 | 9/2009 | |
| WO | WO-2009115782 A2 | 9/2009 | |
| WO | WO-2009127940 A1 | 10/2009 | |
| WO | WO-2009/134380 A2 | 11/2009 | |
| WO | WO-2009136500 A1 | 11/2009 | |
| WO | WO-2010018324 A1 | 2/2010 | |
| WO | WO-2010028055 A1 | 3/2010 | |
| WO | WO-2010041119 A1 | 4/2010 | |
| WO | WO-2010041138 A2 | 4/2010 | |
| WO | WO-2010053140 A1 | 5/2010 | |
| WO | WO-2010058106 A1 | 5/2010 | |
| WO | WO-2010067613 A1 | 6/2010 | |
| WO | WO-2010102020 A1 | 9/2010 | |
| WO | WO-2010122385 A1 | 10/2010 | |
| WO | WO-2010149772 A1 | 12/2010 | |
| WO | WO-2011077405 A1 | 6/2011 | |
| WO | WO-2011089561 A1 | 7/2011 | |
| WO | WO-2011098962 A2 | 8/2011 | |
| WO | WO-2012002450 A1 | 1/2012 | |
| WO | WO-2012006283 A1 | 1/2012 | |
| WO | WO-2012078760 A1 | 6/2012 | |
| WO | WO-2012109112 A2 | 8/2012 | |
| WO | WO-2012124513 A1 | 9/2012 | |
| WO | WO-2012153070 A1 | 11/2012 | |
| WO | WO-2012153071 A2 | 11/2012 | |
| WO | WO-2012157656 A1 | 11/2012 | |
| WO | WO-2013021143 A1 | 2/2013 | |
| WO | WO-2013064787 A1 | 5/2013 | |
| WO | WO-2013104861 A1 | 7/2013 | |
| WO | WO-2013158618 A1 | 10/2013 | |
| WO | WO-2013177565 A1 | 11/2013 | |
| WO | WO-2014076423 A1 | 5/2014 | |
| WO | WO-2015106269 A2 | 7/2015 | |

OTHER PUBLICATIONS

U.S. Appl. No. 13/668,000, Rapid-acting insulin formulation comprising an oligosaccharide, filed Nov. 2, 2012, Abandoned, 20130231281.

U.S. Appl. No. 14/711,378, Rapid-acting insulin formulation comprising a substituted anionic compound and a polyanionic compound, filed May 13, 2015, Pending, 20160015814.

U.S. Appl. No. 14/712,696, Fast-acting insulin composition comprising a substituted anionic compound and a polyanionic compound, filed May 14, 2015, Issued, U.S. Pat. No. 9,795,678.

U.S. Appl. No. 15/353,522, Rapid-acting insulin composition comprising a substituted citrate, filed Nov. 16, 2016, Allowed, 20170136097.

U.S. Appl. No. 15/625,684, Fast-acting insulin composition comprising a citric acid salt, filed Jun. 16, 2017, Pending, 20180236080.

Aug. 22, 2019 Translation of Action issued in Japanese Patent Application No. 2017-207105.

"Sigma-Aldrich L-tryplophan" (downloaded online on Jan. 18, 2017 from URL: http:///www.sigmaaldrich.com/catalog/substance/ltrytophan204237322311?lang=en&region=US#).

"Sigma-Aldrich L-tryplophan" (downloaded online on Jan. 18, 2017 from URL: http:///www.sigmaaldrich.com/catalog/substance/ltyrosine181196018411?lang=en&region=US>).

Adediran, S.A. et al., "Deacylation Transition States of a Bacterial DD-Peptidase" Biochemistry, 45, 13074-13082 2006).

Ramesh & Chandrasekaran, But-2-ynylbisoxycarbonyl Chloride: A Novel C2-Symmetric Reagent for the Protection of Amines and Amino Acids, Organic Letters, 2005, 7(22), 4947-4950.

Ramesh & Chandrasekaran, "But-2-ynylbisoxycarbonyl Chloride: A Novel C2-Symmetric Reagent for the Protection of Amines and Amino Acids," Organic Letters, 2005, 7(22), with Supporting Information pp. 1-54.

Apr. 2, 2013 International Search Report issued in PCT/FR2012/052543.

Apr. 21, 2017 Office Action issued in Chinese Patent Application No. 201380059136.3.

Apr. 26, 2017 Office Action issued in Japanese Patent Application No. 2015-542338.

Apr. 27, 2016 Office Action issued in Chinese Application No. 201380059092.4.

Apr. 27, 2017 Office Action issued in Eurasian Patent Application No. 201590937/28.

Arranz et al., "Water-insoluble dextrans by grafting, 3a) Reaction of dextran with butyl isocyanate. Chemical hydrolysis," Makromol. Chem., vol. 188, pp. 2831-2838, 1987.

Aug. 22, 2019 Translation of Decision for Dismissal of Amendment issued in Japanese Patent Application No. 2017-207105.

Aug. 24, 2017 Office Action issued in Eurasian Patent Application No. 201590944/28.

Aug. 30, 2018 Office Action Issued in Eurasian Patent Application No. 201590944/28.

Azim, A., Shah, V., Dancel, G. F., Peterson, N., Gao, W., & Gross, R. (2006). Amino acid conjugated sophorolipids: a new family of biologically active functionalized glycolipids. Bioconjugate chemistry, 17(6), 1523-1529. (Year: 2006).

Baudys, Miroslav et al., "Extending Insulin Action in Vivo by Conjugation to Carboxymethyl Dextran," Bioconjugate Chem., (1998), Vo;. 9, p. 176-183.

Behe et al, "Quantitative assessment of the noncovalent inhibition of sickle hemoglobin gelation by phenyl derivatives and other known agents", Biochemistry, 1979, 18(19), 4196-4201.

Bergeron; "An investigation of the Impact of Molecular Geometry upon Microcapsule Self-Assembly", Journal of American Chemical Society, 1995, 117(25), 6658-65.

Bhaskar et al., "The Selective Silylation of d-Mannitol Assisted by Phenylboronic Acid and the Solid State and Solution Structures of the Intermediate 1,6-bis(silyl) bis(phenylboronates);"Journal of Carbohydrate Chemistry; 2003; pp. 867-879; vol. 22, 9.

Bovine ribonuclease b sequence (protein data bank, accession No. 1RBJ_, upload Oct. 10, 2012).

Brange, Jens et al., "Insulin analogs with improved pharmacokinetic profiles," Advanced Drug Delivery Reviews, 1999, vol. 35, pp. 307-335.

Carpino et al., "Efficiency in Peptide Coupling: 1-Hydroxy-7-azabenzotriazole vs 3,4-Dihydro-3-hydroxy-4-oxo-1,2,3-benzotriazine," Journal of Organic Chemistry, vol. 60, pp. 3561-3564, 1995.

Caulfield et al., "The Permeability of Glomerular Capillaries to Graded Dextrans," The Journal of Cell Biology, vol. 53, pp. 883-903, 1974.

Chang et al., "Permselectivity of the glomerular capillary wall: III. Restricted transport of polyanions," Kidney International, vol. 8, pp. 212-218, 1975.

(56) References Cited

OTHER PUBLICATIONS

ChEBI-70976 (downloaded online on Jan. 17, 2017 from URL: <http://www.ebi.ac.uk/chebi/searchId.do;sessionid= 0C30621862A25C54A3A6EFBB1CFB84D0?chebild= CHEBI:70976>).
Chemical Boor (downloaded online on Jan. 17, 2017 from URL: <http://www.chemicalbook.com/ ProductChemicalPropertiesCB7932982_EN.htm>).
Cho, Byung Tae et al., "Direct and indirect reductive amination of aldehydes and ketones with solid acid-activated sodium borohydride under solvent-free conditions", Tetrahedron, 2005, vol. 61, pp. 5725-5734.
Class notes for physical chemistry from the University of Washington http://www.ocean.washington.edu/courses/oc400/Lecture_Notes/CHPT6.pdf, Oct. 2004.
Coker et al, "Pathways for the Decay of Organic Dichloramines and Liberation of Antimicrobial Chloramine Gases", Chemical Research in Toxicology, 2008, 21(12), 2334-2343.
Coker et al., Supporting information for "Antimicrobial activity of chlorinated amino acids and peptides." Chemical Research in Toxicology, 2008, 21(12), 1-11.
Dec. 12, 2011 French Search Report issued in French Patent Application No. 1154039.
Dec. 18, 2015 Office Action issued in U.S. Appl. No. 14/079,437.
Dec. 17, 2018 Office Action Issued in Chinese Patent Application No. 201380059136.3.
Dec. 22, 2018 Translation of Office Action Issued in Eurasian Patent Application No. 201590937.
Definition of derivative and analog, from http://cancerweb.ncl.ac.uk/omd/about.html, pp. 1-5, accessed Jul. 7, 2005.
Definition of Phenylalanine, from Croatian English Chemistry Dictionary & Glossary {http://glossary.periodni.com/ Jlossary.php?en=phenylalanine, enclosed, pp. 1-2, Accessed Jan. 17, 2013.
Demitras et al, Inorganic Chemistry, Prentice-Hall International Inc., 1972, enclosed pp. 1-5.
Edwards et al., "Dispiroketals in Synthesis {Part 18): Regioselective and Enantioselective Protection of Symmetric Dolyol Substrates Using an Enantiopure {2S,2S)-Dimethyl-bis-dihydropyran; Synlett"; 1995; pp. 898-900; vol. 9.
Engelmann et al., "Preparation of Starch Carbamates in Homogeneous Phase using Different Mixing Conditions," Starch/Starke, 2001, pp. 560-569, vol. 53, Wiley-VCH Verlag GmbH.
Feb. 22, 2013 Office Action issued in U.S. Appl. No. 12/662,036.
Feb. 28, 2013 Office Action issued in U.S. Appl. No. 13/468,799.
Feb. 8, 2017 Office Action issued in Chinese Application No. 201380059092.4.
Fruchart et al, "A new linker for the synthesis of C-terminal peptide-oxo-aldehydes," Tetrahedron Letters, 1999, 40, 5225-6228.
Gartner et al, "Multistep small-molecule synthesis programmed by DNA templates", Journal of the American Chemical Society, 2002, 124(35), 10304-10306.
Giger, Katie et al., "Suppression of Insulin Aggregation by Heparin," Biomacromolecules, 2008, vol. 9, pp. 2338-2344.
Gildersleeve et al.; Improved Procedure for Direct Coupling of Carbohydrates to Proteins via Reductive Amination Bioconjug Chem.; Jul. 2008; pp. 1485-1490; vol. 19, No. 7.
Gorecki et al, "Peptide inhibitors of sickle hemoglobin aggregation: effect of hydrophobicity", Biochemistry, 1980, 19(8), 1564-1568.
Granger, Elisabeth et al., "Simplified syntheses of complex multifunctional nanomaterials." Chem. Communication 2008) 4792-4794.
Heinze et al.; "Functional Polymers Based on Dextran;" Adv. Polym. Sci.; 2006; pp. 199-291; vol. 205; Springer-Verlag Berlin Heidelberg.
Hong et al, "Determination of inhibitory constants for CPA by competitive spectrophotometry", Peptides: Biology and Chemistry, Proceedings of the Chinese Peptide Symposium, 5th, Lanzhou, China, Jul. 14-17, 1998 (2000).
Huffman et al, "Substrate specificity of isopenicillin N synthase", Journal of Medicinal Chemistry, 1992, 35, 1897-1914.

Humme, "Amino acid derivatives hydrolyzable by an enzyme of rennet. III. Peptides", Nederlands Melk-en Zuivellijdschrifl, 1971, 25(1), 3-14.
Huus, Kasper et al., "Thermal Dissociation and Unfolding of Insulin", Biochemistry, 2005, vol. 44, pp. 11171-11177.
Jan. 22, 2016 Office Action issued in U.S. Appl. No. 14/581,239.
Jul. 11, 2018 Translation of Office Action Issued in Israeli Patent Application No. 234684.
Jul. 12, 2010 Search Report issued in International Patent Application No. PCT/IB2010/000711.
Jul. 12, 2010 Written Opinion issued in International Patent Application No. PCT/IB2010/000711.
Jul. 2018 Office Action issued in Israel Patent Application No. 238446.
Jul. 22, 2016 Office Action Issued in U.S. Appl. No. 14/712,696.
Jul. 23, 2017 Office Action issued in Israeli Patent Application No. 238303.
Jul. 24, 2013 Office Action issued in U.S. Appl. No. 12/662,036.
Jul. 27, 2018 Office Action issued in U.S. Appl. No. 15/410,524.
Jul. 28, 2017 Office Action issued in Japanese Patent Application No. 2015-542337.
Jul. 3, 2017 Office Action issued in Australian Patent Application No. 2013346623.
Jul. 31, 2017 Office Action issued in Australian Patent Application No. 2013346624.
Jun. 25, 2014 Office Action issued in U.S. Appl. No. 13/668,000.
Kalra, Sanjay et al., "Ultra-fast acting insulin analogues", Recent Patents on Endocrine, Metabolic & Immune Drug Discovery, 2014, vol. 8-2, pp. 117-123.
Kartvelishvili et al, Amino acid based bioanalogous polymers. Synthesis of novel poly(urethane amide)s based on N, N'-(trimethylenedioxy-dicarbonyl)bis(phenylalanine), Macromolecular Chemistry and Physics, 1996, 197, 249-257.
Khosla et al, "Synthesis of mixed Na, NE-peptides of lysine through direct Nt-peptidation", Journal of Scientific and Industrial Research, Section B: Physical Sciences, 1962, 218, 318-321.
Larsen, "Dextran prodrugs—structure and stability in relation to therapeutic activity," Advanced Drug Delivery Reviews, 1989, pp. 103-154, vol. 3, Elsevier.
Lindhorst, Thisbe K., "O-Glycoside synthesis", Essentials of Carbohydrate Chemistry and Biochemistry, 2007, pp. 157-208.
Liu et al, "Ring opening polymerization of aliphatic cyclic carbonates in the presence of natural amino acids", Journal o Applied Polymer Science, 2008, 107(5), 3275-3279.
Liwschitz et al, The reaction of N-maleoylamino acids with benzylamine, Journal of the Chemical Society, 1962, 3726-3729.
Lodi et al, "Chiral aminoaci containing acyclic ligands. I. Syntheses and conformations", Tetrahedron, 1982, vol. 38, N° 14, pp. 2055-2060.
Lou, Xianwen et al., "Simulation of size exclusion chromatography for characterization of supramolecular complex: a theoretical study," Journal of Chromatography A, 2004, vol. 1029, pp. 67-75.
Mar. 1, 2017 Office Action issued in U.S. Appl. No. 14/712,328.
Mar. 16, 2017 European Office Action issued in European Patent Application No. 13 801 655.5.
Mar. 7, 2017 Office Action issued in U.S. Appl. No. 14/711,378.
Mar. 8, 2019 Office Action Issued in U.S. Appl. No. 15,410,524.
Marchelli et al, "Chiral aminoaci containing acyclic ligands. II. Compexation of alkaline earth cations", Tetrahedron, 1982, vol. 38, N°14, pp. 2061-2067.
May 10, 2019 Office Action issued in Australian Patent Application No. 2018204764.
May 17, 2016 Office Action Issued in U.S. Appl. No. 14/711,378.
May 2, 2019 Office Action Issued in U.S. Appl. No. 14/711,378.
May 21, 2015 Office Action issued in U.S. Appl. No. 14/079,437.
May 28, 2014 Office Action issued in U.S. Appl. No. 13/468,849.
May 3, 2012 French Search Report issued in French Patent Application No. 1158885.
May 7, 2017 Office Action issued in Saudi Arabian Application No. 515360428.
May 8, 2019 Hearing Notice Issued in Indian Patent Application No. 1379/KOLNP/2015.
Memo, Myriad-Mayo guidance, Mar. 2014.

(56) References Cited

OTHER PUBLICATIONS

Menzenski et al, "Self-assembly of supramolecular nanostructures from phenylalanine derived bolaamphiphiles", New Journal of Chemistry, 2007, vol. 31, pp. 1674-1680.
Nov. 15, 2016 International Preliminary Report on Patentability issued in International Application No. PCT/ EP2015/060716.
Nov. 15, 2016 International Preliminary Report on Patentability issued in PCT Patent Application No. PCT/ EP2015/060732.
Nov. 15, 2016 International Preliminary Report on Patentability issued in PCT Patent Application No. PCT/ EP2015/060820.
Swamy et al., "Synthesis of iron (III), cobalt (II), nickel (II), copper (II) and zinc (II) complexes with new quadridentate N, O-donor ligands", Oriental Journal of Chemistry, 2008, 24(3), 1103-1106.
Oct. 14, 2009 Search Report issued in French Patent Application No. 723351.
Oct. 15, 2014 Office Action issued in U.S. Appl. No. 14/079,437.
Ouari et al., "Synthesis of a Glycolipidic Amphiphilic Nitrone as a New Spin Trap," J_ Org. Chem., 1999, pp. 3554-3556, vol. 64, American Chemical Society {with 10 pages of supporting information).
Pal et al., Molecular mechanism of physical gelation of hydrocarbons by fatty acid amides of natural amino acids, Tetrahedron; 2007; pp. 7334-7348; vol. 63.
Polymer Molecular Weight Distribution and Definitions of MW Averages, from www.agelini.com/chem, pp. 1-4 May 10, 2011.
R. Janowski, et al., "Two Polymorphs of a Covalent Complex Between Papain and a Diazomethylketone Inhibitor," J_ Peptide Res. 64, 2004, pp. 141-150.
Ramesh & Chandrasekaran, "But-2-ynylbisoxycarbonyl Chloride: A Novel C2-Symmetric Reagent for the Protection of Amines and Amino Acids," Org. Lett.; 2005; pp. 4947-4950.
Roussel et al., "Monolayer lipid membrane-forming dissymmetrical bolaamphiphiles derived from alginate oligosaccharides;" Chem. Communication; 2006; pp. 3622-3624.
Rudd, Pauline M. et al., "Glycoforms modify the dynamic stability and functional activity of an enzyme." Biochemistry 1994) 33 p. 17-22.
Ruiz-Pena et al., "Physico-chemical studies of molecular interactions between non-ionic surfactants and bovine serum albumin; Colloids" and Surfaces B: Biointerfaces: 2010: pp. 282-289; vol. 75.
Sawardeker, Jawahar S. et al., "Quantitative determination of monosaccharides as their alditol acetates by gas liquid chromatography." Anal. Chem. (1965) 37 (12) p. 1602-1604.
Schuster et al, "Chymotryspin-catalyzed peptide synthesis in ice: use of unprotected amino acids as acyl acceptors", Tetrahedron Letters, 1993, 34(36), 5701-5702.
Sep. 18, 2019 Office Action issued in Korean Patent Application No. 10-2015-7015793.
Sep. 19, 2012 Office Action issued in U.S. Appl. No. 12/662,036.
Sep. 24, 2018 Office Action Issued in Indian Patent Application No. 1398/KOLNP/2015.
Sep. 8, 2017 Office Action issued in European Patent Application No. 12726819.1.
Sep. 8, 2018 Office Action Issued in Indian Patent Application No. 1379/KOLNP/2015.
Shen et al., "Synthesis and Characterization of Cellulose Carbamates Having alpha-Amino Acid Moieties," Polymer Bulletin, 2005, pp. 317-322, vol. 55.
Shimadzu scientific publication SC-AP-GC-0138, downloaded Dec. 1, 2015.
Siddique & Duhamel, "Effect of Polypeptide Sequence on Polypeptide Self-Assembly", Langmuir, 2011, 27(11), 5639-6650.
Siddique & Duhamel, Supporting Information for "Effect of Polypeptide Sequence on Polypeptide Self-Assembly", Langmuir, 2011, 27(11), 6639-6650.
Sigma-Aldrich L-tryptophan {downloaded online on Jan. 18, 2017 from URL: <hllp:///www.sigmaaldrich.com/catalog/.
Sigma-Aldrich L-tyrosine {downloaded online on Jan. 18, 2017 from URL: <http://www.sigmaaldrich.com/catalog/.
Sisu, Ioana et al., "Synthesis and structural characterization of amino-functionalized polysaccharides", Central European Journal of Chemistry, 2009, vol. 7, No. 1, pp. 66-73.
Smoot et al., "Oligosaccharide Synthesis From Conventional Methods to Modern Expeditious Strategies," Advances n Carbohydrate Chemistry and Biochemistry; 2009; pp. 161-251: vol. 62.
Solomons, T.W. Graham; Organic Chemistry, 4th edition, (1988) ISBN 0-471-83659-1, p. 751.
Song et al., 6-o-Amino-2-0-carboxymethyl Glucopyranoside as Novel Glycoaminoxy Acid Building Block for the construction of Oligosaccharide Mimetics; Synthesis; 2011; pp. 2761-2766; No. 17.
Sun et al, "Homo-cysteinyl peptide inhibitors of the L1 metallo-B-lactamase, and SAR as determined by combinatorial library synthesis", Bioorganic Medicinal Chemistry Letters, 2006, 16(19), 5169-5175.
Swamy et al, "Synthesis of iron (III), cobalt (II), nickel (II), copper (II) and zinc (II) complexes with new quadridentate N, O donor ligands," Journal of the Indian Chemical Society 77(7):336-338; Jul. 2000.
Tachibana, Y., Monde, K., & Nishimura, S. I. (2004). Sequential glycoproteins: Practical method for the synthesis of antifreeze glycoprotein models containing base labile groups. Macromolecules, 37(18), 6771-6779. (Year: 2004).
Takeoka, Shinji et al., "Physical properties and packing states of molecular assemblies of synthetic glycolipids in aqueous dispersions", Journal of the Chemical Society, Faraday Transactions, 1998, vol. 94, No. 15, pp. 2151-2158.
Tareq et al., "Leodoglucomides A and B from a Marine-Derived Bacterium *Bacillus lichentiformis*;" Organic Letters; 2012; pp. 1464-1467; vol. 14, No. 6.
The HLB System: a time saving guide to emulsifier selection, revised ed., ICI Americas Inc., Mar. 1980, pp. 1-22.
Translation of Jul. 4, 2019 Office Action Issued in Israeli Office Action No. 261726.
Translation of Jun. 4, 2019 Office Action Issued in Mexican Patent Application No. MX/a/2015/005423.
Translation of Mar. 20, 2018 Office Action issued in Chinese Patent Application No. 201380059136.3.
Tsai et al., "Synthesis of Amino Acid Ester Isocyanates: Methyl (S)-2-Isocyanato-3-Phenylpropanoate Benzenepropanoic acid, a-isocyanate-, methyl ester, (S)]," Organic Syntheses Coll., vol. 10, p. 544-545, 2004.
Tschantz, William R. et al., "Substrate Binding is Required for Release of Product from Mammalian Protein rarnesyltransferase," The Journal of Biological Chemistry, 1997, vol. 272, No. 15, pp. 9989-9993.
Tse et al, "Translation of a DNA into a Library of 13000 Synthetic Small-Molecule Macrocycles Suitable for in Vitro Selection", Journal of the American Chemical Society, 2008, 130(46), 15611-15626.
Tse et al, "Translation of DNA into a Library of 13000 Synthetic Small-Molecule Macrocycles Suitable for in Vitro Selection", Journal of the American Chemical Society, 2008, 130(46), with Supporting Information pp. 1-9.
U.S. Appl. No. 12/662,036 to Soula et al., filed Mar. 29, 2010.
U.S. Appl. No. 13/287,793 to Soula et al., filed Nov. 2, 2011.
U.S. Appl. No. 13/468,799 to Charvet et al., filed May 10, 2012.
U.S. Appl. No. 13/468,849 to Charvet et al., filed Jul. 11, 2012.
U.S. Appl. No. 14/079,437, filed Nov. 13, 2013 in the name of Soula et al.
U.S. Appl. No. 14/581,239, filed Dec. 23, 2014 in the name of Soula et al.
U.S. Appl. No. 14/711,378, filed May 13, 2015 in the name of Soula et al.
U.S. Appl. No. 14/712,328, filed May 14, 2015 in the name of Soula.
U.S. Appl. No. 14/712,696, filed May 14, 2015 in the name of Soula et al.
U.S. Appl. No. 15/353,522, filed Nov. 16, 2016 in the name of Soula et al.
U.S. Appl. No. 15/410,524, filed Jan. 19, 2017 in the name of Soula et al.
U.S. Statutory Invention Registration No. H645, published Jun. 6, 1989.

(56) References Cited

OTHER PUBLICATIONS

Uversky, Vladimir N. et al., "Prediction of the Association State of Insulin Using Spectral Parameters", Journal of Pharmaceutical Sciences, Apr. 2003, vol. 92, No. 4, pp. 847-858.

Van Bogaert, I. N., Zhang, J., & Soetaert, W. (2011). Microbial synthesis of sophorolipids. Process Biochemistry, 46(4), 821-833. (Year: 2011).

Votano et al, "Inhibition of deoxyhemoglobin S polymerization by biaromatic peptides found to associate with the hemoglobin molecule at a preferred site", Biochemistry, 1985, 24, 1966-1970.

Wagner, Herman L., "The Mark-Houwink-Sakurada equation for the viscosity of linear polyethylene." J_ Phys. Chem. Ref. Data (1985) 14(2) p. 611-617.

Watanabe et al., "Synthesis of lipid A type carboxymethyl derivatives with ether chains instead of ester chains and heir LPS-antagonistic"activities; "Carbohydrate" Research; 2003; pp. 47-54; vol. 338.

Wayne, Richard P., Principles and applications of photochemistry (1988) ISBN 0-19-855234-3.

Won, "Synthesis of heterobifunctional poly{ethylene glycol) containing an acryloyl group at one end and an isocyanate Jroup at the other end," Polymer Bulletin, 2004, pp. 109-115, vol. 52.

Wu et al.; Reactive Impurities in Excipients: Profiling, Identification and Mitigation of Drug-Excipient Incompatibility; I/APS PharmSciTech; Dec. 2011; pp. 1249-1263; vol. 12, No. 4.

Yalpani, Manssur et al., "Selective Chemical Modifications of Dextran", Journal of Polymer Science, 1985, vol. 23, p. 1395-1405.

Zhang, L., Liu, W., Han, B., & Wang, D. (2007). Synthesis and antitumor activity of arginine-glucosamine conjugate. Carbohydrate polymers, 69(4), 644-650. (Year: 2007)A161.

Zhang, Tianhong et al., "Novel Polysaccharide Surfactants: Synthesis of Model Compounds and Dextran-Based Surfactants", Macromolecules, 1994, vol. 27, pp. 7302-7308.

Bedu-Addo, "Understanding Lyophilization Formulation Development," Pharmaceutical Technology, (2004), 9 pages.

Brange, "Studies on the physical and chemical stability in pharmaceutical formulation" Klumwer Academic Publisher, (1994), 31 pages.

Brange, et al., "Insulin Structure and Stability," Stability and Characterization of Protein and Peptide Drugs: Case Histories, (1993), Chapter 11, pp. 315-350.

Brange, et al., "Monomeric insulins obtained by protein engineering and their medical implications," Nature (1988), vol. 333, pp. 679-682.

Business Insights "The Diabetes Market Outlook to 2016," May 2011, 132 pages.

Capelle, et al, "High Throughput Screening of Protein Formulation Stability: practical Considerations," European Journal of Pharmaceutics and Biopharmaceutics, vol. 65, No. 2, Jan. 2007, pp. 131-148.

Center for Biologics Evaluation and Research, "Guideline for the determination of residual moisture in dried biological products," (1990), 7 pages.

Cotton & Wilkinson, Advanced Inorganic Chemistry 4th Ed, (1981), pp. 12-16.

Cotton & Wilkinson, Advanced Inorganic Chemistry 5th Ed, (1989), pp. 98-109.

Fineberg, et al., "Immunologic Effects of Insulin Lispro [Lys (b28), Pro (B29) Human Insulin] in IDDM and NIDDM Patients Previously Treated with Insulin," Diabetes (1996), vol. 45, pp. 1750-1754.

Gatlin, L.A.; Gatlin, C.A.B. Formulation and administration techniques to minimize injection pain and tissue damage associated with parenteral products. In Injectable Drug Development: Techniques to Reduce Pain and Irritation; Gapta, P.K., Brazeau, G.A., Eds.; Interpharm Press: Denver, CO, USA, 1999; pp. 401-425.

Heinemann et al., "U-100, pH-Neutral formulation of VIAject®: faster onset of action than insulin lispro in patients with type 1 diabetes," Diabetes, Obesity and Metabolism, (2011), pp. 1-6.

Humalog, "Scientific Discussion," EMEA (2005) 9 pages.

Huus, et al., "Chemical and Thermal Stability of Insulin: Effects of Zinc and Ligand Binding to the Insulin Zinc-Hexamer," Pharm. Res. (2006), vol. 23, No. 11, pp. 2611-2620.

Huus, et al., "Thermal Dissociation and Unfolding of Insulin," Biochemistry (2005), vol. 44, pp. 11171-11177.

Martin, "pH as a variable in free zinc ion concentration from zinc-containing lozenges," Antimicrob. Agents Chemother, (1988), Vo. 32, No. 4, pp. 608-609.

Muller R.H Hildebrand. Pharmazeutische Technologie 2nd Ed 1998 pp. 24-28.

Nyborg et al., "That zincing feeling: the effects of EDTA on the behavior of zinc-binding transcriptional regulators," Biochem. J. (2004), vol. 381, pp. e3-e4.

Pohl et al, Ultra-Rapid Absorption of Recombinant Human Induced by Zinc Chelation and Surface Charge Masking, J. Diabetes Sci Technol 2012; vol. 6, Issue 4, pp. 755-563.

Pohl, et al., "Development of Ultra-Rapid-Acting Prandial Insuliin Analogs Requires Chelation of Zinc Ions and Charge Masking to Increase the Rate of Subcutaneous Absorption," EASD Poster (Sep. 2012) 1 page.

Prahbu, et al., "A study of factors controlling dissolution kinetics of zinc complexed protein suspensions in various ionic species," International Journal of pharmaceutics, (2001), vol. 217, No. 1, pp. 71-78.

Shamaev & Zografi, "How Does Residual Water Affect the Solid-State Degradation of Drugs in the Amorphous State?," (1996), J. Pharm. Sci, vol. 85, No. 11, pp. 1137-1141.

Cover page of arbitration between Adocia S.A., Claimant and Eli Lilly and Company, Respondent.

Civil Action No. 1:18-cv-03133; *Eli Lilly* v. *Adocia*, Complaint filed Oct. 9, 2018, 55 pages.

Civil Action No. 1:18-cv-03133; *Eli Lilly* v. *Adocia*, Answer and Counterclaims filed Jan. 10, 2019, 82 pages.

Civil Action No. 1:18-cv-03133; *Eli Lilly* v. *Adocia*, Lilly Answer to Counterclaims filed Feb. 21, 2019, 21 pages.

Civil Action No. 1:18-cv-03133; *Eli Lilly* v. *Adocia*, Stipulated Consent Judgment filed Oct. 6, 2019, 2 pages.

Notice of Opposition filed in EP2319500, dated Jul. 24, 2013, 38 pages.

Notice of Opposition filed in EP2106790, dated Jul. 24, 2013, 37 pages.

Eli Lilly; Humalog AAD_0025NL5532AMP; 2016.

Eli Lilly; Highlights of Prescribing Information; 2000.

Krasner et al. (2013) "Lispro Formulations BIOD-238 and BIOD-250 Associated With Faster Absorption and Declines From Peak Concentrations Compared to Humalog®," 73rd Scientific Sessions, American Diabetes Association, vol. 62, Suppl. 1A, LB12, Abstract 44-LB.

Pandyarajan et al. (2012) "Design of Non-Standard Insulin Analogs for the Treatment of Diabetes Mellitus," *Curr Diab Rep* 12(6):697-704.

Welling et al. (2014) "The role of citric acid in oral peptide and protein formulations: Relationship between calcium chelation and proteolysis inhibition," European Journal of Pharmaceuticals and Biopharmaceutics 86:544-551.

G. Williams et al: "Prostaglandin E 1 Accelerates Subcutaneous Insulin Absorption in Insulin-dependent Diabetic Patients", Diabetic Medicine., vol. 1, No. 2, Jul. 1, 1984 (Jul. 1, 1984), pp. 109-113, XP055146928, GB ISSN: 0742-3071, DOI: 10.1111/j.1464-5491.1984.tb01939.x.

Product Information for Remodulin® (treprostinil sodium) Injection, United Therapeutics Corporation, Feb. 2008.

Highlights of Prescribing Information for Humalog® (insulin lispro injection), Eli Lilly and Company, revised Mar. 2013.

Summary of Product Characteristics for Actrapid, Novo Nordisk A/S, Sep. 18, 2007.

A. M. Gualandi-Signorini et al: "Insulin formulations—a review", Eur Rev Med Pharmacol Sci. May-Jun. 2001; 5(3):73-83.

J. Schlichtkrull: "The absorption of insulin", Acta Paediatr. Scan. (suppl 270) 1977, 97-102.

K. K. Mubarak: "A review of prostaglandin analogs in the management of patients with pulmonary arterial hypertension", Respiratory Medicine (2010), 104, 9-21.

(56) References Cited

OTHER PUBLICATIONS

The European Alprostadil Study Group: "The long-term safety of alprostadil (prostaglandin-E1) in patients with erectile dysfunction", British Journal of Urology (1998), 82, 538-543.
Observations by Third Parties filed in EP3372238 on Mar. 3, 2020, 7 pages.
Technical Primer Cited in Third Party Observations in EP3372238; dated Mar. 3, 2020, 2 pages.

* cited by examiner

RAPID-ACTING INSULIN FORMULATION COMPRISING A SUBSTITUTED ANIONIC COMPOUND

The present application is a continuation of U.S. patent application Ser. No. 16/687,339 filed on Nov. 18, 2019, which is a continuation of application Ser. No. 15/609,670 filed May 31, 2017, which is a continuation of application Ser. No. 14/079,516 filed Nov. 13, 2013, which claims the benefit of and priority to U.S. provisional Application No. 61/726,349 filed Nov. 14, 2012; U.S. provisional Application No. 61/725,775 filed Nov. 13, 2012; French Patent Application No. FR 12/60855 filed Nov. 14, 2012; and French Patent Application No. FR 12/60808 filed Nov. 13, 2012. Each of the prior applications is incorporated herein by reference in its entirety.

The present invention relates to a rapid-acting insulin formulation.

Since the production of insulin by genetic engineering, at the start of the 1980s, diabetic patients have benefited from human insulin for their treatment. This product has greatly improved this therapy, since the immunological risks associated with the use of non-human insulin, in particular pig insulin, are eliminated. However, subcutaneously-injected human insulin has a hypoglycemiant effect only after 60 minutes, which means that diabetic patients treated with human insulin must take the injection 30 minutes before a meal.

One of the problems to be solved for improving the health and comfort of diabetic patients is that of providing them with insulin formulations which afford a faster hypoglycemiant response than that of human insulin, if possible a response approaching the physiological response of a healthy person. The secretion of endogenous insulin in a healthy individual is immediately triggered by the increase in glycemia. The object is to minimize the delay between the injection of insulin and the start of the meal.

At the present time, it is accepted that the provision of such formulations is useful in order for the patient to receive the best possible health care.

Genetic engineering has made it possible to afford a response with the development of rapid insulin analogs. These insulins are modified on one or two amino acids so as to be more rapidly absorbed into the blood compartment after a subcutaneous injection. These insulins lispro (Humalog®, Lilly), aspart (Novolog®, Novo) and glulisine (Apidra®, Sanofi Aventis) are stable insulin solutions with a faster hypoglycemiant response than that of human insulin. Consequently, patients treated with these rapid insulin analogs can take an insulin injection only 15 minutes before a meal.

The principle of rapid insulin analogs is to form hexamers at a concentration of 100 IU/mL to ensure the stability of the insulin in the commercial product while at the same time promoting very rapid dissociation of these hexamers into monomers after subcutaneous injection so as to obtain rapid action.

Human insulin as formulated in its commercial form does not make it possible to obtain a hypoglycemiant response close in kinetic terms to the physiological response generated by the start of a meal (increase in glycemia), since, at the working concentration (100 IU/mL), in the presence of zinc and other excipients such as phenol or m-cresol, it assembles to form a hexamer, whereas it is active in monomer and dimer form. Human insulin is prepared in the form of hexamers so as to be stable for up to 2 years at 4° C., since, in the form of monomers, it has a very high propensity to aggregate and then to fibrillate, which makes it lose its activity. Furthermore, in this aggregated form, it presents an immunological risk to the patient.

The dissociation of the hexamers into dimers and of the dimers into monomers delay its action by close to 20 minutes when compared with a rapid insulin analog (Brange J., et al., Advanced Drug Delivery Review, 35, 1999, 307-335).

In addition, the kinetics of passage of the insulin analogs into the blood and their glycemia reduction kinetics are not optimal, and there is a real need for a formulation which has an even shorter action time in order to come close to the kinetics of endogenous insulin secretion in healthy individuals.

The company Biodel has proposed a solution to this problem with a human insulin formulation comprising EDTA and citric acid as described in patent application US 200839365. The capacity of EDTA to complex zinc atoms and the interactions of citric acid with the cationic regions present at the surface of insulin are described as destabilizing the hexameric form of insulin and thus as reducing its action time.

However, such a formulation especially has the drawback of disassociating the hexameric form of insulin, which is the only stable form capable of meeting the stability requirements of the pharmaceutical regulations.

PCT patent application WO 2010/122385 in the name of the Applicant is also known, describing human insulin or insulin analog formulations that can solve the various problems mentioned above via the addition of a substituted polysaccharide comprising carboxyl groups.

However, the requirements entailed by the chronic and intensive use or even the pediatric use of such formulations lead a person skilled in the art to seek to use excipients whose molar mass and size are as small as possible in order to facilitate their elimination.

The polysaccharides described in patent applications WO 2010/122385A1 and US 2012/094902A1 as excipients are compounds consisting of chains whose lengths are statistically variable and which are very rich in possible sites of interaction with protein active principles. This richness might induce a lack of specificity in terms of interaction, and a smaller and better defined molecule might make it possible to be more specific in this respect.

In addition, a molecule with a well-defined backbone is generally more easily traceable (for example MS/MS) in biological media during pharmacokinetic or ADME (administration, distribution, metabolism, elimination) experiments when compared with a polymer which generally gives a very diffuse and noisy signal in mass spectrometry.

Conversely, it is not excluded that a well-defined and shorter molecule might have a deficit of possible sites of interaction with protein active principles. Specifically, on account of their reduced size, they do not have the same properties as polymers of polysaccharide type since there is loss of the polymer effect, as is demonstrated in the comparative examples of the experimental section; see especially the tests of insulin dissolution at the isoelectric point and the tests of interaction with a model protein such as albumin.

Despite these discouraging results, the Applicant has succeeded in developing formulations that are capable of accelerating insulin by using a substituted anionic compound in combination with a polyanionic compound.

Furthermore, as in the case of the use of polysaccharides, the hexameric nature of insulin is not affected, and thus the stability of the formulations is not affected, as is moreover confirmed by the examples of state of association of human insulin and insulin analog via circular dichroism in the presence of a substituted anionic compound according to the invention.

The present invention makes it possible to solve the various problems outlined above since it makes it possible especially to prepare a human insulin or insulin analog formulation, which is capable, after administration, of accelerating the passage of the human insulin or of analogs thereof into the blood and of more quickly reducing glycemia when compared with the corresponding commercial insulin products.

Following is a brief description of the drawings.

FIG. 1: DGlucose (mM) as a function of time after injection (min.). Curve plotted with the squares corresponding to example B8, glucose Tmin=30±11 min, curve plotted with the triangles corresponding to example B2, glucose Tmin=44±14 min.

Figure 2:
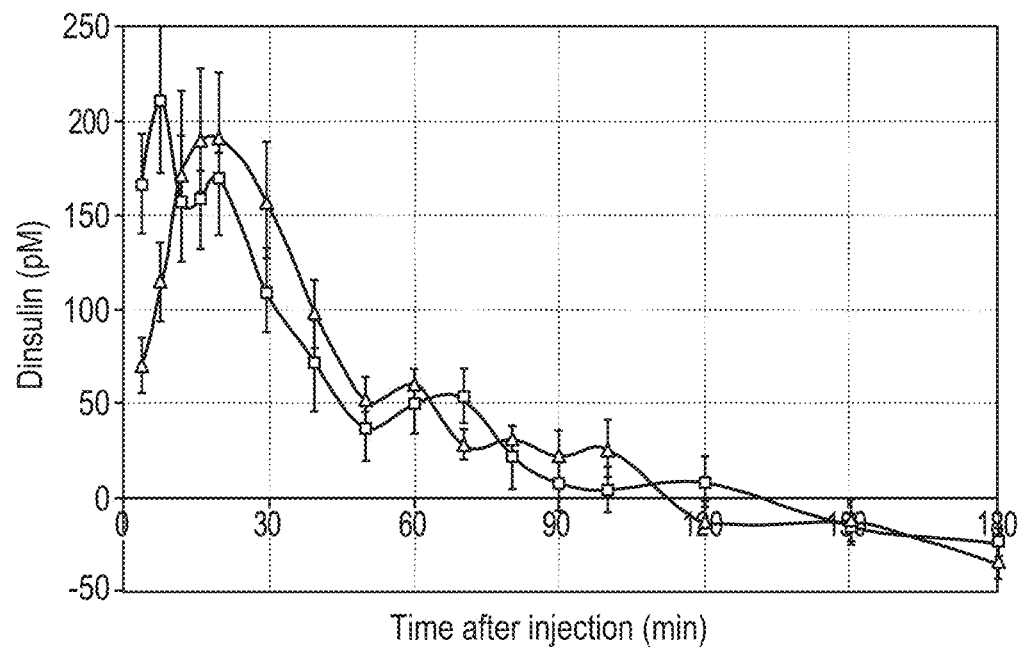

FIG. 2: DInsulin (pM) as a function of time after injection (min.). Curve plotted with the squares corresponding to example B8, insulin Tmax=11±6 min, curve plotted with the triangles corresponding to example B2, insulin Tmax=18±8 min.

Figure 3:
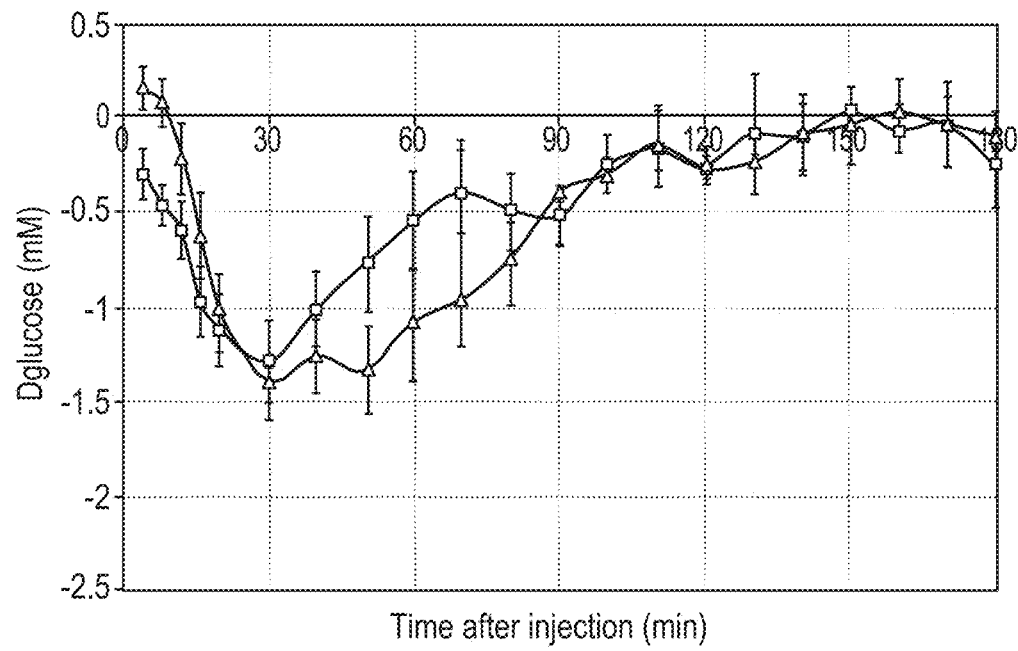

FIG. 3: DGlucose (mM) as a function of time after injection (min.). Curve plotted with the squares corresponding to example B10, glucose Tmin=33±13 min, curve plotted with the triangles corresponding to example B2, glucose Tmin=44±14 min.

Figure 4:
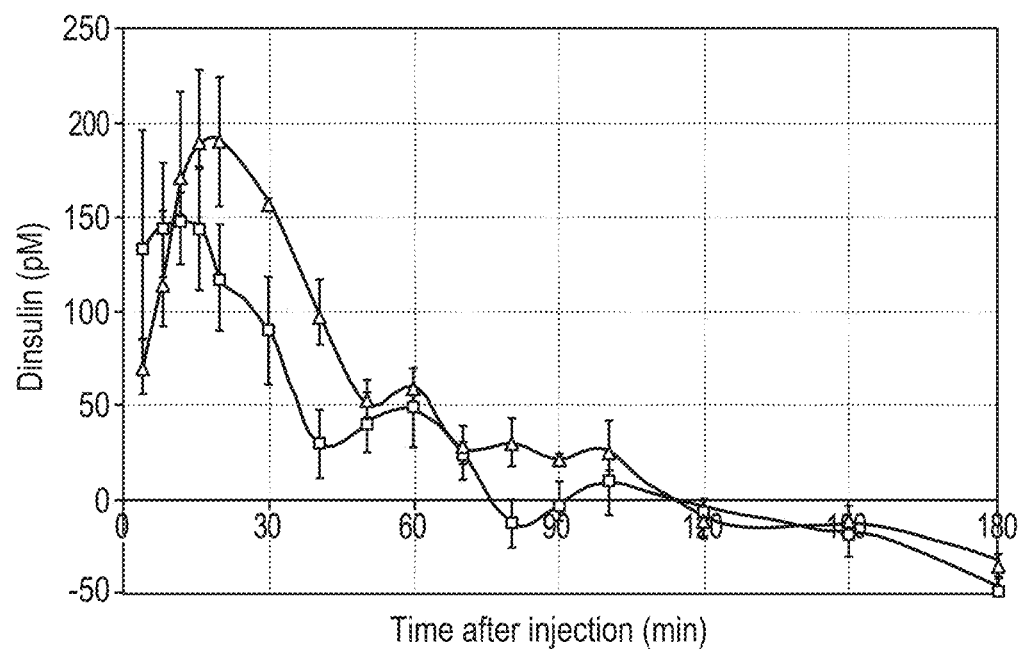

FIG. 4: DInsulin (pM) as a function of time after injection (min.). Curve plotted with the squares corresponding to example B10, insulin Tmax=15±9 min, curve plotted with the triangles corresponding to example B2, insulin Tmax=18±8 min.

Figure 5:
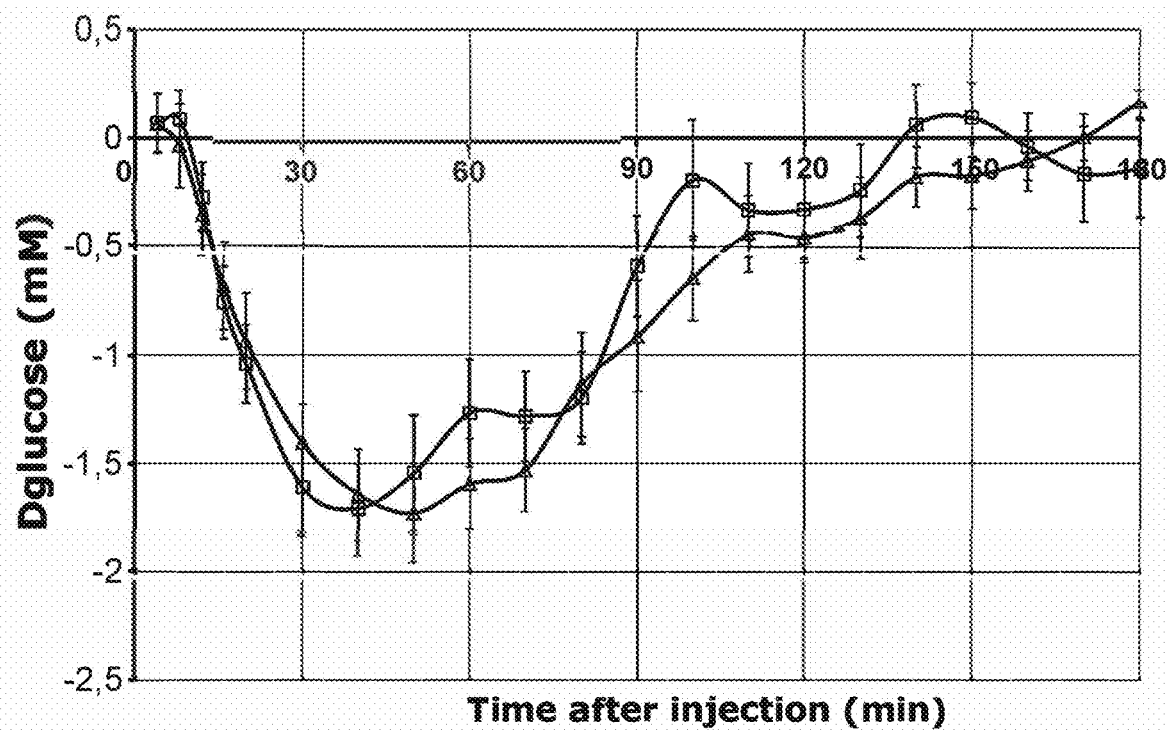

FIG. 5: DGlucose (mM) as a function of time after injection (min.). Curve plotted with the squares corresponding to example B7, glucose Tmin=41±16 min, curve plotted with the triangles corresponding to example B2, glucose Tmin=50±14 min.

Figure 6:
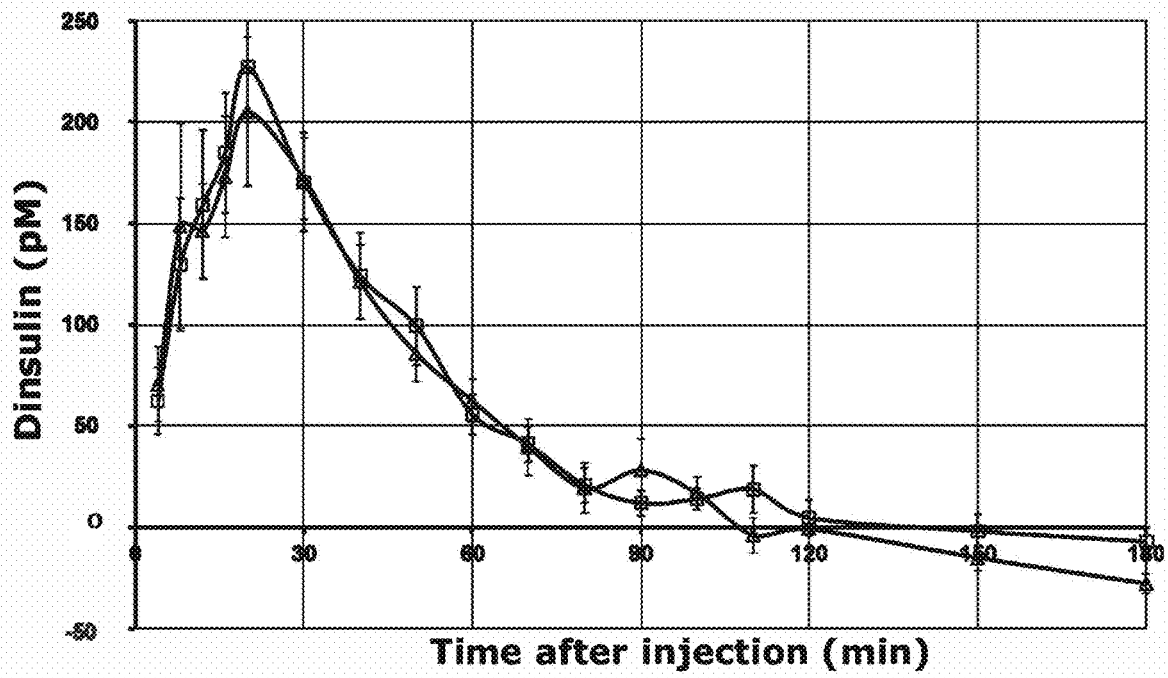

FIG. 6: DInsulin (pM) as a function of time after injection (min.). Curve plotted with the squares corresponding to example B2, insulin Tmax=21±10 min, curve plotted with the triangles corresponding to example B2, insulin Tmax=20±9 min.

Figure 7:
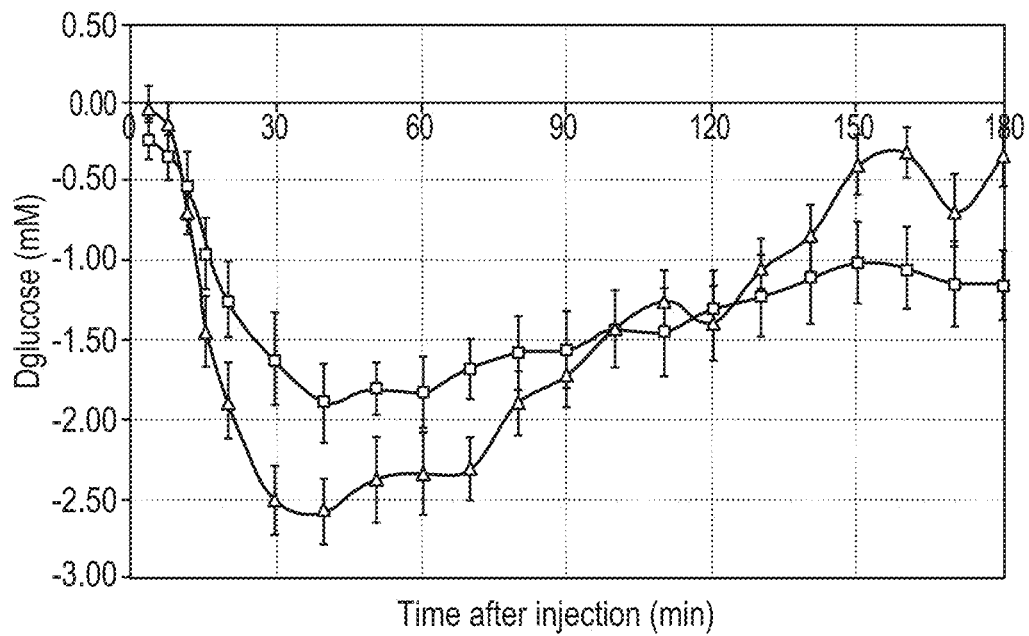

FIG. 7: DGlucose (mM) as a function of time after injection (min.). Curve plotted with the squares corresponding to example B3, glucose Tmin=61±31 min, curve plotted with the triangles corresponding to example B1, glucose Tmin=44±13 min.

Figure 8:
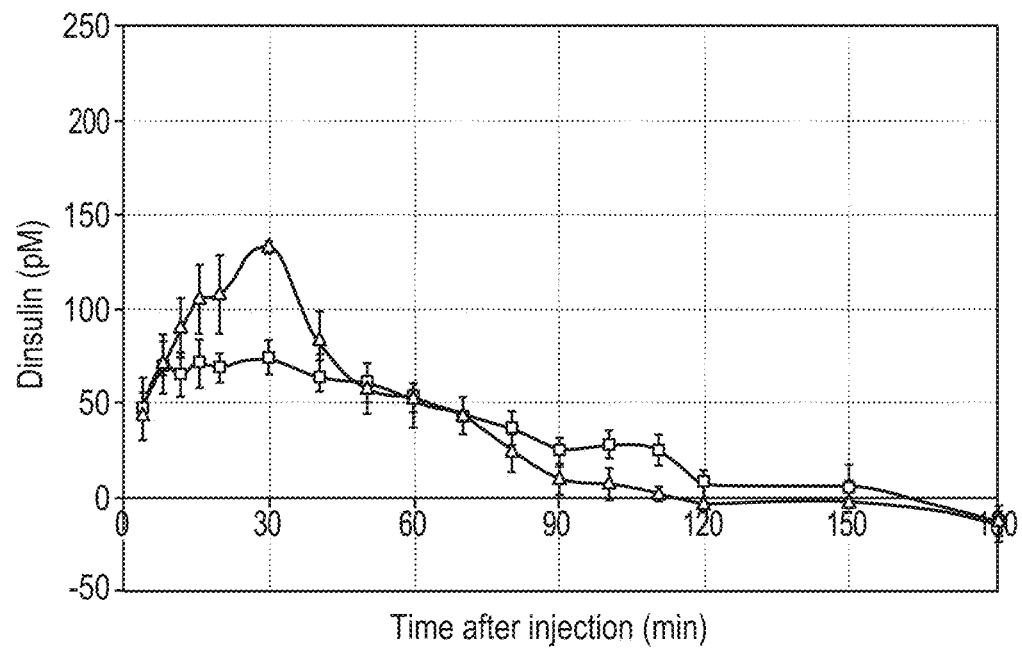

FIG. 8: DInsulin (pM) as a function of time after injection (min.). Curve plotted with the squares corresponding to example B3, insulin Tmax=36±33 min, curve plotted with the triangles corresponding to example B1, insulin Tmax=28±13 min.

Figure 9:
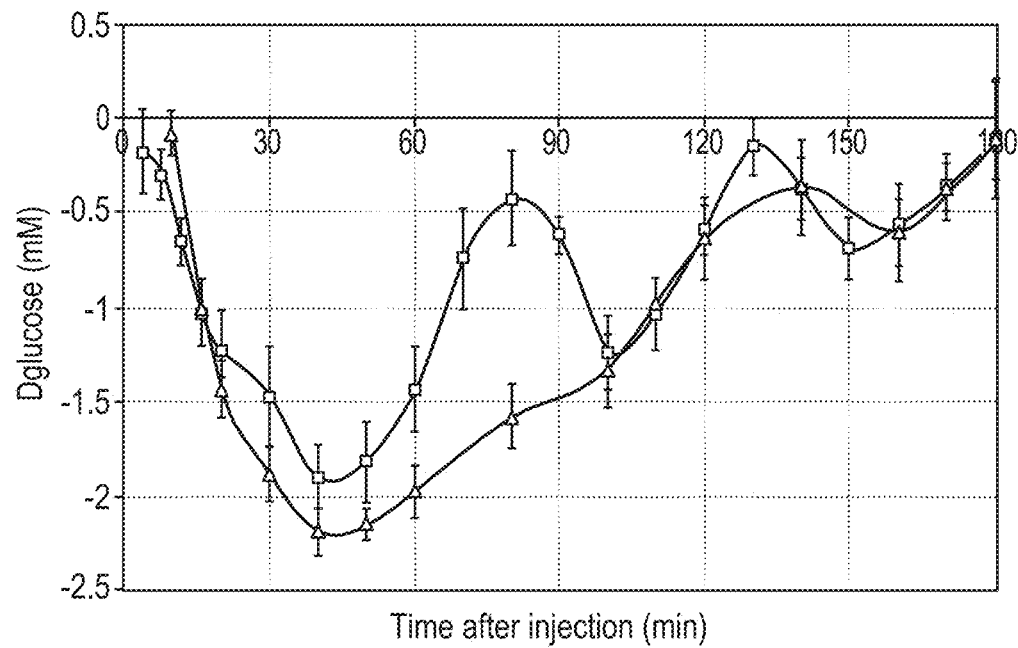

FIG. 9: DGlucose (mM) as a function of time after injection (min.). Curve plotted with the squares corresponding to example B39, glucose Tmin=46±9 min, curve plotted with the triangles corresponding to example B1, glucose Tmin=53±24 min.

Figure 10:
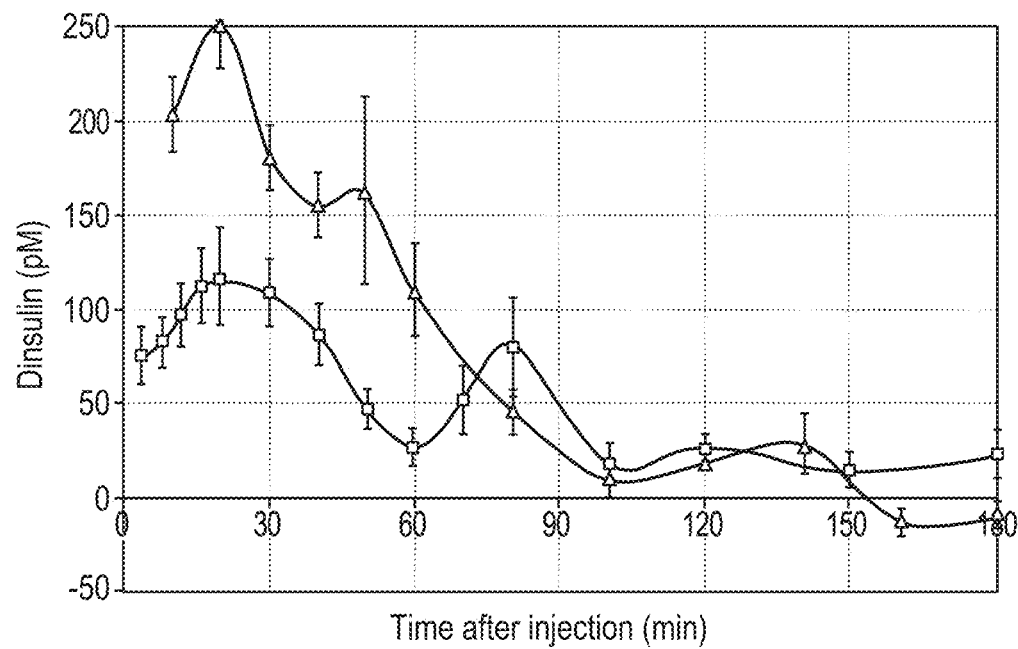

FIG. 10: DInsulin (pM) as a function of time after injection (min.). Curve plotted with the squares corresponding to example B39, insulin Tmax=20±7 min, curve plotted with the triangles corresponding to example B1, insulin Tmax=22±10 min.

Figure 11:
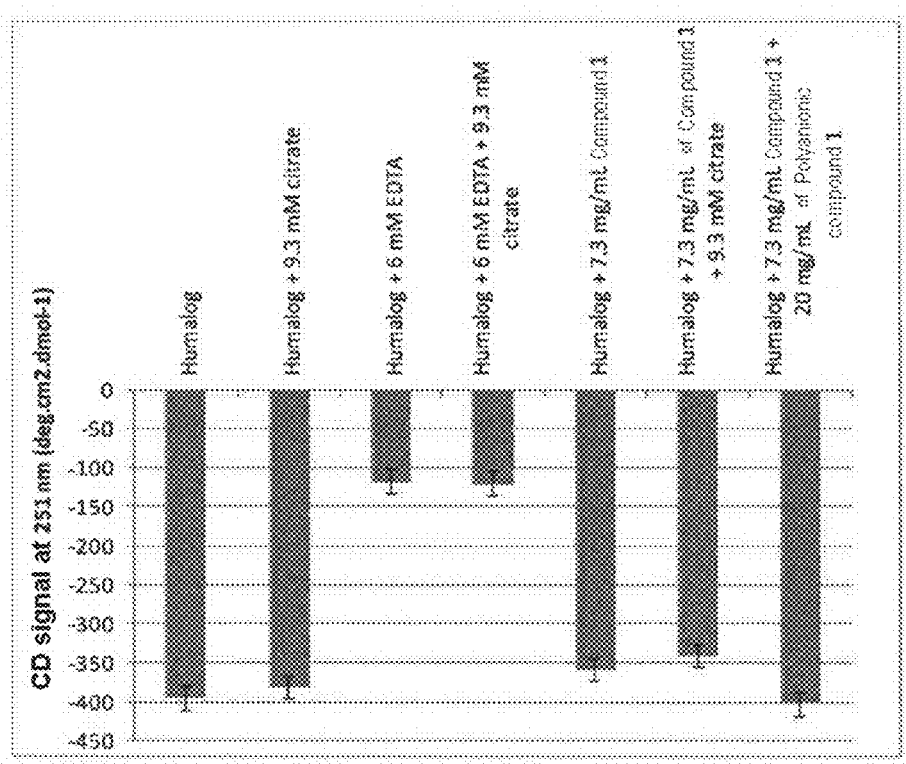

FIG. 11 describes on the x-axis, from left to right:
Humalog
Humalog+9.3 mM citrate
Humalog+6 mM EDTA
Humalog+6 mM EDTA+9.3 mM citrate
Humalog+7.3 mg/ml Compound 1
Humalog+7.3 mg/ml Compound 1+9.3 mM citrate
Humalog+7.3 mg/ml Compound 1+20 mg/ml Polyanionic compound 1 and on the y-axis the CD signal at 251 nm (deg·cm$^2$·dmol$^{-1}$).

Figure 12:
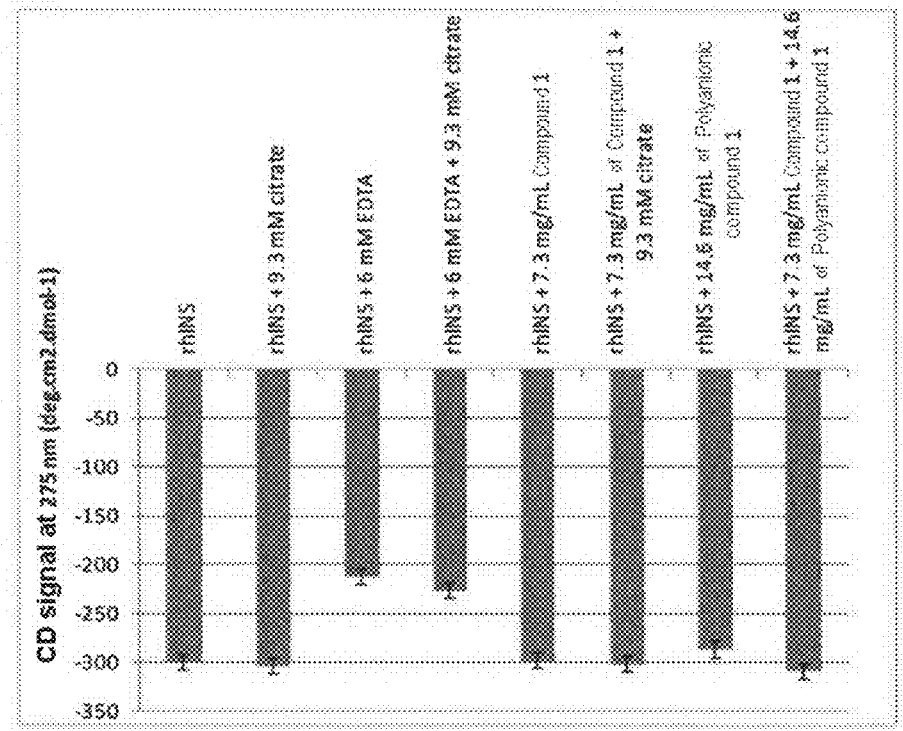

FIG. 12 describes on the x-axis, from left to right:
rhINS
rhINS+9.3 mM citrate
rhINS+6 mM EDTA
rhINS+6 mM EDTA+9.3 mM citrate
rhINS+7.3 mg/ml Compound 1
rhINS+7.3 mg/ml Compound 1+9.3 mM citrate
rhINS+7.3 mg/ml Compound 1+20 mg/ml Polyanionic compound 1 and on the y-axis the CD signal at 275 nm (deg·cm$^2$·dmol$^{-1}$).

Figure 13:
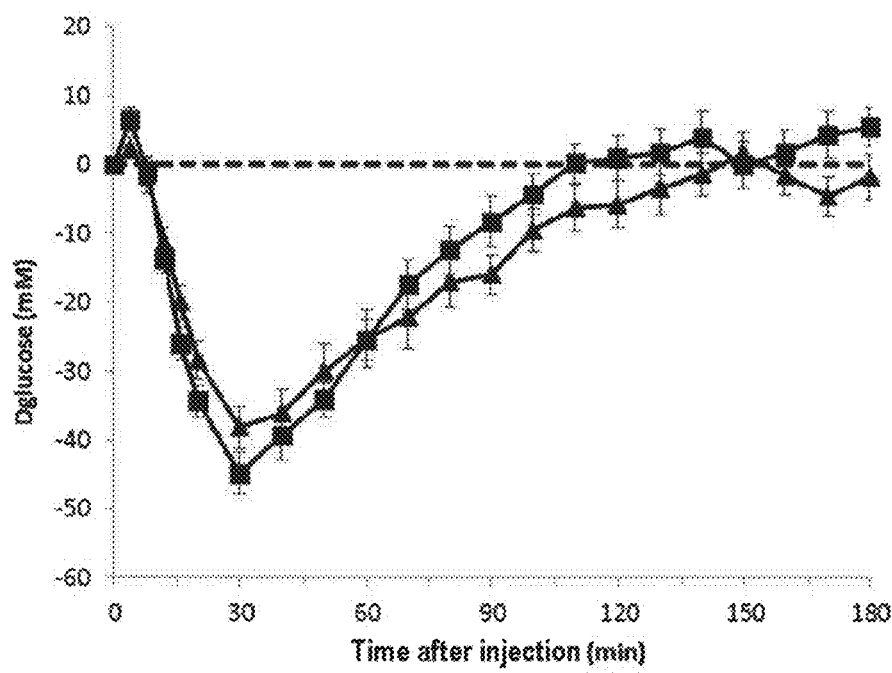

FIG. 13: DGlucose (mM) as a function of time after injection (min.). Curve plotted with the squares corresponding to example B11, glucose Tmin=32±10 min, curve plotted with the triangles corresponding to example B2, glucose Tmin=41±21 min.

Figure 14:
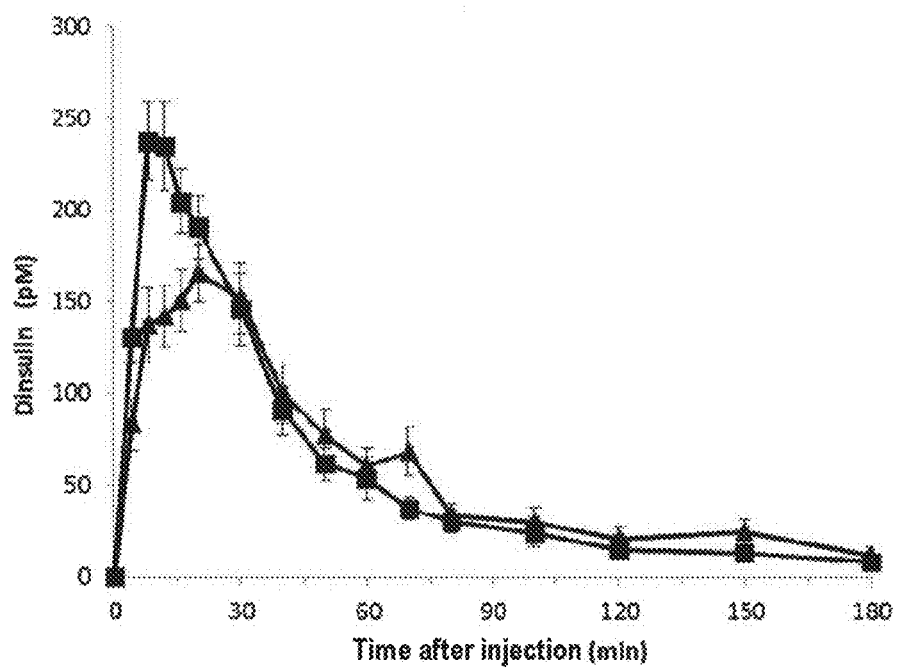

FIG. 14: DInsulin (pM) as a function of time after injection (min.). Curve plotted with the squares corresponding to example B11, insulin Tmax=13±5 min, curve plotted with the triangles corresponding to example B2, insulin Tmax=22±13 min.

Figure 15:
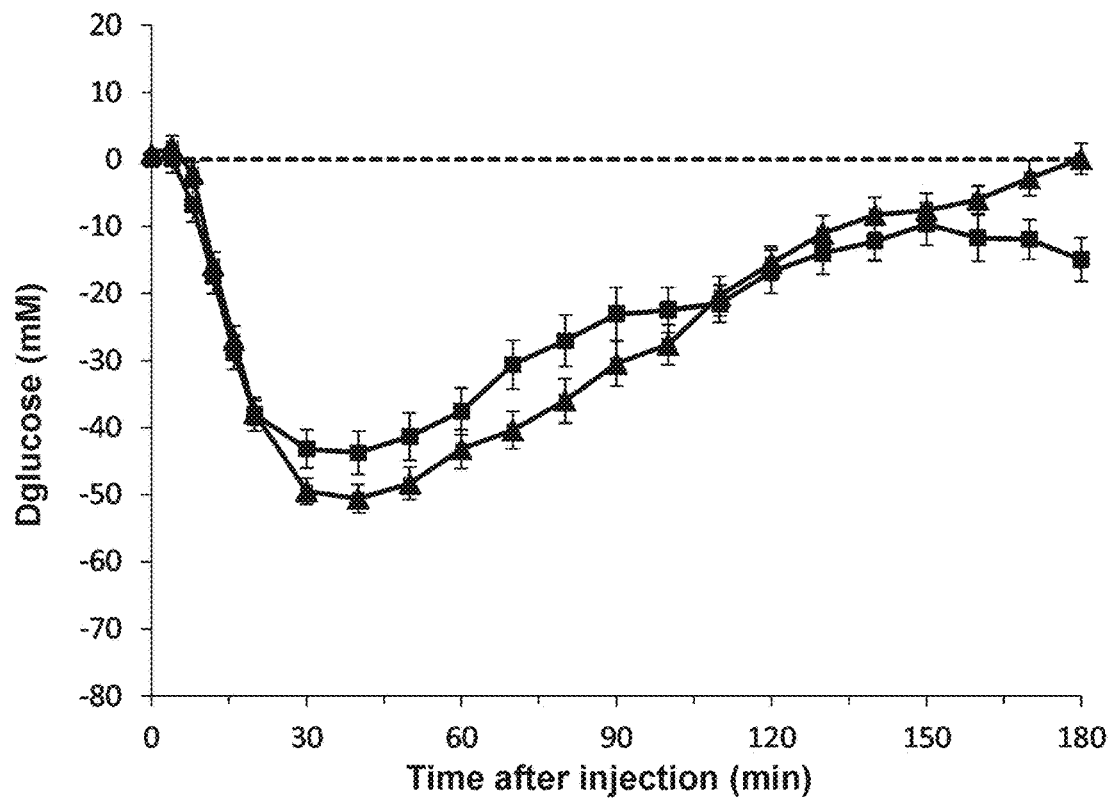

FIG. 15: DGlucose (mM) as a function of time after injection (min.). Curve plotted with the squares corresponding to example B102, glucose Tmin=47±30 min, curve plotted with the triangles corresponding to example B1, glucose Tmin=47±15 min.

Figure 16:
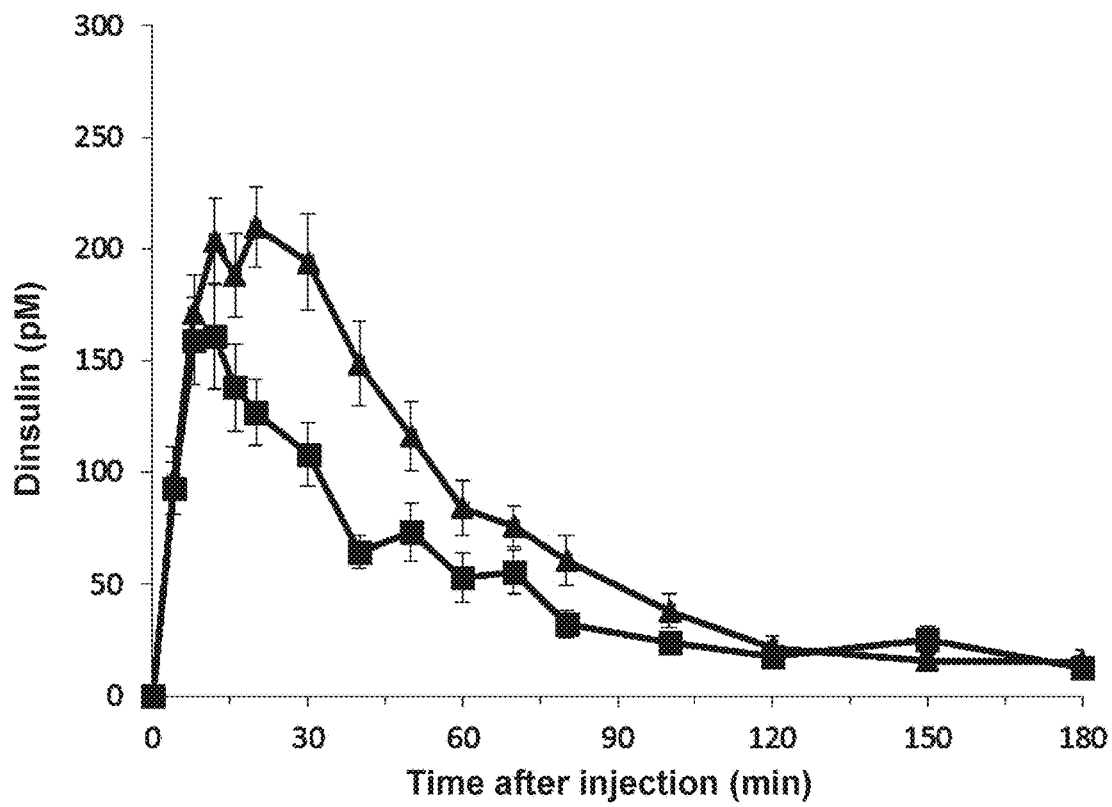

FIG. 16: DInsulin (pM) as a function of time after injection (min.). Curve plotted with the squares corresponding to example B38, insulin Tmax=22±21 min, curve plotted with the triangles corresponding to example B1, insulin Tmax=19±12 min.

Figure 17:
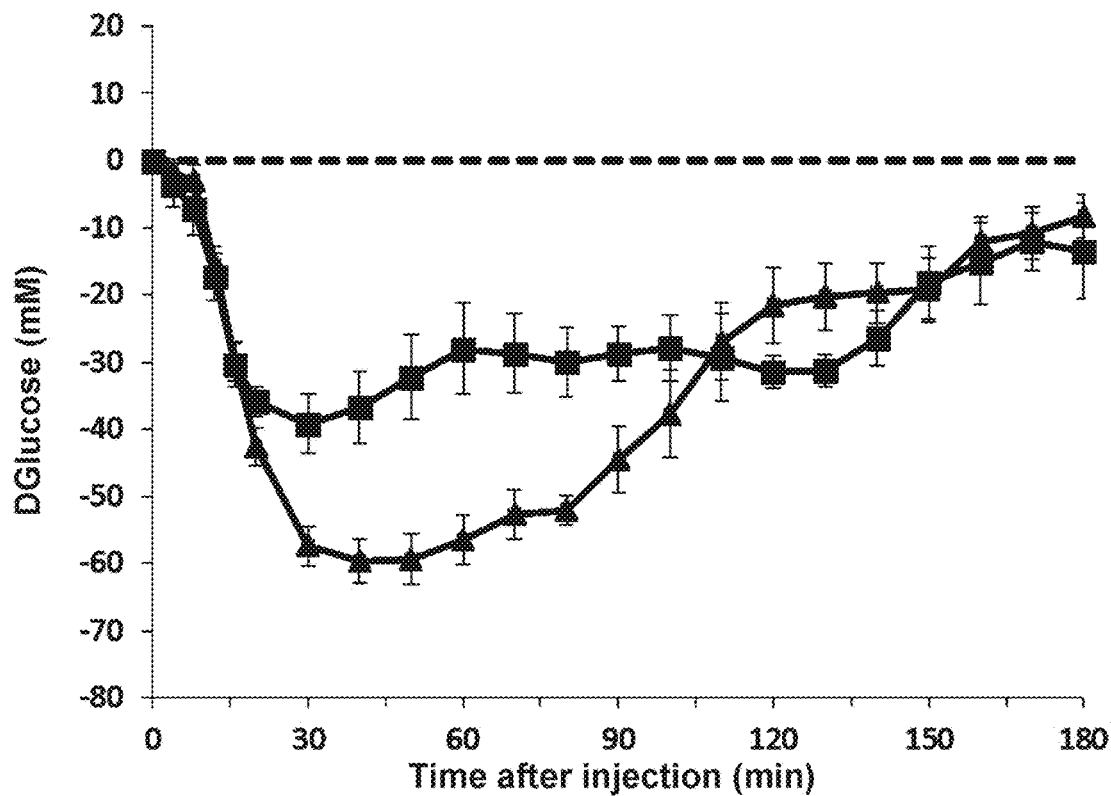

FIG. 17: DGlucose (mM) as a function of time after injection (min.). Curve plotted with the squares corresponding to example B53, glucose Tmin=63±36 min, curve plotted with the triangles corresponding to example B1, glucose Tmin=53±19 min.

Figure 18:
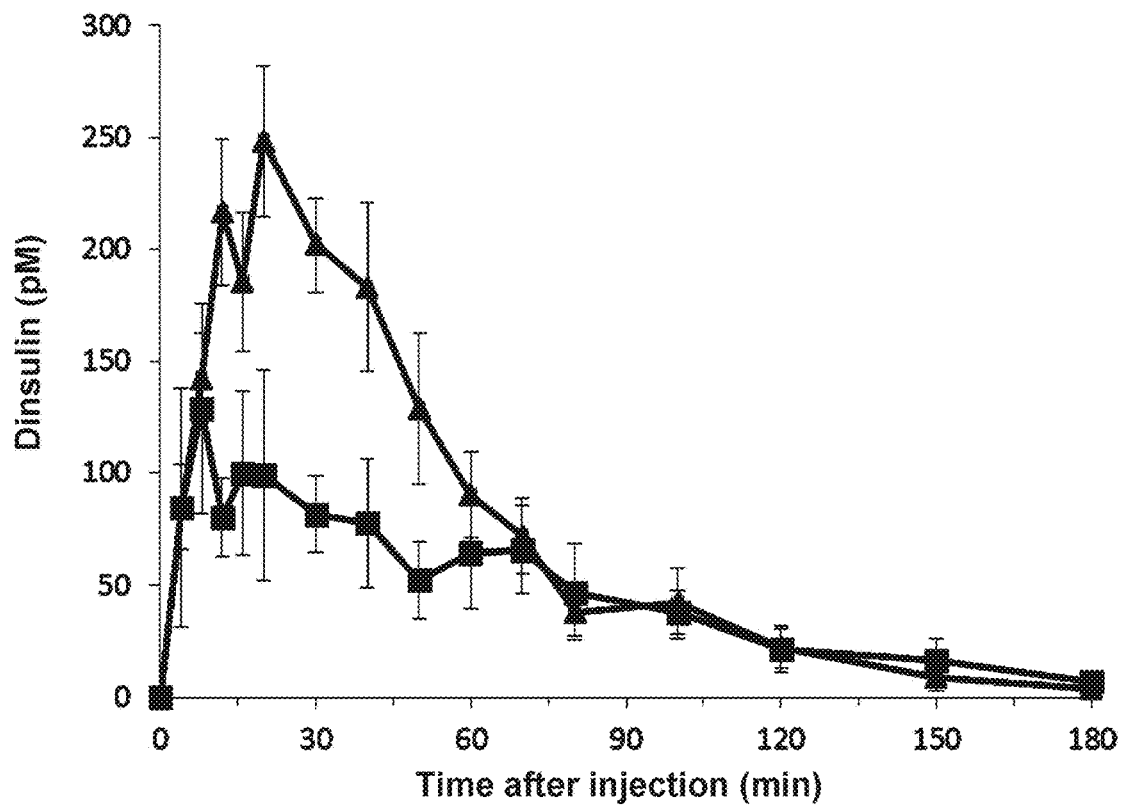

FIG. 18: DInsulin (pM) as a function of time after injection (min.). Curve plotted with the squares corresponding to example B53, insulin Tmax=19±12 min, curve plotted with the triangles corresponding to example B1, insulin Tmax=19±6 min.

Figure 19:
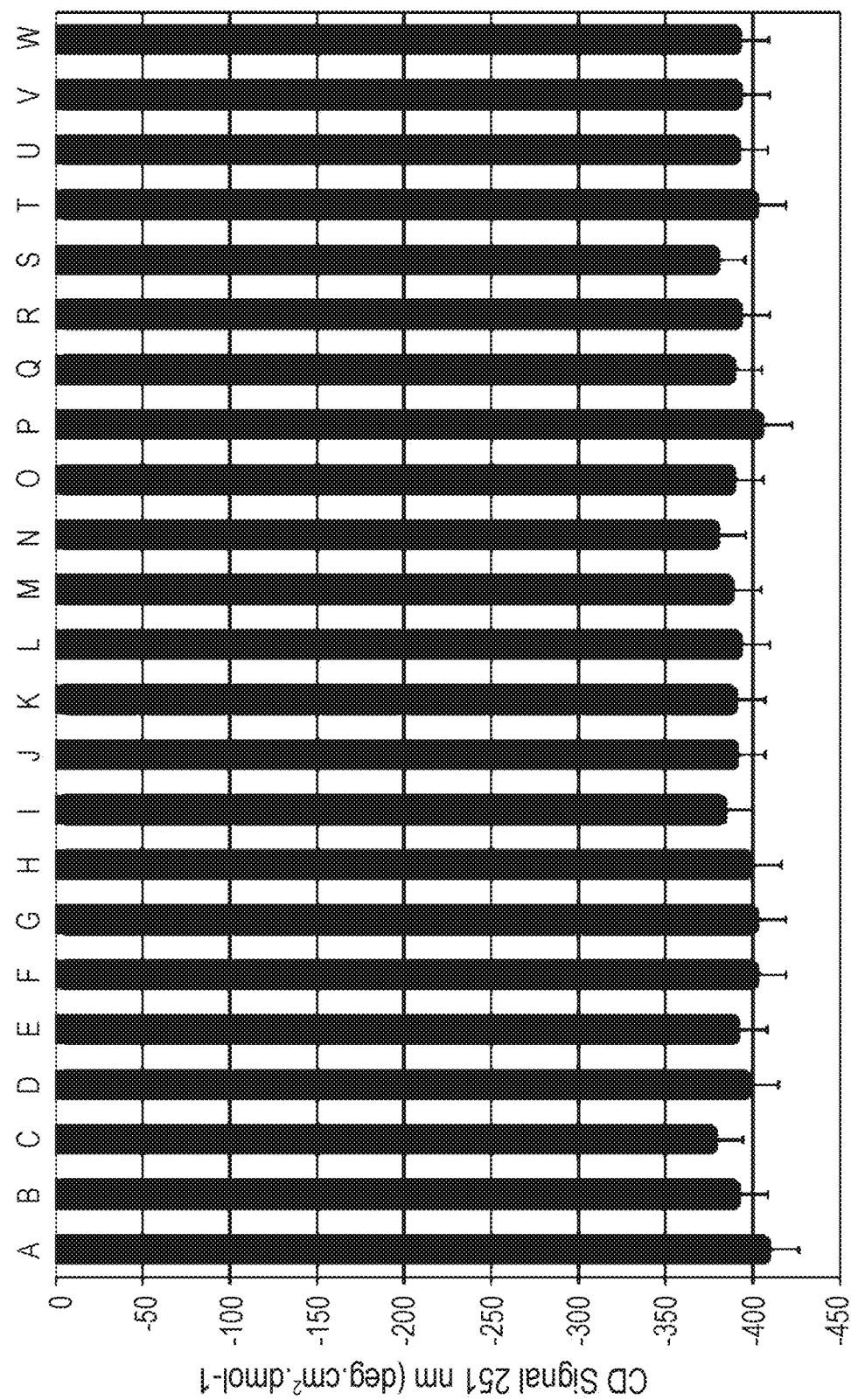

FIG. 19 describes on the x-axis:
A: lispro insulin (100 IU/mL)
B: lispro insulin+7.3 mg/mL of compound 2
C: lispro insulin+7.3 mg/mL of compound 2+citrate at 9.3 mM
D: lispro insulin+7.3 mg/mL of compound 1
E: lispro insulin+7.3 mg/mL of compound 1+citrate at 9.3 mM
F: lispro insulin+7.3 mg/mL of compound 3
G: lispro insulin+7.3 mg/mL of compound 3+citrate at 9.3 mM
H: lispro insulin+7.3 mg/mL of compound 4
I: lispro insulin+7.3 mg/mL of compound 4+citrate at 9.3 mM
J: lispro insulin+7.3 mg/mL of compound 5
K: lispro insulin+7.3 mg/mL of compound 5+citrate at 9.3 mM
L: lispro insulin+7.3 mg/mL of compound 6
M: lispro insulin+7.3 mg/mL of compound 6+citrate at 9.3 mM
N: lispro insulin+7.3 mg/mL of compound 7

O: lispro insulin+7.3 mg/mL of compound 7+citrate at 9.3 mM
P: lispro insulin+7.3 mg/mL of compound 8
Q: lispro insulin+7.3 mg/mL of compound 8+citrate at 9.3 mM
R: lispro insulin+7.3 mg/mL of compound 9
S: lispro insulin+7.3 mg/mL of compound 9+citrate at 9.3 mM
T: lispro insulin+7.3 mg/mL of compound 10
U: lispro insulin+7.3 mg/mL of compound 10+citrate at 9.3 mM
V: lispro insulin+7.3 mg/mL of compound 11
W: lispro insulin+7.3 mg/mL of compound 11+citrate at 9.3 mM and on the y-axis the circular dichroism signal at 251 nm (deg·cm$^2$·dmol$^{-1}$).

Figure 20:
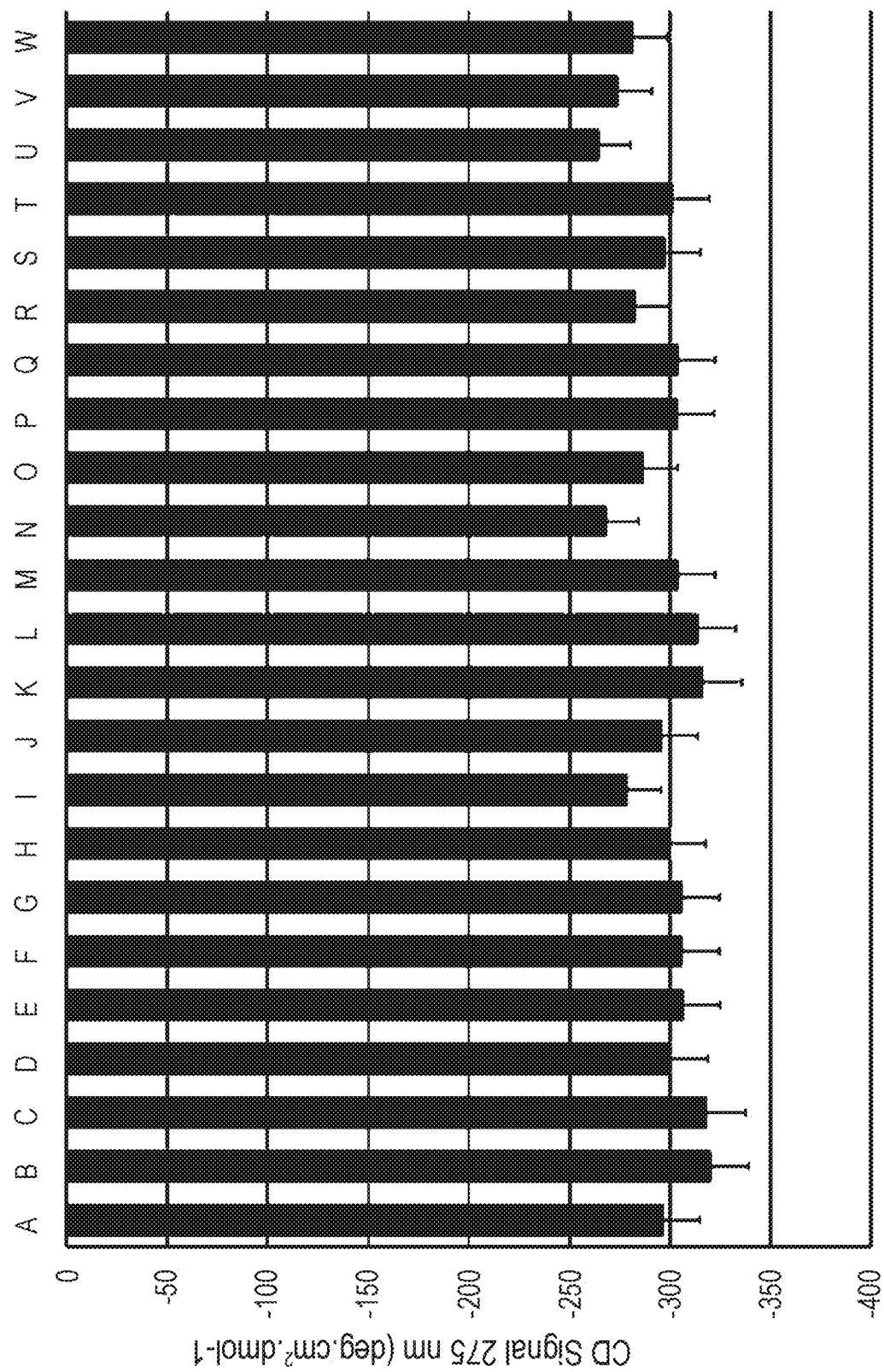

FIG. 20 describes on the x-axis:
A: human insulin (100 IU/mL)
B: human insulin+7.3 mg/mL of compound 2
C: human insulin+7.3 mg/mL of compound 2+citrate at 9.3 mM
D: human insulin+7.3 mg/mL of compound 1
E: human insulin+7.3 mg/mL of compound 1+citrate at 9.3 mM
F: human insulin+7.3 mg/mL of compound 3
G: human insulin+7.3 mg/mL of compound 3+citrate at 9.3 mM
H: human insulin+7.3 mg/mL of compound 4
I: human insulin+7.3 mg/mL of compound 4+citrate at 9.3 mM
J: human insulin+7.3 mg/mL of compound 5
K: human insulin+7.3 mg/mL of compound 5+citrate at 9.3 mM
L: human insulin+7.3 mg/mL of compound 6
M: human insulin+7.3 mg/mL of compound 6+citrate at 9.3 mM
N: human insulin+7.3 mg/mL of compound 7
O: human insulin+7.3 mg/mL of compound 7+citrate at 9.3 mM
P: human insulin+7.3 mg/mL of compound 8
Q: human insulin+7.3 mg/mL of compound 8+citrate at 9.3 mM
R: human insulin+7.3 mg/mL of compound 9
S: human insulin+7.3 mg/mL of compound 9+citrate at 9.3 mM
T: human insulin+7.3 mg/mL of compound 10
U: human insulin+7.3 mg/mL of compound 10+citrate at 9.3 mM
V: human insulin+7.3 mg/mL of compound 11
W: human insulin+7.3 mg/mL of compound 11+citrate at 9.3 mM and on the y-axis the circular dichroism signal at 275 nm (deg·cm$^2$·dmol$^{-1}$).

The invention consists of a composition, in aqueous solution, comprising insulin in hexameric form, at least one substituted anionic compound and a non-polymeric polyanionic compound.

The term "substituted anionic compound" means compounds consisting of a saccharide backbone formed from a discrete number u of between 1 and 8 (1≤u≤8) of identical or different saccharide units, linked via identical or different glycoside bonds, said saccharide units being chosen from the group consisting of hexoses, in cyclic form or in open reduced form, said compound comprising partially substituted carboxyl functional groups, the unsubstituted carboxyl functional groups being salifiable.

In one embodiment, the insulin is in hexameric form.
In one embodiment, the insulin is human insulin.
The term "human insulin" means an insulin obtained by synthesis or recombination, whose peptide sequence is the sequence of human insulin, including the allelic variations and homologs.

In one embodiment, the insulin is a recombinant human insulin as described in the European Pharmacopea and the American Pharmacopea.

In one embodiment, the insulin is an insulin analog.
The term "insulin analog" means a recombinant insulin whose primary sequence contains at least one modification relative to the primary sequence of human insulin.

In one embodiment, the insulin analog is chosen from the group consisting of the insulin lispro (Humalog®), the insulin aspart (Novolog®, Novorapid®) and the insulin glulisine (Apidra®).

In one embodiment, the insulin analog is the insulin lispro (Humalog®).

In one embodiment, the insulin analog is the insulin aspart (Novolog®, Novorapid®).

In one embodiment, the insulin analog is the insulin glulisine (Apidra®).

In one embodiment, the substituted anionic compound is chosen from substituted anionic compounds, in isolated form or as a mixture, consisting of a backbone formed from a discrete number u of between 1 and 8 (1≤u≤8) of identical or different saccharide units, linked via identical or different glycoside bonds, said saccharide units being chosen from the group consisting of hexoses, in cyclic form or in open reduced form, characterized in that they are substituted with:

a) at least one substituent of general formula I:

$$—[R_1]_a-[AA]_m \quad \text{Formula I}$$

the substituents being identical or different when there are at least two substituents, in which:
the radical -[AA] denotes an amino acid residue,
the radical —R$_1$— being:
  either a bond and then a=0 and the amino acid residue -[AA] is directly linked to the backbone via a function G,
  or a C2 to C15 carbon-based chain, and then a=1, optionally substituted and/or comprising at least one heteroatom chosen from O, N and S and at least one acid function before the reaction with the amino acid, said chain forming with the amino acid residue -[AA] an amide function, and is attached to the backbone by means of a function F resulting from a reaction between a hydroxyl function borne by the backbone and a function or substituent borne by the precursor of the radical —R$_1$—,
F is a function chosen from ether, ester and carbamate functions,
G is a carbamate function,
m is equal to 1 or 2,
the degree of substitution of the saccharide units, j, in —[R$_1$]$_a$-[AA]$_m$ being strictly greater than 0 and less than or equal to 6, 0<j≤6 b) and, optionally, one or more substituents —R'$_1$,
the substituent —R'$_1$ being a C2 to C15 carbon-based chain, which is optionally substituted and/or comprising at least one heteroatom chosen from O, N and S and at least one acid function in the form of an alkali metal cation salt, said chain being linked to the backbone via a function F' resulting from a reaction between a hydroxyl function borne by the backbone and a function or substituent borne by the precursor of the substituent —R'$_1$, F' is an ether, ester or carbamate function,
the degree of substitution of the saccharide units, i, in —R'$_1$, being between 0 and 6–j, 0≤i≤6–j, and
F and F' are identical or different,
F and G are identical or different,
i+j≤6,
—R'$_1$ is identical to or different from —R$_1$—,
the free salifiable acid functions borne by the substituent —R'$_1$ are in the form of alkali metal cation salts,
said glycoside bonds, which may be identical or different, being chosen from the group consisting of glycoside bonds of (1,1), (1,2), (1,3), (1,4) or (1,6) type, in an alpha or beta geometry.

In one embodiment, the substituted anionic compound, in isolated form or as a mixture, is chosen from substituted anionic compounds consisting of a saccharide backbone formed from a discrete number u of between 1 and 8 (1≤u≤8) of identical or different saccharide units, linked via identical or different glycoside bonds, said saccharide units being chosen from hexoses, in cyclic form or in open reduced form, characterized a) in that they are randomly substituted with:
at least one substituent of general formula I:

 Formula I the substituents being identical or different when there are at least two substituents, in which:
the radical -[AA]- denotes an amino acid residue, said amino acid being chosen from the group consisting of phenylalanine, alpha-methylphenylalanine, 3,4-dihydroxyphenylalanine, tyrosine, alpha-methyltyrosine, O-methyltyrosine, alpha-phenylglycine, 4-hydroxyphenylglycine and 3,5-dihydroxyphenylglycine, and the alkali metal cation salts thereof, said derivatives being of L or D absolute configuration, -[AA] is attached to the backbone of the molecule via a linker arm —R$_1$— or directly linked to the backbone via a function G,
—R$_1$— being:
either a bond G, and then a=0,
or a C2 to C15 carbon-based chain, and then a=1, which is optionally substituted and/or comprising at least one heteroatom chosen from O, N and S and bearing at least one acid function before the reaction with the amino acid, said chain forming with the amino acid residue -[AA] an amide bond, and is attached to the saccharide backbone via a function F resulting from a reaction between a hydroxyl function borne by the backbone and a function borne by the precursor of R$_1$,
F is an ether, ester or carbamate function,
G is a carbamate function,
m is equal to 1 or 2,
the degree of substitution, j, in —[R$_1$]$_a$-[AA]$_m$ being strictly greater than 0 and less than or equal to 6, 0<j≤6, and, optionally,
one or more substituents —R'$_1$
—R'$_1$ being a C2 to C15 carbon-based chain, which is optionally substituted and/or comprising at least one heteroatom (such as O, N and S) and bearing at least one acid function in the form of an alkali metal cation salt, said chain being attached to the saccharide backbone via a function F' resulting from a reaction between a hydroxyl function borne by the backbone and a function borne by the precursor of —R'$_1$,
F' is an ether, ester or carbamate function,
the degree of substitution, i, in —R'$_1$, being between 0 and 6–j, 0≤i≤6–j, and
—R'$_1$— is identical to or different from —R$_1$,
F and F' are identical or different,
F' and G are identical or different,
the free salifiable acid functions are in the form of alkali metal cation salts,
b) said glycoside bonds, which may be identical or different, being chosen from the group consisting of glycoside bonds of (1,1), (1,2), (1,3), (1,4) or (1,6) type, in an alpha or beta geometry,
c) i+j≤6.

In one embodiment, m is equal to 1.
In one embodiment, —R$_1$ and —R'$_1$, which may be identical or different, are a C2 to C8 carbon-based chain.
In one embodiment, —R$_1$ and —R'$_1$, which may be identical or different, are a C2 to C4 carbon-based chain.
i and j are statistical degrees of substitution and represent the mean number of substituents per saccharide unit. Since each saccharide unit bears several hydroxyl functions of different reactivity, the distribution of the substituents on the substituted anionic compounds may be different from one saccharide unit to another within the same polyanionic compound.

In one embodiment, 0.3≤i.
In one embodiment, 0.4≤i.
In one embodiment, i≤3.
In one embodiment, i≤2.5.
In one embodiment, 0.3≤j.
In one embodiment, 0.4≤j.
In one embodiment, j≤2.
In one embodiment, j≤1.8.
In one embodiment, i and j are such that 0<i+j≤6.
In one embodiment, 0<i+j≤5.
In one embodiment, 0<i+j≤4.
In one embodiment, 0<i+j≤3.
In one embodiment, 0<i+j≤2.5.
In one embodiment, 0<i+j≤2.
In one embodiment, 0.5≤i+j≤3.
In one embodiment, 0.5≤i+j≤2.5.
In one embodiment, 0.5≤i+j≤2.
In one embodiment, 0.6≤i+j≤3.5.
In one embodiment, 0.8≤i+j≤2.5.
In one embodiment, 0.7≤i+j≤2.5.
In one embodiment, 0.7≤i+j≤2.
In one embodiment, 1<i+j≤2.5.
In one embodiment, 1<i+j≤2.
In one embodiment, —R1 and —R'1 are attached to the backbone via an ether bond.
In one embodiment, when —R1- is a carbon-based chain, it is directly attached to the backbone via an ether bond.
In one embodiment, when —R1- is a carbon-based chain, it optionally comprises a heteroatom chosen from the group consisting of O, N and S.
In one embodiment, —R1- forms with the amino acid residue AA an amide bond, and is directly attached to the backbone via an ether function F.
In one embodiment, —R1- forms with the amino acid residue AA an amide bond, and is directly attached to the backbone via a carbamate function F.
In one embodiment, —R1- forms with the amino acid residue AA an amide bond, and is directly attached to the backbone via an ester function F.
In one embodiment, —R1- and —R'1 are chosen from radicals of formulae II and III Formula II

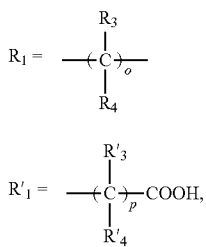

Formula III

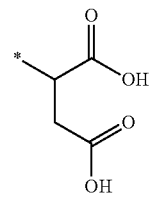

in which:
o and p, which may be identical or different, are greater than or equal to 1 and less than or equal to 12, and
—$R_3$, —$R'_3$, —$R_4$ and —$R'_4$, which may be identical or different, are chosen from the group consisting of a hydrogen atom, a saturated or unsaturated, linear, branched or cyclic C1 to C6 alkyl, a benzyl, a C7 to C10 alkylaryl and optionally comprising heteroatoms chosen from the group consisting of O, N and/or S, or functions chosen from the group consisting of carboxylic acid, amine, alcohol and thiol functions.

In one embodiment, —R1- before attachment to -AA-, is —$CH_2$—COOH.

In one embodiment, the substituted anionic compounds according to the invention are characterized in that the radical —R'1 is —$CH_2$—COOH.

In one embodiment, —R1- before optional attachment to -AA-, is derived from citric acid.

In one embodiment, —R1- before optional attachment to -AA-, is derived from malic acid.

In one embodiment, —R'1 is derived from citric acid.

In one embodiment, —R'1 is derived from malic acid.

In one embodiment, —R1-, before attachment to -AA-, is chosen from the following groups, in which * represents the site of attachment to F:

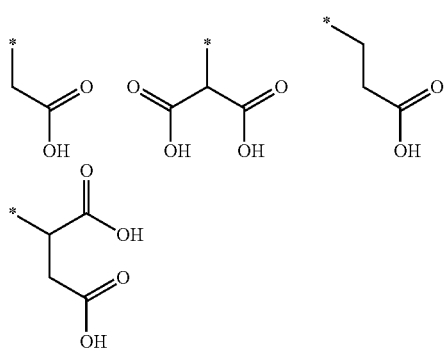

or the salts thereof with alkali metal cations chosen from the group consisting of $Na^+$ and $K^+$.

In one embodiment, —$R'_1$ is chosen from the following groups, in which * represents the site of attachment to F:

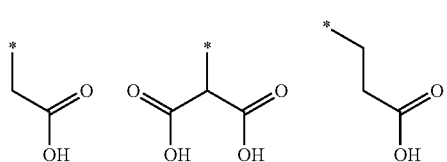

or the salts thereof with alkali metal cations chosen from the group consisting of $Na^+$ and $K^+$.

In one embodiment, the radical -[AA] is a residue of phenylalanine and of alkali metal cation salts thereof of L, D or racemic absolute configuration.

In one embodiment, the radical -[AA] is a residue of alpha-methylphenylalanine and of alkali metal cation salts thereof of L, D or racemic absolute configuration.

In one embodiment, the radical -[AA] is a residue of 3,4-dihydroxyphenylalanine and of alkali metal cation salts thereof of L, D or racemic absolute configuration.

In one embodiment, the radical -[AA] is a residue of tyrosine and of alkali metal cation salts thereof of L, D or racemic absolute configuration.

In one embodiment, the radical -[AA] is a residue of alpha-methyltyrosine and of alkali metal cation salts thereof of L, D or racemic absolute configuration.

In one embodiment, the radical -[AA] is a residue of O-methyltyrosine and of alkali metal cation salts thereof of L, D or racemic absolute configuration.

In one embodiment, the radical -[AA] is a residue of alpha-phenylglycine and of alkali metal cation salts thereof of L, D or racemic absolute configuration.

In one embodiment, the radical -[AA] is a residue of 4-hydroxyphenylglycine and of alkali metal cation salts thereof of L, D or racemic absolute configuration.

In one embodiment, the radical -[AA] is a residue of 3,5-dihydroxyphenylglycine and of alkali metal cation salts thereof of L, D or racemic absolute configuration.

In one embodiment, the radical -[AA] is an amino acid residue in the form of a racemic mixture.

In one embodiment, the radical -[AA] is an amino acid residue in the form of isolated isomers of D absolute configuration.

In one embodiment, the radical -[AA] is an amino acid residue in the form of isolated isomers of L absolute configuration.

In one embodiment, u is between 1 and 5.
In one embodiment, u is between 3 and 5.
In one embodiment, u=8.
In one embodiment, u=7.
In one embodiment, u=6.
In one embodiment, u=5.
In one embodiment, u=4.
In one embodiment, u=3.
In one embodiment, u=2.
In one embodiment, u=1.

In one embodiment, hexoses are chosen from the group consisting of mannose, glucose, fructose, sorbose, tagatose, psicose, galactose, allose, altrose, talose, idose, gulose, fucose, fuculose, rhamnose, mannitol, sorbitol and galactitol (dulcitol).

In one embodiment, the glycoside bonds are of (1,4) or (1,6) type.

In one embodiment, the substituted anionic compound is chosen from anionic compounds consisting of a saccharide backbone formed from a discrete number u=2 of identical or different saccharide units chosen from hexoses linked via a glycoside bond of (1,1) type.

In one embodiment, the substituted anionic compound is chosen from anionic compounds consisting of a saccharide backbone formed from a discrete number u=2 of different saccharide units chosen from hexoses and linked via a glycoside bond of (1,1) type, said saccharide backbone being chosen from the group consisting of trehalose and sucrose.

In one embodiment, the substituted anionic compound is chosen from anionic compounds consisting of a saccharide backbone formed from a discrete number u=2 of identical or different saccharide units chosen from hexoses linked via a glycoside bond of (1,2) type.

In one embodiment, the substituted anionic compound is chosen from anionic compounds consisting of a saccharide backbone formed from a discrete number u=2 of identical or different saccharide units chosen from hexoses linked via a glycoside bond of (1,2) type, said saccharide backbone being kojibiose.

In one embodiment, the substituted anionic compound is chosen from anionic compounds consisting of a saccharide backbone formed from a discrete number u=2 of identical or different saccharide units chosen from hexoses linked via a glycoside bond of (1,3) type.

In one embodiment, the substituted anionic compound is chosen from anionic compounds consisting of a saccharide backbone formed from a discrete number u=2 of identical or different saccharide units chosen from hexoses linked via a glycoside bond of (1,3) type, said saccharide backbone being chosen from the group consisting of nigeriose and laminaribiose.

In one embodiment, the substituted anionic compound is chosen from anionic compounds consisting of a saccharide backbone formed from a discrete number u=2 of identical or different saccharide units chosen from hexoses linked via a glycoside bond of (1,4) type.

In one embodiment, the substituted anionic compound is chosen from anionic compounds consisting of a saccharide backbone formed from a discrete number u=2 of identical or different saccharide units chosen from hexoses linked via a glycoside bond of (1,4) type, said saccharide backbone being chosen from the group consisting of maltose, lactose and cellobiose.

In one embodiment, the substituted anionic compound is chosen from anionic compounds consisting of a saccharide backbone formed from a discrete number u=2 of identical or different saccharide units chosen from hexoses linked via a glycoside bond of (1,6) type.

In one embodiment, the substituted anionic compound is chosen from anionic compounds consisting of a saccharide backbone formed from a discrete number u=2 of identical or different saccharide units chosen from hexoses linked via a glycoside bond of (1,6) type, said saccharide backbone being chosen from the group consisting of isomaltose, melibiose and gentiobiose.

In one embodiment, the substituted anionic compound is chosen from anionic compounds consisting of a saccharide backbone formed from a discrete number u=2 of identical or different saccharide units chosen from hexoses linked via a glycoside bond of (1,6) type, said saccharide backbone being isomaltose.

In one embodiment, the substituted anionic compound is chosen from anionic compounds consisting of a saccharide backbone formed from a discrete number u=2 of saccharide units, one of which is in cyclic form and the other in open reduced form.

In one embodiment, the substituted anionic compound is chosen from anionic compounds consisting of a saccharide backbone formed from a discrete number u=2 of saccharide units, one of which is in cyclic form and the other in open reduced form, said saccharide backbone being chosen from the group consisting of maltitol and isomaltitol.

In one embodiment, the substituted anionic compound according to the invention is characterized in that the saccharide backbone is formed from a discrete number $3 \leq u \leq 8$ of identical or different saccharide units.

In one embodiment, the substituted anionic compound according to the invention is characterized in that at least one of the identical or different saccharide units, of which the saccharide backbone formed from a discrete number $3 \leq u \leq 8$ of saccharide units is composed, is chosen from the group consisting of hexose units linked via identical or different glycoside bonds.

In one embodiment, the substituted anionic compound according to the invention is characterized in that the identical or different saccharide units, of which the saccharide backbone formed from a discrete number $3 \leq u \leq 8$ of saccharide units is composed, are chosen from hexoses and linked via at least one glycoside bond of (1,2) type.

In one embodiment, the substituted anionic compound according to the invention is characterized in that the identical or different saccharide units, of which the saccharide backbone formed from a discrete number $3 \leq u \leq 8$ of saccharide units is composed, are chosen from hexoses and linked via at least one glycoside bond of (1,3) type.

In one embodiment, the substituted anionic compound according to the invention is characterized in that the identical or different saccharide units, of which the saccharide backbone formed from a discrete number $3 \leq u \leq 8$ of saccharide units is composed, are chosen from hexoses and linked via at least one glycoside bond of (1,4) type.

In one embodiment, the substituted anionic compound according to the invention is characterized in that the identical or different saccharide units, of which the saccharide backbone formed from a discrete number $3 \leq u \leq 8$ of saccharide units is composed, are chosen from hexoses and linked via at least one glycoside bond of (1,6) type.

In one embodiment, the substituted anionic compound according to the invention is characterized in that the saccharide backbone is formed from a discrete number u=3 of identical or different saccharide units.

In one embodiment, the substituted anionic compound according to the invention is characterized in that it comprises at least one saccharide unit chosen from the group consisting of hexoses in cyclic form and at least one saccharide unit chosen from the group consisting of hexoses in open form.

In one embodiment, the substituted anionic compound according to the invention is characterized in that the three saccharide units are identical.

In one embodiment, the substituted anionic compound according to the invention is characterized in that two of the three saccharide units are identical.

In one embodiment, the substituted anionic compound according to the invention is characterized in that the identical saccharide units are chosen from hexoses, two of which are in cyclic form and one is in open reduced form, and linked via glycoside bonds of (1,4) type.

In one embodiment, the substituted anionic compound according to the invention is characterized in that the identical saccharide units are chosen from hexoses, two of which are in cyclic form and one is in open reduced form, and linked via glycoside bonds of (1,6) type.

In one embodiment, the substituted anionic compound according to the invention is characterized in that the identical or different saccharide units are chosen from hexoses and in that the central hexose is linked via a glycoside bond of (1,2) type and via a glycoside bond of (1,4) type.

In one embodiment, the substituted anionic compound according to the invention is characterized in that the identical or different saccharide units are chosen from hexoses and in that the central hexose is linked via a glycoside bond of (1,3) type and via a glycoside bond of (1,4) type.

In one embodiment, the substituted anionic compound according to the invention is characterized in that the identical or different saccharide units are chosen from hexoses and in that the central hexose is linked via a glycoside bond of (1,2) type and via a glycoside bond of (1,6) type.

In one embodiment, the substituted anionic compound according to the invention is characterized in that the identical or different saccharide units are chosen from hexoses and in that the central hexose is linked via a glycoside bond of (1,2) type and via a glycoside bond of (1,3) type.

In one embodiment, the substituted anionic compound according to the invention is characterized in that the identical or different saccharide units are chosen from hexoses and in that the central hexose is linked via a glycoside bond of (1,4) type and via a glycoside bond of (1,6) type.

In one embodiment, the substituted anionic compound according to the invention is characterized in that the saccharide backbone is erlose.

In one embodiment, the substituted anionic compound according to the invention is characterized in that the three identical or different saccharide units are hexose units chosen from the group consisting of mannose and glucose.

In one embodiment, the substituted anionic compound according to the invention is characterized in that the saccharide backbone is maltotriose.

In one embodiment, the substituted anionic compound according to the invention is characterized in that the saccharide backbone is isomaltotriose.

In one embodiment, the substituted anionic compound according to the invention is characterized in that the saccharide backbone is formed from a discrete number u=4 of identical or different saccharide units.

In one embodiment, the substituted anionic compound according to the invention is characterized in that the four saccharide units are identical.

In one embodiment, the substituted anionic compound according to the invention is characterized in that three of the four saccharide units are identical.

In one embodiment, the substituted anionic compound according to the invention is characterized in that the four saccharide units are hexose units chosen from the group consisting of mannose and glucose.

In one embodiment, the substituted anionic compound according to the invention is characterized in that the saccharide backbone is maltotetraose.

In one embodiment, the substituted anionic compound according to the invention is characterized in that the identical or different saccharide units are chosen from hexoses and in that a terminal hexose is linked via a glycoside bond of (1,2) type and in that the others are linked together via a glycoside bond of (1,6) type.

In one embodiment, the substituted anionic compound according to the invention is characterized in that the identical or different saccharide units are chosen from hexoses and linked via a glycoside bond of (1,6) type.

In one embodiment, the substituted anionic compound according to the invention is characterized in that the saccharide backbone is formed from a discrete number u=5 of identical or different saccharide units.

In one embodiment, the substituted anionic compound according to the invention is characterized in that the five saccharide units are identical.

In one embodiment, the substituted anionic compound according to the invention is characterized in that the five saccharide units are hexose units chosen from the group consisting of mannose and glucose.

In one embodiment, the substituted anionic compound according to the invention is characterized in that the identical or different saccharide units are chosen from hexoses and linked via a glycoside bond of (1,4) type.

In one embodiment, the substituted anionic compound according to the invention is characterized in that the saccharide backbone is maltopentaose.

In one embodiment, the substituted anionic compound according to the invention is characterized in that the saccharide backbone is formed from a discrete number u=6 of identical or different saccharide units.

In one embodiment, the substituted anionic compound according to the invention is characterized in that the six saccharide units are identical.

In one embodiment, the substituted anionic compound according to the invention is characterized in that the identical or different saccharide units are chosen from hexoses and linked via a glycoside bond of (1,4) type.

In one embodiment, the substituted anionic compound according to the invention is characterized in that the six identical or different saccharide units are hexose units chosen from the group consisting of mannose and glucose.

In one embodiment, the substituted anionic compound according to the invention is characterized in that the saccharide backbone is maltohexaose.

In one embodiment, the substituted anionic compound according to the invention is characterized in that the saccharide backbone is formed from a discrete number u=7 of identical or different saccharide units.

In one embodiment, the substituted anionic compound according to the invention is characterized in that the seven saccharide units are identical.

In one embodiment, the substituted anionic compound according to the invention is characterized in that the identical or different saccharide units are chosen from hexoses and linked via a glycoside bond of (1,4) type.

In one embodiment, the substituted anionic compound according to the invention is characterized in that the seven saccharide units are hexose units chosen from the group consisting of mannose and glucose.

In one embodiment, the substituted anionic compound according to the invention is characterized in that the saccharide backbone is maltoheptaose.

In one embodiment, the substituted anionic compound according to the invention is characterized in that the saccharide backbone is formed from a discrete number u=8 of identical or different saccharide units.

In one embodiment, the substituted anionic compound according to the invention is characterized in that the eight saccharide units are identical.

In one embodiment, the substituted anionic compound according to the invention is characterized in that the identical or different saccharide units are chosen from hexoses and linked via a glycoside bond of (1,4) type.

In one embodiment, the substituted anionic compound according to the invention is characterized in that the eight saccharide units are hexose units chosen from the group consisting of mannose and glucose.

In one embodiment, the substituted anionic compound according to the invention is characterized in that the saccharide backbone is maltooctaose.

In one embodiment, the substituted anionic compound comprising a discrete number of saccharide units is a natural compound.

In one embodiment, the substituted anionic compound comprising a discrete number of saccharide units is a synthetic compound.

In one embodiment, the substituted anionic compound according to the invention is characterized in that it is obtained by enzymatic degradation of a polysaccharide followed by purification.

In one embodiment, the substituted anionic compound according to the invention is characterized in that it is obtained by chemical degradation of a polysaccharide followed by purification.

In one embodiment, the substituted anionic compound according to the invention is characterized in that it is obtained chemically, by covalent coupling of precursors of lower molecular weight.

In one embodiment, the substituted anionic compound according to the invention is characterized in that the saccharide backbone is sophorose.

In one embodiment, the substituted anionic compound according to the invention is characterized in that the saccharide backbone is sucrose.

In one embodiment, the substituted anionic compound according to the invention is characterized in that the saccharide backbone is lactulose.

In one embodiment, the substituted anionic compound according to the invention is characterized in that the saccharide backbone is maltulose.

In one embodiment, the substituted anionic compound according to the invention is characterized in that the saccharide backbone is leucrose.

In one embodiment, the substituted anionic compound according to the invention is characterized in that the saccharide backbone is rutinose.

In one embodiment, the substituted anionic compound according to the invention is characterized in that the saccharide backbone is isomaltulose.

In one embodiment, the substituted anionic compound according to the invention is characterized in that the saccharide backbone is fucosyllactose.

In one embodiment, the substituted anionic compound according to the invention is characterized in that the saccharide backbone is gentianose.

In one embodiment, the substituted anionic compound according to the invention is characterized in that the saccharide backbone is raffinose.

In one embodiment, the substituted anionic compound according to the invention is characterized in that the saccharide backbone is melezitose.

In one embodiment, the substituted anionic compound according to the invention is characterized in that the saccharide backbone is panose.

In one embodiment, the substituted anionic compound according to the invention is characterized in that the saccharide backbone is kestose.

In one embodiment, the substituted anionic compound according to the invention is characterized in that the saccharide backbone is stachyose.

In one embodiment, the polyanionic compound is a non-polymeric polyanionic (NPP) compound whose affinity for zinc is less than the affinity of insulin for zinc and whose dissociation constant $Kd_{Ca}=[NPP\ compound]^r\ [Ca^{2+}]^s/[(NPP\ compound)^r\text{-}(Ca^{2+})^s]$ is less than or equal to $10^{-1.5}$.

The dissociation constants (Kd) of the various polyanionic compounds with respect to calcium ions are determined by external calibration using an electrode specific for calcium ions (Mettler-Toledo) and a reference electrode. All the measurements are performed in 150 mM NaCl at pH 7. Only the concentrations of free calcium ions are determined; the calcium ions bound to the polyanionic compound do not induce any electrode potential.

In one embodiment, the polyanionic compound is chosen from the group consisting of polycarboxylic acids and the $Na^+$, $K^+$, $Ca^{2+}$ or $Mg^{2+}$ salts thereof.

In one embodiment, the polycarboxylic acid is chosen from the group consisting of citric acid and tartaric acid, and the $Na^+$, $K^+$, $Ca^{2+}$ or $Mg^{2+}$ salts thereof.

In one embodiment, the polyanionic compound is chosen from the group consisting of polyphosphoric acids and the $Na^+$, $K^+$, $Ca^{2+}$ or $Mg^{2+}$ salts thereof.

In one embodiment, the polyphosphoric acid is triphosphate and the $Na^+$, $K^+$, $Ca^{2+}$ or $Mg^{2+}$ salts thereof.

In one embodiment, the polyanionic compound is citric acid and the $Na^+$, $K^+$, $Ca^{2+}$ or $Mg^{2+}$ salts thereof.

In one embodiment, the polyanionic compound is tartaric acid and the $Na^+$, $K^+$, $Ca^{2+}$ or $Mg^{2+}$ salts thereof.

In one embodiment, the polyanionic compound is triphosphoric acid and the $Na^+$, $K^+$, $Ca^{2+}$ or $Mg^{2+}$ salts thereof.

In one embodiment, the polyanionic compound is a compound consisting of a saccharide backbone formed from a discrete number of saccharide units obtained from a disaccharide compound chosen from the group consisting of trehalose, maltose, lactose, sucrose, cellobiose, isomaltose, maltitol and isomaltitol.

In one embodiment, the polyanionic compound consisting of a saccharide backbone formed from a discrete number of saccharide units is obtained from a compound consisting of a backbone formed from a discrete number of saccharide units chosen from the group consisting of maltotriose, maltotetraose, maltopentaose, maltohexaose, maltoheptaose, maltooctaose and isomaltotriose.

In one embodiment, the polyanionic compound consisting of a saccharide backbone formed from a discrete number of saccharide units is chosen from the group consisting of carboxymethylmaltotriose, carboxymethylmaltotetraose, carboxymethylmaltopentaose, carboxymethylmaltohexaose, carboxymethylmaltoheptaose, carboxymethylmaltooctaose and carboxymethylisomaltotriose.

In one embodiment, the ratio (number of moles of acid functions borne by the polyanionic compound/number of moles of anionic compound) is greater than or equal to 3.

In one embodiment, the ratio (number of moles of acid functions borne by the polyanionic compound/number of moles of anionic compound) is greater than or equal to 4.

In one embodiment, the ratio (number of moles of acid functions borne by the polyanionic compound consisting of a saccharide backbone/number of moles of anionic compound) is greater than or equal to 5.

In one embodiment, the ratio (number of moles of acid functions borne by the polyanionic compound consisting of a saccharide backbone/number of moles of anionic compound) is greater than or equal to 8.

In one embodiment, the substituted anionic compound/insulin mole ratios are between 0.6 and 75.

In one embodiment, the mole ratios are between 0.7 and 50.

In one embodiment, the mole ratios are between 1.4 and 35.

In one embodiment, the mole ratios are between 1.9 and 30.

In one embodiment, the mole ratios are between 2.3 and 30.

In one embodiment, the substituted anionic compound/insulin mole ratio is equal to 8.

In one embodiment, the substituted anionic compound/insulin mole ratio is equal to 12.

In one embodiment, the substituted anionic compound/insulin mole ratio is equal to 16.

In one embodiment, the substituted anionic compound/insulin mass ratios are between 0.5 and 10.

In one embodiment, the mass ratios are between 0.6 and 7.

In one embodiment, the mass ratios are between 1.2 and 5.

In one embodiment, the mass ratios are between 1.6 and 4.

In one embodiment, the mass ratios are between 2 and 4.

In one embodiment, the substituted anionic compound/insulin mass ratio is 2.

In one embodiment, the substituted anionic compound/insulin mass ratio is 3.

In one embodiment, the substituted anionic compound/insulin mass ratio is 4.

In one embodiment, the substituted anionic compound/insulin mass ratio is 6.

In one embodiment, the concentration of substituted anionic compound is between 1.8 and 36 mg/mL.

In one embodiment, the concentration of substituted anionic compound is between 1.8 and 36.5 mg/mL.

In one embodiment, the concentration of substituted anionic compound is between 2.1 and 25 mg/mL.

In one embodiment, the concentration of substituted anionic compound is between 4.2 and 18 mg/mL.

In one embodiment, the concentration of substituted anionic compound is between 5.6 and 15 mg/mL.

In one embodiment, the concentration of substituted anionic compound is between 7 and 15 mg/mL.

In one embodiment, the concentration of substituted anionic compound is 7.3 mg/mL.

In one embodiment, the concentration of substituted anionic compound is 10.5 mg/mL.

In one embodiment, the concentration of substituted anionic compound is 14.6 mg/mL.

In one embodiment, the concentration of substituted anionic compound is 21.9 mg/mL.

In one embodiment, the concentration of polyanionic compound is between 2 and 150 mM.

In one embodiment, the concentration of polyanionic compound is between 2 and 100 mM.

In one embodiment, the concentration of polyanionic compound is between 2 and 75 mM.

In one embodiment, the concentration of polyanionic compound is between 2 and 50 mM.

In one embodiment, the concentration of polyanionic compound is between 2 and 30 mM.

In one embodiment, the concentration of polyanionic compound is between 2 and 20 mM.

In one embodiment, the concentration of polyanionic compound is between 2 and 10 mM.

In one embodiment, the concentration of polyanionic compound is between 5 and 150 mM.

In one embodiment, the concentration of polyanionic compound is between 5 and 100 mM.

In one embodiment, the concentration of polyanionic compound is between 5 and 75 mM.

In one embodiment, the concentration of polyanionic compound is between 5 and 50 mM.

In one embodiment, the concentration of polyanionic compound is between 5 and 30 mM.

In one embodiment, the concentration of polyanionic compound is between 5 and 20 mM.

In one embodiment, the concentration of polyanionic compound is between 5 and 10 mM.

In one embodiment, the concentration of polyanionic compound is between 0.5 and 30 mg/mL.

In one embodiment, the concentration of polyanionic compound is between 0.5 and 25 mg/mL.

In one embodiment, the concentration of polyanionic compound is between 0.5 and 10 mg/mL.

In one embodiment, the concentration of polyanionic compound is between 0.5 and 8 mg/mL.

In one embodiment, the concentration of polyanionic compound is between 1 and 30 mg/mL.

In one embodiment, the concentration of polyanionic compound is between 1.5 and 25 mg/mL.

In one embodiment, the concentration of polyanionic compound is between 2 and 25 mg/mL.

In one embodiment, the concentration of polyanionic compound is between 2 and 10 mg/mL.

In one embodiment, the concentration of polyanionic compound is between 2 and 8 mg/mL.

In one embodiment, the substituted anionic compound is sodium maltotriosemethylcarboxylate modified with sodium phenylalaninate, $u=3$, $i=0.65$, $j=1.0$.

In one embodiment, the substituted anionic compound is sodium maltotriosemethylcarboxylate modified with sodium phenylalaninate, $u=3$, $i=1.0$, $j=0.65$.

In one embodiment, the substituted anionic compound is sodium maltotriosemethylcarboxylate modified with sodium phenylalaninate, $u=3$, $i=0.46$, $j=1.2$.

In one embodiment, the substituted anionic compound is sodium maltotriosemethylcarboxylate modified with sodium phenylalaninate, $u=3$, $i=0.35$, $j=0.65$.

In one embodiment, the polyanionic compound is sodium maltotriosemethylcarboxylate.

In one embodiment, the polyanionic compound is sodium citrate.

In one embodiment, the polyanionic compound is triphosphate in acidic form or in basic form in the form of the sodium salt or the potassium salt.

In one embodiment, the polyanionic compound is tartrate in acidic form or in basic form in the form of the sodium salt or the potassium salt.

The invention also relates to an insulin pharmaceutical formulation comprising a composition according to the invention, in which the insulin is in hexameric form.

In one embodiment, it relates to a pharmaceutical formulation characterized in that the insulin concentration is between 240 and 3000 µM (40 to 500 IU/mL).

In one embodiment, it relates to a pharmaceutical formulation characterized in that the insulin concentration is between 600 and 3000 µM (100 to 500 IU/mL).

In one embodiment, it relates to a pharmaceutical formulation characterized in that the insulin concentration is between 600 and 2400 µM (100 to 400 IU/mL).

In one embodiment, it relates to a pharmaceutical formulation characterized in that the insulin concentration is between 600 and 1800 µM (100 to 300 IU/mL).

In one embodiment, it relates to a pharmaceutical formulation characterized in that the insulin concentration is between 600 and 1200 µM (100 to 200 IU/mL).

In one embodiment, it relates to a pharmaceutical formulation characterized in that the insulin concentration is 600 µM (100 IU/mL).

In one embodiment, it relates to a pharmaceutical formulation characterized in that the insulin concentration is 1200 µM (200 IU/mL).

In one embodiment, it relates to a pharmaceutical formulation characterized in that the insulin concentration is 1800 µM (300 IU/mL).

In one embodiment, it relates to a pharmaceutical formulation characterized in that the insulin concentration is 2400 µM (400 IU/mL).

In one embodiment, it relates to a pharmaceutical formulation characterized in that the insulin concentration is 3000 µM (500 IU/mL).

The invention relates to the use of at least one substituted anionic compound, said compound consisting of a saccharide backbone formed from a discrete number u of between 1 and 8 (1≤u≤8) of identical or different saccharide units, linked via identical or different glycoside bonds, said saccharide units being chosen from the group consisting of hexoses, in cyclic form or in open reduced form, said compound comprising partially substituted carboxyl functional groups, the unsubstituted carboxyl functional groups being salifiable to prepare a pharmaceutical formulation of human insulin, in combination with a polyanionic compound, making it possible, after administration, to accelerate the passage of the insulin into the blood and to reduce glycemia more rapidly when compared with a formulation free of substituted anionic compound, and optionally of anionic compounds.

In one embodiment, the invention relates to the use of at least one substituted anionic compound, said compound comprising partially substituted carboxyl functional groups, the unsubstituted carboxyl functional groups being salifiable, to prepare a pharmaceutical formulation of human insulin, in combination with a polyanionic compound, making it possible, after administration, to accelerate the passage of the human insulin into the blood and to reduce glycemia more rapidly when compared with a formulation free of substituted anionic compound, and optionally of anionic compounds.

In one embodiment, the invention relates to the use of at least one substituted anionic compound, said compound comprising partially substituted carboxyl functional groups, the unsubstituted carboxyl functional groups being salifiable, to prepare an insulin analog formulation, in combination with a polyanionic compound, making it possible, after administration, to accelerate the passage of the insulin analog into the blood and to reduce glycemia more rapidly when compared with a formulation free of substituted anionic compound, and optionally of anionic compounds.

In one embodiment, the insulin is human insulin.

The term "human insulin" means an insulin obtained by synthesis or recombination, whose peptide sequence is the sequence of human insulin, including the allelic variations and homologs.

In one embodiment, the insulin is a recombinant human insulin as described in the European Pharmacopea and the American Pharmacopea.

In one embodiment, the insulin is an insulin analog.

The term "insulin analog" means a recombinant insulin whose primary sequence contains at least one modification relative to the primary sequence of human insulin.

In one embodiment, the insulin analog is chosen from the group consisting of the insulin lispro (Humalog®), the insulin aspart (Novolog®, Novorapid®) and the insulin glulisine (Apidra®).

In one embodiment, the insulin analog is the insulin lispro (Humalog®).

In one embodiment, the insulin analog is the insulin aspart (Novolog®, Novorapid®).

In one embodiment, the insulin analog is the insulin glulisine (Apidra®).

In one embodiment, the use is characterized in that the substituted anionic compound is chosen from substituted anionic compounds, in isolated form or as a mixture, consisting of a saccharide backbone formed from a discrete number u of between 1 and 8 (1≤u≤8) of identical or different saccharide units, linked via identical or different glycoside bonds, said saccharide units being chosen from hexoses, in cyclic form or in open reduced form, characterized in that they are substituted with:

a) at least one substituent of general formula I:

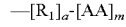

Formula I the substituents being identical or different when there are at least two substituents, in which:
the radical -[AA] denotes an amino acid residue,
the radical —$R_1$— being:
either a bond and then a=0 and the amino acid residue -[AA]- is directly linked to the backbone via a function G,
or a C2 to C15 carbon-based chain, and then a=1, optionally substituted and/or comprising at least one heteroatom chosen from O, N and S and at least one acid function before the reaction with the amino acid, said chain forming with the amino acid residue -[AA]- an amide function, and is attached to the backbone by means of a function F resulting from a reaction between a hydroxyl function borne by the backbone and a function or substituent borne by the precursor of the radical —$R_1$—,
F is a function chosen from ether, ester and carbamate functions,
G is a carbamate function,
m is equal to 1 or 2,
the degree of substitution of the saccharide units, j, in —$[R_1]_a$-$[AA]_m$ being strictly greater than 0 and less than or equal to 6, 0<j≤6 b) and, optionally, one or more substituents —$R'_1$,
the substituent —$R'_1$ being a C2 to C15 carbon-based chain, which is optionally substituted and/or comprising at least one heteroatom chosen from O, N and S and at least one acid function in the form of an alkali metal cation salt, said chain being linked to the backbone via a function F' resulting from a reaction between a hydroxyl function borne by the backbone and a function or substituent borne by the precursor of the substituent —$R'_1$,
F' is an ether, ester or carbamate function,
the degree of substitution of the saccharide units, i, in —$R'_1$, being between 0 and 6−j, 0≤i≤6−j, and
F and F' are identical or different,
F and G are identical or different,
i+j≤6,
—$R'_1$ is identical to or different from —$R_1$—,
the free salifiable acid functions borne by the substituent —$R'_1$ are in the form of alkali metal cation salts, said glycoside bonds, which may be identical or different, being chosen from the group consisting of glycoside bonds of (1,1), (1,2), (1,3), (1,4) or (1,6) type, in an alpha or beta geometry.

In one embodiment, the use is characterized in that the substituted anionic compound, in isolated form or as a mixture, is chosen from substituted anionic compounds consisting of a saccharide backbone formed from a discrete number u of between 1 and 8 (1≤u≤8) of identical or different saccharide units, linked via identical or different glycoside bonds, said saccharide units being chosen from hexoses, in cyclic form or in open reduced form, characterized a) in that they are randomly substituted with:
at least one substituent of general formula I:

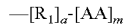
$$—[R_1]_a\text{-}[AA]_m \quad \text{Formula I}$$

the substituents being identical or different when there are at least two substituents, in which:
the radical -[AA]- denotes an amino acid residue, said amino acid being chosen from the group consisting of phenylalanine, alpha-methylphenylalanine, 3,4-dihydroxyphenylalanine, tyrosine, alpha-methyltyrosine, O-methyltyrosine, alpha-phenylglycine, 4-hydroxyphenylglycine and 3,5-dihydroxyphenylglycine, and the alkali metal cation salts thereof, said derivatives being in L or D absolute configuration, -[AA]- is attached to the backbone of the molecule via a linker arm —$R_1$— or directly attached to the backbone via a function G,
—$R_1$— being:
either a bond G, and then a=0,
or a C2 to C15 carbon-based chain, and then a=1, optionally substituted and/or comprising at least one heteroatom chosen from O, N and S and bearing at least one acid function before the reaction with the amino acid, said chain forming with the amino acid residue -[AA]- an amide bond, and is attached to the saccharide backbone by means of a function F resulting from a reaction between a hydroxyl function borne by the backbone and a function borne by the precursor of $R_1$,
F is an ether, ester or carbamate function,
G is a carbamate function,
m is equal to 1 or 2,
the degree of substitution, j, in —$[R_1]_a[AA]_m$ being strictly greater than 0 and less than or equal to 6, 0<j≤6, and, optionally,
one or more substituents —$R'_1$
—$R'_1$ being a C2 to C15 carbon-based chain, which is optionally substituted and/or comprising at least one heteroatom (such as O, N and S) and bearing at least one acid function in the form of an alkali metal cation salt, said chain being attached to the saccharide backbone via a function F' resulting from a reaction between a hydroxyl function borne by the backbone and a function borne by the precursor of —$R'_1$,
F' is an ether, ester or carbamate function,
the degree of substitution, i, in —$R'_1$, being between 0 and 6−j, 0≤i≤6−j, and
—$R'_1$— is identical to or different from —$R_1$,
F and F' are identical or different,
F' and G are identical or different,
the free salifiable acid functions are in the form of alkali metal cation salts.
b) said glycoside bonds, which may be identical or different, being chosen from the group consisting of glycoside bonds of (1,1), (1,2), (1,3), (1,4) or (1,6) type, in an alpha or beta geometry,
c) i+j≤6.

In one embodiment, m is equal to 1.
In one embodiment, —R1 and —R'1, which may be identical or different, are a C1 to C8 carbon-based chain.
In one embodiment, —R1 and —R'1, which may be identical or different, are a C1 to C4 carbon-based chain.
In one embodiment, —R1 and —R'1, which may be identical or different, are a C1 to C2 carbon-based chain.

It is known to those skilled in the art that the delay of action of insulins is dependent on the insulin concentration. Only the delay of action values for formulations at 100 IU/mL are documented.

"Regular" human insulin formulations on the market at a concentration of 600 μM (100 IU/mL) have a delay of action of between 50 and 90 minutes and an end of action of about 360 to 420 minutes in man. The time to achieve the maximum insulin concentration in the blood is between 90 and 180 minutes in man.

Rapid insulin analog formulations on the market at a concentration of 600 μM (100 IU/mL) have a delay of action of between 30 and 60 minutes and an end of action of about 240-300 minutes in man. The time to achieve the maximum insulin concentration in the blood is between 50 and 90 minutes in man.

The invention also relates to a method for preparing a human insulin formulation having an insulin concentration of between 240 and 3000 μM (40 and 500 IU/mL), whose delay of action in man is less than that of the reference formulation at the same insulin concentration in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of between 600 and 1200 μM (100 and 200 IU/mL), whose delay of action in man is less than that of the reference formulation at the same insulin concentration in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of 600 μM (100 IU/mL), whose delay of action in man is less than 60 minutes, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of 1200 μM (200 IU/mL), whose delay of action in man is at least 10% less than that of the human insulin formulation at the same concentration (200 IU/mL) and in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of 1800 µM (300 IU/mL), whose delay of action in man is at least 10% less than that of the human insulin formulation at the same concentration (300 IU/mL) and in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of 2400 µM (400 IU/mL), whose delay of action in man is at least 10% less than that of the human insulin formulation at the same concentration (400 IU/mL) and in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation having an insulin concentration of 3000 µM (500 IU/mL), whose delay of action in man is at least 10% less than that of the human insulin formulation at the same concentration (500 IU/mL) and in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention consists in preparing a rapid human insulin formulation, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing a human insulin formulation at a concentration of 600 µM (100 IU/mL), whose delay of action in man is less than 60 minutes, preferably less than 45 minutes and more preferably less than 30 minutes, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of between 240 and 3000 µM (40 and 500 IU/mL), whose delay of action in man is less than that of the reference formulation at the same insulin concentration in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of between 600 and 1200 µM (100 and 200 IU/mL), whose delay of action in man is less than that of the reference formulation at the same insulin analog concentration in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of 600 µmol/L (100 IU/mL), whose delay of action in man is less than 30 minutes, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of 1200 µM (200 IU/mL), whose delay of action in man is at least 10% less than that of the insulin analog formulation in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of 1800 µM (300 IU/mL), whose delay of action in man is at least 10% less than that of the insulin analog formulation in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of 2400 µM (400 IU/mL), whose delay of action in man is at least 10% less than that of the insulin analog formulation in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention also relates to a method for preparing an insulin analog formulation having an insulin concentration of 3000 µM (500 IU/mL), whose delay of action in man is at least 10% less than that of the insulin analog formulation in the absence of a substituted anionic compound and of a polyanionic compound, characterized in that it comprises (1) a step of adding to said formulation at least one substituted anionic compound, said compound comprising partially substituted carboxyl functional groups, the unsubstituted carboxyl functional groups being salifiable, and (2) a step of adding to said formulation at least one polyanionic compound.

In one embodiment, the insulin is in hexameric form.

The invention consists in preparing a very rapid insulin analog formulation, characterized in that it comprises a step of adding to said formulation at least one substituted anionic compound, said compound comprising partially substituted carboxyl functional groups, the unsubstituted carboxyl functional groups being salifiable.

In one embodiment, the preparation also comprises a step of adding to said formulation at least one polyanionic compound.

In one embodiment, the insulin is in hexameric form.

In one embodiment, the insulin analog is chosen from the group consisting of the insulin lispro (Humalog®), the insulin aspart (Novolog®, Novorapid®) and the insulin glulisine (Apidra®).

In one embodiment, the insulin analog is the insulin lispro (Humalog®).

In one embodiment, the insulin analog is the insulin aspart (Novolog®, Novorapid®).

In one embodiment, the insulin analog is the insulin glulisine (Apidra®).

In one embodiment, the insulin is a recombinant human insulin as described in the European Pharmacopea and the American Pharmacopea.

In one embodiment, the insulin is an insulin analog chosen from the group consisting of the insulin lispro (Humalog®), the insulin aspart (Novolog®, Novorapid®) and the insulin glulisine (Apidra®).

The composition may furthermore be prepared by simple mixing of an aqueous solution of human insulin or of insulin analog and an aqueous solution of substituted anionic compound as a mixture with a polyanionic compound.

In one embodiment, the composition may be prepared by simple mixing of an aqueous solution of human insulin or of insulin analog, an aqueous solution of substituted anionic compound and a polyanionic compound in solution or in lyophilizate form.

In one embodiment, the composition may be prepared by simple mixing of an aqueous solution of human insulin or of insulin analog, a substituted anionic compound in lyophilizate form and a polyanionic compound in solution or in lyophilizate form.

Preferably, this composition is in the form of an injectable solution.

In one embodiment, the concentration of human insulin or insulin analog is between 240 and 3000 µM (40 to 500 IU/mL).

In one embodiment, the concentration of human insulin or insulin analog is between 600 and 3000 µM (100 to 500 IU/mL).

In one embodiment, the concentration of human insulin or insulin analog is between 600 and 2400 µM (100 to 400 IU/mL).

In one embodiment, the concentration of human insulin or insulin analog is between 600 and 1800 µM (100 to 300 IU/mL).

In one embodiment, the concentration of human insulin or insulin analog is between 600 and 1200 µM (100 to 200 IU/mL).

In one embodiment, the concentration of human insulin or insulin analog is 600 µM (100 IU/mL).

In one embodiment, the concentration of human insulin or insulin analog is 1200 µM (200 IU/mL).

In one embodiment, the concentration of human insulin or insulin analog of 600 µM (100 IU/mL) may be reduced by simple dilution, in particular for pediatric applications.

In one embodiment, the concentration of human insulin or insulin analog is 1800 µM (300 IU/mL).

In one embodiment, the concentration of human insulin or insulin analog is 2400 µM (400 IU/mL).

In one embodiment, the concentration of human insulin or insulin analog is 3000 µM (500 IU/mL).

The invention also relates to a pharmaceutical formulation according to the invention, characterized in that it is obtained by drying and/or lyophilization.

In one embodiment, the compositions according to the invention also comprise the addition of zinc salts to a concentration of between 0 and 500 µM.

In one embodiment, the compositions according to the invention also comprise the addition of zinc salts to a concentration of between 0 and 300 µM.

In one embodiment, the compositions according to the invention also comprise the addition of zinc salts to a concentration of between 0 and 200 µM.

In one embodiment, the compositions according to the invention comprise buffers at concentrations of between 0 and 100 mM, preferably between 0 and 50 mM or between 15 and 50 mM.

In one embodiment, the buffer is Tris.

In one embodiment, the compositions according to the invention also comprise preservatives.

In one embodiment, the preservatives are chosen from the group consisting of m-cresol and phenol, alone or as a mixture.

In one embodiment, the concentration of preservatives is between 10 and 50 mM.

In one embodiment, the concentration of preservatives is between 10 and 40 mM.

The compositions according to the invention may also comprise additives such as tonicity agents, for instance glycerol, sodium chloride (NaCl), mannitol and glycine.

The compositions according to the invention may also comprise additives in accordance with the pharmacopeas, for instance surfactants, for example polysorbate.

The compositions according to the invention may also comprise any excipient in accordance with the pharmacopeas which are compatible with the insulins used at the working concentrations.

In the case of local and systemic release, the envisaged modes of administration are intravenous, subcutaneous, intradermal or intramuscular.

Transdermal, oral, nasal, vaginal, ocular, oral and pulmonary administration routes are also envisaged.

The invention also relates to the use of a composition according to the invention for the formulation of a solution of human insulin or insulin analog in a concentration of 100 IU/mL intended for implantable or transportable insulin pumps.

The invention also relates to the use of a composition according to the invention for the formulation of a solution of human insulin or insulin analog in a concentration of 200 IU/mL intended for implantable or transportable insulin pumps.

The invention also relates to substituted anionic compound, in isolated form or as a mixture, chosen from substituted anionic compounds consisting of a saccharide backbone formed from a discrete number u of between 1 and 8 ($1 \leq u \leq 8$) of identical or different saccharide units, linked via identical or different glycoside bonds, said saccharide units being chosen from hexoses, in cyclic form or in open reduced form, characterized in that they are substituted with:

a) at least one substituent of general formula I:

$—[R_1]_a-[AA]_m$   Formula I the substituents being identical or different when there are at least two substituents, in which:
the radical -[AA] denotes an amino acid residue,
the radical $—R_1—$ being:
  either a bond and then a=0 and the amino acid residue -[AA]- is directly linked to the backbone via a function G,
  or a C2 to C15 carbon-based chain, and then a=1, optionally substituted and/or comprising at least one heteroatom chosen from O, N and S and at least one acid function before the reaction with the amino acid, said chain forming with the amino acid residue -[AA]- an amide function, and is attached to the backbone by means of a function F resulting from a reaction between a hydroxyl function borne by the backbone and a function or substituent borne by the precursor of the radical $—R_1—$,
F is a function chosen from ether, ester and carbamate functions,
G is a carbamate function,
m is equal to 1 or 2,
the degree of substitution of the saccharide units, j, in $—[R_1]_a-[AA]_m$ being strictly greater than 0 and less than or equal to 6, $0 < j \leq 6$ b) and, optionally, one or more substituents $—R'_1$,
  the substituent $—R'_1$ being a C2 to C15 carbon-based chain, which is optionally substituted and/or comprising at least one heteroatom chosen from O, N and S and at least one acid function in the form of an alkali metal cation salt, said chain being linked to the backbone via a function F' resulting from a reaction between a hydroxyl function borne by the backbone and a function or substituent borne by the precursor of the substituent $—R'_1$,
F' is an ether, ester or carbamate function,
the degree of substitution of the saccharide units, i, in $—R'_1$, being between 0 and 6–j, $0 \leq i \leq 6-j$, and
F and F' are identical or different,
F and G are identical or different,
$i+j \leq 6$,
$—R'_1$ is identical to or different from $—R_1—$,
the free salifiable acid functions borne by the substituent $—R'_1$ are in the form of alkali metal cation salts,
said glycoside bonds, which may be identical or different, being chosen from the group consisting of glycoside bonds of (1,1), (1,2), (1,3), (1,4) or (1,6) type, in an alpha or beta geometry.

In the above formula, the different variables have the values mentioned above.

The substituted anionic compounds according to the invention may be obtained by random grafting of substituents onto the saccharide backbone.

In one embodiment, the substituted anionic compounds chosen from anionic compounds substituted with substituents of formula I or II are characterized in that they may be obtained by grafting substituents in precise positions onto the saccharide units via a process involving steps of protection/deprotection of the alcohol or carboxylic acid groups naturally borne by the backbone. This strategy leads to selective grafting, especially regioselective grafting, of the substituents onto the backbone. The protecting groups include, without limitation, those described in the publication (Wuts, P. G. M. et al., Greene's Protective Groups in Organic Synthesis 2007).

The saccharide backbone may be obtained by degradation of a high molecular weight polysaccharide. The degradation routes include, without limitation, chemical degradation and/or enzymatic degradation.

The saccharide backbone may also be obtained by formation of glycoside bonds between monosaccharide or oligosaccharide molecules using a chemical or enzymatic coupling strategy. The coupling strategies include those described in the publication (Smoot, J. T. et al., Advances in Carbohydrate Chemistry and Biochemistry 2009, 62, 162-250) and in the publication (Lindhorst, T. K., Essentials of Carbohydrate Chemistry and Biochemistry 2007, 157-208). The coupling reactions may be performed in solution or on a solid support. The saccharide molecules before coupling may bear substituents of interest and/or may be functionalized once coupled together, randomly or regioselectively.

Thus, by way of example, the compounds according to the invention may be obtained according to one of the following processes:
  the random grafting of substituents onto a saccharide backbone
  one or more steps of glycosylation between monosaccharide or oligosaccharide molecules bearing substituents
  one or more steps of glycosylation between one or more monosaccharide or oligosaccharide molecules bearing substituents and one or more monosaccharide or oligosaccharide molecules
  one or more steps of introduction of protecting groups onto alcohols or acids naturally borne by the saccharide backbone, followed by one or more substituent grafting reactions and finally a step of removal of the protecting groups
  one or more steps of glycosylation between one or more monosaccharide or oligosaccharide molecules bearing protecting groups on alcohols or acids naturally borne by the saccharide backbone, one or more steps of grafting substituents onto the backbone obtained, and then a step of removal of the protecting groups
  one or more steps of glycosylation between one or more monosaccharide or oligosaccharide molecules bearing protecting groups on alcohols or acids naturally borne by the saccharide backbone, and one or more monosaccharide or oligosaccharide molecules, one or more substituent grafting steps and then a step of removal of the protecting groups.

The compounds according to the invention, isolated or as a mixture, may be separated and/or purified in various ways, especially after having been obtained via the processes described above.

Mention may be made in particular of chromatographic methods, especially "preparative" methods such as:
  flash chromatography, especially on silica, and
  chromatography such as HPLC (high-performance liquid chromatography), in particular RP-HPLC (reverse-phase HPLC).

Selective precipitation methods may also be used.

The invention is illustrated by the examples that follow.

EXAMPLES

The structures of the substituted anionic compounds according to the invention are presented in Table 1. The structures of the polysaccharide counterexamples are presented in Table 2.

TABLE 1

AA Substituted anionic compounds

| Compound | i | j | Saccharide chain | Substituent —R'₁ | Substituent —[R₁]ₐ—[AA]ₘ |
|---|---|---|---|---|---|
| 1 | 0.65 | 1.0 | | CH₂CH₂COONa | CH₂CH₂C(O)NH-CH(CH₂Ph)-COONa |
| 2 | 1.0 | 0.65 | | CH₂CH₂COONa | CH₂CH₂C(O)NH-CH(CH₂Ph)-COONa |
| 3 | 0.46 | 1.2 | | CH₂CH₂COONa | CH₂CH₂C(O)NH-CH(CH₂Ph)-COONa |
| 4 | 0.35 | 0.65 | | CH₂CH₂COONa | CH₂CH₂C(O)NH-CH(CH₂Ph)-COONa |
| 5 | 1.25 | 0.4 | | CH₂CH₂COONa | CH₂CH₂C(O)NH-CH(CH₂Ph)-COONa |
| 6 | 0.8 | 0.65 | | CH₂CH₂COONa | CH₂CH₂C(O)NH-CH(CH₂Ph)-COONa |
| 7 | 2.65 | 0.65 | | CH₂CH₂COONa | CH₂CH₂C(O)NH-CH(CH₂Ph)-COONa |

TABLE 1-continued

AA Substituted anionic compounds

| Compound | i | j | Saccharide chain | Substituent —R'$_1$ | Substituent —[R$_1$]$_a$—[AA]$_m$ |
|---|---|---|---|---|---|
| 8 | 1.0 | 0.75 | (structure with subscript 3) | CH$_2$CH$_2$C(O)ONa | phenylalanine-amide derivative |
| 9 | 1.0 | 0.65 | (structure with subscript 6) | CH$_2$CH$_2$C(O)ONa | phenylalanine-amide derivative |
| 10 | 0.83 | 0.81 | (saccharide structure) | CH$_2$CH$_2$C(O)ONa | tyrosine-amide derivative |
| 11 | 1.12 | 0.52 | (saccharide structure) | CH$_2$CH$_2$C(O)ONa | phenylglycine-amide derivative |

R = H, R'$_1$, —[R$_1$]$_a$—[AA]$_m$

TABLE 2

AB Polysaccharide counterexamples

| Polysaccharide counterexamples | i | j | Saccharide chain | Weight-average molar mass (kg/mol) | Substituent —R'$_1$ | Substituent —[R$_1$]$_a$—[AA]$_m$ |
|---|---|---|---|---|---|---|
| AB1 | 0.6 | 0.46 | (saccharide structure) | 10 | CH$_2$CH$_2$C(O)ONa | phenylalanine-amide derivative |

TABLE 2-continued

AB Polysaccharide counterexamples

| Polysaccharide counterexamples | i | j | Saccharide chain | Weight-average molar mass (kg/mol) | Substituent —R'$_1$ | Substituent —[R$_1$]$_a$—[AA]$_m$ |
|---|---|---|---|---|---|---|
| AB2 | 1.01 | 0.64 | (structure) | 5 | (CH$_2$COONa) | (phenylalaninate amide, ONa) |
| AB3 | 0.65 | 0.45 | (structure) | 5 | (CH$_2$COONa) | (phenylalaninate amide, ONa) |
| AB4 | 1.01 | 0.64 | (structure) | 10 | (CH$_2$COONa) | (phenylalaninate amide, ONa) |
| AB5 | 0.45 | 0.65 | (structure) | 5 | (CH$_2$COONa) | (phenylalaninate amide, ONa) |

Polysaccharide counterexamples AB1, AB2, AB3, AB4 and AB5: R = H, R'$_1$, —[R$_1$]$_a$—[AA]$_m$

AA1. Compound 1: Sodium Maltotriosemethylcarboxylate Functionalized with Sodium L-Phenylalaninate To 8 g (143 mmol of hydroxyl functions) of maltotriose (CarboSynth) dissolved in water at 65° C. is added 0.6 g (16 mmol) of sodium borohydride. After stirring for 30 minutes, 28 g (238 mmol) of sodium chloroacetate are added. To this solution are then added dropwise 24 mL of 10 N NaOH (24 mmol), and the mixture is then heated at 65° C. for 90 minutes. 16.6 g (143 mmol) of sodium chloroacetate are then added to the reaction medium, along with dropwise addition of 14 mL of 10 N NaOH (14 mmol). After heating for 1 hour, the mixture is diluted with water, neutralized with acetic acid and then purified by ultrafiltration on a 1 kDa PES membrane against water. The molecule concentration of the final solution is determined on the dry extract, and an acid/base assay in a 50/50 (V/V) water/acetone mixture is then performed to determine the degree of substitution with methylcarboxylate.

According to the dry extract: [compound]=32.9 mg/g

According to the acid/base assay, the degree of substitution with methylcarboxylate is 1.65 per saccharide unit.

The sodium maltotriosemethylcarboxylate solution is acidified on a Purolite resin (anionic) to obtain maltotriosemethylcarboxylic acid, which is then lyophilized for 18 hours.

10 g of maltotriosemethylcarboxylic acid (63 mmol of methylcarboxylic acid functions) are dissolved in DMF and then cooled to 0° C. A mixture of ethyl phenylalaninate, hydrochloride salt (8.7 g, 38 mmol) in DMF is prepared. 3.8 g of triethylamine (38 mmol) are added to this mixture. A solution of NMM (6.3 g, 63 mmol) and of EtOCOCl (6.8 g, 63 mmol) is then added to the mixture at 0° C. The ethyl phenylalaninate solution is then added and the mixture is stirred at 10° C. An aqueous imidazole solution is added and the mixture is then heated to 30° C. The medium is diluted with water and the solution obtained is then purified by ultrafiltration on a 1 kDa PES membrane against 0.1 N NaOH, 0.9% NaCl and water. The molecule concentration of the final solution is determined on the dry extract. A sample of solution is lyophilized and analyzed by $^1$H NMR in D$_2$O to determine the degree of substitution with methylcarboxylates functionalized with sodium L-phenylalaninate.

According to the dry extract: [compound 1]=29.4 mg/g

According to the acid/base assay, the degree of substitution with sodium methylcarboxylates is 0.65 per saccharide unit.

According to the ¹H NMR: the degree of substitution with methylcarboxylates functionalized with sodium L-phenylalaninate is 1.0 per saccharide unit.

AA2. Compound 2: Sodium Maltotriosemethylcarboxylate Functionalized with Sodium L-Phenylalaninate Via a process similar to that used for the preparation of compound 1, a sodium maltotriosecarboxylate functionalized with sodium L-phenylalaninate is obtained. According to the acid/base assay, the degree of substitution with sodium methylcarboxylates is 1.0 per saccharide unit.

According to the dry extract: [compound 2]=20.2 mg/g
According to the ¹H NMR: the degree of substitution with methylcarboxylates functionalized with sodium L-phenylalaninate is 0.65 per saccharide unit.

AA3. Compound 3: Sodium Maltotriosemethylcarboxylate Functionalized with Sodium L-Phenylalaninate Via a process similar to that used for the preparation of compound 1, a sodium maltotriosecarboxylate functionalized with sodium L-phenylalaninate is obtained. According to the acid/base assay, the degree of substitution with sodium methylcarboxylates is 0.46 per saccharide unit.

According to the dry extract: [compound 3]=7.2 mg/g
According to the ¹H NMR: the degree of substitution with methylcarboxylates functionalized with sodium L-phenylalaninate is 1.2 per saccharide unit.

AA4. Compound 4: Sodium Maltotriosemethylcarboxylate Functionalized with Sodium L-Phenylalaninate Via a process similar to that used for the preparation of compound 1, a sodium maltotriosecarboxylate functionalized with sodium L-phenylalaninate is obtained. According to the acid/base assay, the degree of substitution with sodium methylcarboxylates is 0.35 per saccharide unit.

According to the dry extract: [compound 4]=3.1 mg/g
According to the ¹H NMR: the degree of substitution with methylcarboxylates functionalized with sodium L-phenylalaninate is 0.65 per saccharide unit.

AA5. Compound 5: Sodium Maltotriosemethylcarboxylate Functionalized with Sodium L-Phenylalaninate Via a process similar to that used for the preparation of compound 1, a sodium maltotriosemethylcarboxylate functionalized with sodium L-phenylalaninate is obtained.

According to the dry extract: [compound 5]=10.9 mg/g
According to the ¹H NMR: the degree of substitution with methylcarboxylates functionalized with sodium L-phenylalaninate is 0.40 per saccharide unit.
The degree of substitution with sodium methylcarboxylates is 1.25 per saccharide unit.

AA6. Compound 6: Sodium Maltotriosemethylcarboxylate Functionalized with Sodium L-Phenylalaninate To 8 g (143 mmol of hydroxyl functions) of maltotriose (CarboSynth) dissolved in water at 65° C. is added 0.6 g (16 mmol) of sodium borohydride. After stirring for 30 minutes, 28 g (237 mmol) of sodium chloroacetate are added. To this solution are then added dropwise 24 mL of 10 N NaOH (240 mmol). After heating at 65° C. for 90 minutes, the mixture is diluted with water, neutralized by adding acetic acid and then purified by ultrafiltration on a 1 kDa PES membrane against water. The compound concentration of the final solution is determined on the dry extract, and an acid/base assay in a 50/50 (V/V) water/acetone mixture is then performed to determine the degree of substitution with sodium methylcarboxylate.

According to the dry extract: [compound]=14.5 mg/g
According to the acid/base assay, the degree of substitution with sodium methylcarboxylates is 1.45 per saccharide unit.

The sodium maltotriosemethylcarboxylate solution is acidified on a Purolite resin (anionic) to obtain maltotriosemethylcarboxylic acid, which is then lyophilized for 18 hours.

Via a process similar to that used for the preparation of compound 1, a sodium maltotriosemethylcarboxylate functionalized with sodium L-phenylalaninate is obtained.

According to the dry extract: [compound 6]=10.8 mg/g
According to the ¹H NMR, the degree of substitution with methylcarboxylates functionalized with sodium L-phenylalaninate is 0.65 per saccharide unit.
The degree of substitution with sodium methylcarboxylates is 0.8 per saccharide unit.

AA7. Compound 7: Sodium Maltotriosemethylcarboxylate Functionalized with Sodium L-Phenylalaninate Via a process similar to that described in the preparation of compound 1, 8 g of sodium maltotriosemethylcarboxylate characterized by a degree of substitution with sodium methylcarboxylate of 1.76 are synthesized and lyophilized.

8 g (58 mmol of hydroxyl functions) of the lyophilizate and 15 g (129 mmol) of sodium chloroacetate are dissolved in water at 65° C. To this solution are added dropwise 13 mL of 10 N NaOH (130 mmol) and the mixture is then heated at 65° C. for 90 minutes. 9 g (78 mmol) of sodium chloroacetate are then added to the reaction medium, along with dropwise addition of 8 mL of 10 N NaOH (80 mmol). After heating for 1 hour, the mixture is diluted with water, neutralized with acetic acid and then purified by ultrafiltration on a 1 kDa PES membrane against water. The compound concentration of the final solution is determined on the dry extract, and an acid/base assay in a 50/50 (V/V) water/acetone mixture is then performed to determine the degree of substitution with sodium methylcarboxylates.

According to the dry extract: [compound]=11.7 mg/g
According to the acid/base assay, the degree of substitution with sodium methylcarboxylates is 3.30 per saccharide unit.

The sodium maltotriosemethylcarboxylate solution is acidified on a Purolite resin (anionic) to obtain maltotriosemethylcarboxylic acid, which is then lyophilized for 18 hours.

Via a process similar to that used for the preparation of compound 1, a sodium maltotriosemethylcarboxylate functionalized with sodium L-phenylalaninate is obtained.

According to the dry extract: [compound 7]=14.9 mg/g
According to the ¹H NMR: the degree of substitution with methylcarboxylates functionalized with sodium L-phenylalaninate is 0.65 per saccharide unit.

The degree of substitution with sodium methylcarboxylates is 2.65 per saccharide unit.

AA8. Compound 8: Sodium Maltopentaosemethylcarboxylate Functionalized with Sodium L-Phenylalaninate Via a process similar to that described for the preparation of compound 1, but performed with maltopentaose (Carbo-Synth), 10 g of maltopentaosemethylcarboxylic acid with a degree of substitution with methylcarboxylic acid of 1.75 per saccharide unit are obtained and then lyophilized.

Via a process similar to that used for the preparation of compound 1, a sodium maltopentaosemethylcarboxylate functionalized with sodium L-phenylalaninate is obtained.

According to the dry extract: [compound 8]=7.1 mg/g

According to the $^1$H NMR: the degree of substitution with methylcarboxylates functionalized with sodium L-phenylalaninate is 0.75 per saccharide unit.

The degree of substitution with sodium methylcarboxylates is 1.0 per saccharide unit.

AA9. Compound 9: Sodium Maltooctaosemethylcarboxylate Functionalized with Sodium L-Phenylalaninate Via a process similar to that described for the preparation of compound 1, but performed with maltooctaose (Carbo-Synth), 10 g of maltooctaosemethylcarboxylic acid with a degree of substitution with methylcarboxylic acid of 1.65 per saccharide unit are obtained and then lyophilized.

Via a process similar to that used for the preparation of compound 1, a sodium maltooctaosemethylcarboxylate functionalized with sodium L-phenylalaninate is obtained.

According to the dry extract: [compound 9]=26.3 mg/g

According to the $^1$H NMR: the degree of substitution with methylcarboxylates functionalized with sodium L-phenylalaninate is 0.65 per saccharide unit.

The degree of substitution with sodium methylcarboxylates is 1.0 per saccharide unit.

AA10. Compound 10: Sodium Maltotriosemethylcarboxylate Functionalized with Sodium L-Tyrosinate Via a process similar to that described for the preparation of compound 1, but performed with methyl L-tyrosinate, hydrochloride salt (Bachem), a sodium maltotriosemethylcarboxylate, characterized by a degree of substitution with sodium methylcarboxylate per saccharide unit of 1.64, is functionalized with sodium L-tyrosinate.

According to the dry extract: [compound 10]=9.1 mg/g

According to the $^1$H NMR: the degree of substitution with methylcarboxylates functionalized with sodium L-tyrosinate is 0.81 per saccharide unit. The degree of substitution with sodium methylcarboxylates is 0.83 per saccharide unit.

AA11. Compound 11: Sodium Maltotriosemethylcarboxylate Functionalized with Sodium Alpha-Phenylglycinate Via a process similar to that described for the preparation of compound 1, 10 g of maltotriosemethylcarboxylic acid with a degree of substitution with methylcarboxylic acid of 1.64 per saccharide unit are obtained and then lyophilized.

8 g of maltotriosemethylcarboxylic acid (50 mmol of methylcarboxylic acid functions) are dissolved in DMF and then cooled to 0° C. A mixture of sodium alpha-phenylglycinate (Bachem, 5 g; 33 mmol) and triethylamine (33 mmol) is prepared in water. A solution of NMM (4.9 g; 49 mmol) and of EtOCOCl (5.3 g, 49 mmol) is then added to the solution of maltotriosemethylcarboxylic acid at 0° C. The solution of sodium alpha-phenylglycinate and triethylamine is then added and the mixture is stirred at 30° C. An aqueous imidazole solution (340 g/L) is added after 90 minutes. The medium is diluted with water and the solution obtained is then purified by ultrafiltration on a 1 kDa PES membrane against a 150 mM NaHCO$_3$/Na$_2$CO$_3$ pH 10.4 buffer, 0.9% NaCl and water. The compound concentration of the final solution is determined on the dry extract. A sample of solution is lyophilized and analyzed by $^1$H NMR in D$_2$O to determine the degree of substitution with methylcarboxylates functionalized with sodium alpha-phenylglycinate.

According to the dry extract: [compound 11]=9.1 mg/g

According to the $^1$H NMR: the degree of substitution with methylcarboxylates functionalized with sodium alpha-phenylglycinate is 0.52 per saccharide unit.

The degree of substitution with sodium methylcarboxylates is 1.12 per saccharide unit.

AB Polysaccharide Counterexamples

AB1. Polysaccharide 1: Sodium Dextranmethylcarboxylate Functionalized with Sodium L-Phenylalaninate Polysaccharide 1 is a sodium dextranmethylcarboxylate functionalized with sodium L-phenylalaninate obtained from a dextran with a weight-average molar mass of 10 kg/mol (DP=39, Pharmacosmos) according to the process described in patent application FR 07/02316 published under the number FR 2 914 305. According to the acid/base assay, the degree of substitution with sodium methylcarboxylates is 0.6 per saccharide unit.

According to the $^1$H NMR: the degree of substitution with methylcarboxylates functionalized with sodium L-phenylalaninate is 0.46 per saccharide unit.

This polysaccharide corresponds to polysaccharide 1 of patent application FR 09/01478.

AB2. Polysaccharide 2: Sodium Dextranmethylcarboxylate Functionalized with Sodium L-Phenylalaninate Polysaccharide 2 is a sodium dextranmethylcarboxylate functionalized with sodium L-phenylalaninate obtained from a dextran with a weight-average molar mass of 5 kg/mol (DP=19, Pharmacosmos) according to the process described in patent application FR 07/02316 published under the number FR 2 914 305. According to the acid/base assay, the degree of substitution with sodium methylcarboxylates is 1.01 per saccharide unit.

According to the $^1$H NMR: the degree of substitution with methylcarboxylates functionalized with sodium L-phenylalaninate is 0.64 per saccharide unit.

AB3. Polysaccharide 3: Sodium Dextranmethylcarboxylate Functionalized with Sodium L-Phenylalaninate Polysaccharide 3 is a sodium dextranmethylcarboxylate functionalized with sodium L-phenylalaninate obtained from a dextran with a weight-average molar mass of 5 kg/mol (DP=19, Pharmacosmos) according to the process described in patent application FR 07/02316 published under the number FR 2 914 305. According to the acid/base assay, the degree of substitution with sodium methylcarboxylates is 0.65 per saccharide unit.

According to the $^1$H NMR: the degree of substitution with methylcarboxylates functionalized with sodium L-phenylalaninate is 0.45 per saccharide unit.

AB4. Polysaccharide 4: Sodium Dextranmethylcarboxylate Functionalized with Sodium L-Phenylalaninate Polysaccharide 4 is a sodium dextranmethylcarboxylate functionalized with sodium L-phenylalaninate obtained from a dextran with a weight-average molar mass of 10 kg/mol (DP=39, Pharmacosmos) according to the process described in patent application FR 07/02316 published under the number FR 2 914 305. According to the acid/base assay, the degree of substitution with sodium methylcarboxylates is 1.01 per saccharide unit.

According to the $^1$H NMR: the degree of substitution with methylcarboxylates functionalized with sodium L-phenylalaninate is 0.64 per saccharide unit.

AB5. Polysaccharide 5: Sodium Dextranmethylcarboxylate Functionalized with Sodium L-Phenylalaninate Polysaccharide 5 is a sodium dextranmethylcarboxylate functionalized with sodium L-phenylalaninate obtained from a dextran with a weight-average molar mass of 5 kg/mol (DP=19, Pharmacosmos) according to the process described in patent application FR 07/02316 published under the number FR 2 914 305. According to the acid/base assay, the degree of substitution with sodium methylcarboxylates is 0.45 per saccharide unit.

According to the $^1$H NMR: the degree of substitution with methylcarboxylates functionalized with sodium L-phenylalaninate is 0.65 per saccharide unit.

AC Polyanionic Compound

Polyanionic Compound 1: Sodium Maltotriosemethylcarboxylate

To 8 g (143 mmol of hydroxyl functions) of maltotriose (CarboSynth) dissolved in water at 65° C. is added 0.6 g (16 mmol) of sodium borohydride. After stirring for 30 minutes, 28 g (238 mmol) of sodium chloroacetate are added. To this solution are then added dropwise 24 mL of 10 N NaOH (240 mmol), and the mixture is then heated at 65° C. for 90 minutes. 16.6 g (143 mmol) of sodium chloroacetate are then added to the reaction medium, along with dropwise addition of 14 mL of 10 N NaOH (140 mmol). After heating for 1 hour, the mixture is diluted with water, neutralized with acetic acid and then purified by ultrafiltration on a 1 kDa PES membrane against water. The compound concentration of the final solution is determined on the dry extract, and an acid/base assay in a 50/50 (V/V) water/acetone mixture is then performed to determine the degree of substitution with sodium methylcarboxylate.

According to the dry extract: [polyanionic compound 1]=32.9 mg/g

According to the acid/base assay: the degree of substitution with sodium methylcarboxylates is 1.65 per saccharide unit.

B Preparation of the Solutions

B1. Solution of Rapid Insulin Analog Novolog® at 100 IU/mL

This solution is a commercial solution of aspart insulin from Novo Nordisk sold under the name Novolog®. This product is an aspart rapid insulin analog.

B2. Solution of Rapid Insulin Analog Humalog® at 100 IU/mL

This solution is a commercial solution of lispro insulin from Eli Lilly sold under the name Humalog®. This product is a rapid insulin analog.

B3. Solution of Regular Human Insulin Actrapid® at 100 IU/mL

This solution is a commercial solution of human insulin from Novo Nordisk sold under the name Actrapid®. This product is a regular human insulin.

B4. Solution of Regular Human Insulin Humulin® R at 100 IU/mL

This solution is a commercial solution of human insulin from Eli Lilly sold under the name Humulin® R. This product is a regular human insulin.

B5. Preparation of the Excipient Solutions

The non-polymeric polyanionic compounds are selected by measuring their dissociation constant with respect to calcium ions and with respect to their capacity for not destabilizing the hexameric form of insulin.

As regards the dissociation constant with respect to calcium ions, it is determined as follows.

Solutions containing 2.5 mM of $CaCl_2$, 150 mM of NaCl and increasing concentrations of polyanionic compound (between 0 and 20 mM) are prepared. The potential of all these formulations is measured and the concentrations of free calcium ions in the formulations are determined. After linearization by the Scatchard method, the dissociation constants are established. These data make it possible to compare the affinity of the carboxylates and phosphates of the various polyanionic compounds for Ca.

As regards their capacity for not destabilizing the hexameric form of insulin, this property is measured by circular dichroism in comparison with insulin alone (without anionic compound or polyanionic compound), see the experimental protocols in experimental section D.

Preparation of a Sodium Citrate Solution at 1.188 M

A sodium citrate solution is obtained by dissolving 9.0811 g of sodium citrate (30.9 mmol) in 25 mL of water in a graduated flask. The pH is adjusted to exactly 7.4 by adding 1 mL of 1 M HCl. The solution is filtered through a 0.22 μm filter.

Preparation of a 130 mM m-Cresol Solution

An m-cresol solution is obtained by dissolving 14.114 g of m-cresol (130 mmol) in 986.4 mL of water in a 1 L graduated flask.

Preparation of a Solution of m-Cresol and Glycerol
(96.6 mM m-Cresol and 566 mM Glycerol)

73.3 g of the 130 mM m-cresol solution are added to 5.26 g of glycerol and then diluted by addition of 22.25 g of water. The m-cresol and glycerol solution obtained is homogenized for 30 minutes and then filtered through a 0.22 µm membrane.

Preparation of a 32.7 mM Tween 20 Solution

A Tween 20 solution is obtained by dissolving 2.0079 g of Tween 20 (1.636 mmol) in 50 mL of water in a graduated flask. The solution is filtered through a 0.22 µm membrane.

B6. Preparation of a 500 IU/mL Human Insulin Solution 15 g of water are added to 563.6 mg of human insulin and the pH is then lowered to acidic pH by adding 5.98 g of 0.1 N HCl. After total dissolution of the insulin at acidic pH, the solution is neutralized to pH 7.2 by adding 8.3 mL of 0.1 N NaOH. The concentration is then adjusted to 500 IU/mL by adding 0.76 g of water. The solution is finally filtered through a 0.22 µm membrane.

B7. Preparation of a 100 IU/mL Lispro Insulin Solution in the Presence of Compound 1

For a final volume of 100 mL of formulation, with a [compound 1]/[lispro insulin] mass ratio of 2.0, the various reagents are added in the amounts specified below and in the following order:

| Lyophilized compound 1 | 730 mg |
| 100 IU/mL Humalog ® commercial solution | 100 mL |

The final pH is adjusted to 7.4±0.4.
The clear solution is filtered through a 0.22 µm membrane and stored at 4° C.

B8. Preparation of a 100 IU/mL Lispro Insulin Solution in the Presence of Compound 1 and Citrate For a final volume of 100 mL of formulation, with a [compound 1]/[lispro insulin] mass ratio of 2.0 and a citrate concentration of 9.3 mM, the various reagents are added in the amounts specified below and in the following order:

| Lyophilized compound 1 | 730 mg |
| 100 IU/mL Humalog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.
The final pH is adjusted to 7.4±0.4.
The clear solution is filtered through a 0.22 µm membrane and stored at 4° C.

B9. Preparation of a 100 IU/mL Lispro Insulin Solution in the Presence of Compound 1 and the Polyanionic Compound 1

For a final volume of 100 mL of formulation, with a [compound 1]/[polyanionic compound 1]/[lispro insulin] mass ratio of 2.0/2.0/1, the various reagents are added in the amounts specified below and in the following order:

| Lyophilized compound 1 | 730 mg |
| Lyophilized polyanionic compound 1 | 730 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.
The final pH is adjusted to 7.4±0.4.
The clear solution is filtered through a 0.22 µm membrane and stored at 4° C.

B10. Preparation of a 100 IU/mL Lispro Insulin Solution in the Presence of Compound 1 and the Polyanionic Compound 1

For a final volume of 100 mL of formulation, with a [compound 1]/[polyanionic compound 1]/[lispro insulin] mass ratio of 2.0/5.5/1, the various reagents are added in the amounts specified below and in the following order:

| Lyophilized compound 1 | 730 mg |
| Lyophilized polyanionic compound 1 | 2000 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.
The final pH is adjusted to 7.4±0.4.
The clear solution is filtered through a 0.22 µm membrane and stored at 4° C.

B11. Preparation of a 100 IU/mL Lispro Insulin Solution in the Presence of Compound 2 and Citrate For a final volume of 100 mL of formulation, with a [compound 2]/[lispro insulin] mass ratio of 2.0 and a citrate concentration of 9.3 mM, the various reagents are added in the amounts specified below and in the following order:

| Lyophilized compound 2 | 730 mg |
| 100 IU/mL Humalog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.
The final pH is adjusted to 7.4±0.4.
The clear solution is filtered through a 0.22 µm membrane and stored at 4° C.

B12. Preparation of a 100 IU/mL Lispro Insulin Solution in the Presence of Compound 2 and the Polyanionic Compound 1

For a final volume of 100 mL of formulation, with a [compound 2]/[polyanionic compound 1]/[lispro insulin]

mass ratio of 2.0/2.0/1, the various reagents are added in the amounts specified below and in the following order:

| | |
|---|---|
| Lyophilized compound 2 | 730 mg |
| Lyophilized polyanionic compound 1 | 730 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B13. Preparation of a 100 IU/mL Lispro Insulin Solution in the Presence of Compound 2 and the Polyanionic Compound 1

For a final volume of 100 mL of formulation, with a [compound 2]/[polyanionic compound 1]/[lispro insulin] mass ratio of 2.0/5.5/1, the various reagents are added in the amounts specified below and in the following order:

| | |
|---|---|
| Lyophilized compound 2 | 730 mg |
| Lyophilized polyanionic compound 1 | 2000 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B14. Preparation of a 100 IU/mL Lispro Insulin Solution in the Presence of Compound 1

For a final volume of 100 mL of formulation, with a [compound 1]/[lispro insulin] mass ratio of 4, the various reagents are added in the amounts specified below:

| | |
|---|---|
| Compound 1 in lyophilized form | 1460 mg |
| 100 IU/mL Humalog ® commercial solution | 100 mL |

The final pH is adjusted to 7.4±0.4. The clear solution is filtered through a 0.22 µm membrane and stored at 4° C.

B15. Preparation of a 100 IU/mL Lispro Insulin Solution in the Presence of Compound 2

For a final volume of 100 mL of formulation, with a [compound 2]/[lispro insulin] mass ratio of 4, the various reagents are added in the amounts specified below:

| | |
|---|---|
| Compound 2 in lyophilized form | 1460 mg |
| 100 IU/mL Humalog ® commercial solution | 100 mL |

The final pH is adjusted to 7.4±0.4. The clear solution is filtered through a 0.22 µm membrane and stored at 4° C.

B16. Preparation of a 100 IU/mL Lispro Insulin Analog Solution in the Presence of Compound 1 and Sodium Tartrate For a final volume of 100 mL of formulation, with a [compound 1]/[lispro insulin] mass ratio of 2.0 and a sodium tartrate concentration of 80 mM, the various reagents are added in the amounts specified below:

| | |
|---|---|
| Compound 1 in lyophilized form | 730 mg |
| 100 IU/mL Humalog ® commercial solution | 100 mL |
| Sodium tartrate | 1.552 g |

For the tartrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B17. Preparation of a 100 IU/mL Lispro Insulin Solution in the Presence of Compound 1 and the Polyanionic Compound 1

For a final volume of 100 mL of formulation, with a [compound 1]/[polyanionic compound 1]/[lispro insulin] mass ratio of 2/4/1, the various reagents are added in the amounts specified below:

| | |
|---|---|
| Compound 1 in lyophilized form | 730 mg |
| Polyanionic compound 1 in lyophilized form | 1460 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B18. Preparation of a 100 IU/mL Lispro Insulin Solution in the Presence of Compound 1 and Sodium Triphosphate For a final volume of 100 mL of formulation, the various reagents are added in the amounts specified below:

| | |
|---|---|
| Compound 1 in lyophilized form | 730 mg |
| Sodium triphosphate | 184 mg |
| 100 IU/mL Humalog ® commercial solution | 100 mL |

For the triphosphate, use may be made of the acid form or the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B19. Preparation of a 100 IU/mL Lispro Insulin Analog Solution in the Presence of Compound 2 and Sodium Tartrate For a final volume of 100 mL of formulation, with a [compound 2]/[lispro insulin] mass ratio of 2.0 and a sodium tartrate concentration of 80 mM, the various reagents are added in the amounts specified below:

| | |
|---|---|
| Compound 2 in lyophilized form | 730 mg |
| 100 IU/mL Humalog ® commercial solution | 100 mL |
| Sodium tartrate | 1.552 g |

For the tartrate, use may be made of the acid form or the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B20. Preparation of a 100 IU/mL Lispro Insulin Solution in the Presence of Compound 2 and the Polyanionic Compound 1

For a final volume of 100 mL of formulation, with a [compound 2]/[polyanionic compound 1]/[lispro insulin] mass ratio of 2/4/1, the various reagents are added in the amounts specified below:

| | |
|---|---|
| Compound 2 in lyophilized form | 730 mg |
| Polyanionic compound 1 in lyophilized form | 1460 mg |
| 100 IU/mL Humalog ® commercial solution | 100 mL |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B21. Preparation of a 100 IU/mL Lispro Insulin Solution in the Presence of Compound 2 and Sodium Triphosphate For a final volume of 100 mL of formulation, the various reagents are added in the amounts specified below:

| | |
|---|---|
| Compound 2 in lyophilized form | 730 mg |
| Sodium triphosphate | 184 mg |
| 100 IU/mL Humalog ® commercial solution | 100 mL |

For the triphosphate, use may be made of the acid form or the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B22. Preparation of a 200 IU/mL Insulin Analog (Lispro Insulin) Solution

The commercial formulation of lispro insulin (Humalog®) was concentrated using Amicon Ultra-15 centrifugation tubes with a 3 kDa cut-off threshold. The Amicon tubes were first rinsed with 12 mL of deionized water. 12 mL of the commercial formulation were centrifuged for 35 minutes at 4000 g at 20° C. The volume of the retentate was measured and the concentration thus estimated. All the retentates were pooled and the overall concentration was estimated (>200 IU/mL).

The concentration of this concentrated lispro insulin solution was adjusted to 200 IU/mL by adding the commercial lispro insulin formulation (Humalog®). The concentrated lispro insulin formulation has the same concentrations of excipients (m-cresol, glycerol, phosphate) as the commercial formulation at 100 IU/mL.

The final pH is adjusted to 7.4±0.4. The clear solution is filtered through a 0.22 µm membrane and stored at 4° C.

B23. Preparation of a 200 IU/mL Lispro Insulin Solution in the Presence of Compound 1 and Citrate For a final volume of 100 mL of formulation, with a [compound 1]/[lispro insulin] mass ratio of 2, the various reagents are mixed in the amounts specified below:

| | |
|---|---|
| 200 IU/mL lispro insulin | 100 mL |
| Lyophilizate of compound 1 | 1460 mg |
| 1.188M sodium citrate solution | 1566 µL |

The final pH is adjusted to 7.4±0.4. The clear solution is filtered through a 0.22 µm membrane and stored at 4° C.

B24. Preparation of a 200 IU/mL Lispro Insulin Solution in the Presence of Compound 1 and the Polyanionic Compound 1

For a final volume of 100 mL of formulation, with a [compound 1]/[polyanionic compound 1]/[lispro insulin] mass ratio of 2/2/1, the various reagents are mixed in the amounts specified below:

| | |
|---|---|
| 200 IU/mL lispro insulin | 100 mL |
| Lyophilizate of compound 1 | 1460 mg |
| Lyophilizate of polyanionic compound 1 | 1460 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 µm membrane and stored at 4° C.

B25. Preparation of a 200 IU/mL Lispro Insulin Solution in the Presence of Compound 1 and the Polyanionic Compound 1

For a final volume of 100 mL of formulation, with a [compound 1]/[polyanionic compound 1]/[lispro insulin] mass ratio of 2/4/1, the various reagents are mixed in the amounts specified below:

| | |
|---|---|
| 200 IU/mL lispro insulin | 100 mL |
| Lyophilizate of compound 1 | 1460 mg |
| Lyophilizate of polyanionic compound 1 | 2920 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B26. Preparation of a 200 IU/mL Lispro Insulin Solution in the Presence of Compound 2 and the Polyanionic Compound 1

For a final volume of 100 mL of formulation, with a [compound 2]/[polyanionic compound 1]/[lispro insulin] mass ratio of 2/4/1, the various reagents are mixed in the amounts specified below:

| | |
|---|---|
| 200 IU/mL lispro insulin | 100 mL |
| Lyophilizate of compound 2 | 1460 mg |
| Lyophilizate of polyanionic compound 1 | 2920 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B27. Preparation of a 100 IU/mL Human Insulin Solution in the Presence of Compound 1 and Tartrate For a final volume of 100 mL of formulation, with a [compound 1]/[human insulin] mass ratio of 2 and 80 mM of tartrate, the various reagents are mixed in the amounts specified below:

| | |
|---|---|
| 500 IU/mL human insulin | 20 mL |
| 36.01 mg/mL solution of compound 1 | 20.27 mL |
| 96.6 mM m-cresol/566 mM glycerol solution | 30 mL |
| Water | 28.95 mL |
| Sodium tartrate | 1.552 g |

For the tartrate, use may be made of the acid form or the basic form in the form of the sodium salt, the potassium salt or another salt that is compatible with an injectable formulation.

The final pH is 7.4±0.4. This clear solution is filtered through a 0.22 μm membrane and then placed at +4° C.

B28. Preparation of a 100 IU/mL Human Insulin Solution in the Presence of Compound 1 and Triphosphate For a final volume of 100 mL of formulation, the various reagents are mixed in the amounts specified below:

| | |
|---|---|
| 500 IU/mL human insulin | 20 mL |
| 36.01 mg/mL solution of compound 1 | 20.27 mL |
| 96.6 mM m-cresol/566 mM glycerol solution | 30 mL |
| Water | 28.95 mL |
| Sodium triphosphate | 184 mg |

For the triphosphate, use may be made of the acid form or the basic form in the form of the sodium salt, the potassium salt or another salt that is compatible with an injectable formulation.

The final pH is 7.4±0.4. This clear solution is filtered through a 0.22 μm membrane and then placed at +4° C.

B29. Preparation of a 100 IU/mL Human Insulin Solution in the Presence of Compound 2 and Tartrate For a final volume of 100 mL of formulation, with a [compound 2]/[human insulin] mass ratio of 2 and 80 mM of tartrate, the various reagents are mixed in the amounts specified below:

| | |
|---|---|
| 500 IU/mL human insulin | 20 mL |
| 36.01 mg/mL solution of compound 2 | 20.27 mL |
| 96.6 mM m-cresol/566 mM glycerol solution | 30 mL |
| Water | 28.95 mL |
| Sodium tartrate | 1.552 g |

For the tartrate, use may be made of the acid form or the basic form in the form of the sodium salt, the potassium salt or another salt that is compatible with an injectable formulation.

The final pH is 7.4±0.4.

This clear solution is filtered through a 0.22 μm membrane and then placed at +4° C.

B30. Preparation of a 100 IU/mL Human Insulin Solution in the Presence of Compound 2 and Triphosphate For a final volume of 100 mL of formulation, the various reagents are mixed in the amounts specified below:

| | |
|---|---|
| 500 IU/mL human insulin | 20 mL |
| 36.01 mg/mL solution of compound 2 | 20.27 mL |
| 96.6 mM m-cresol/566 mM glycerol solution | 30 mL |
| Water | 28.95 mL |
| Sodium triphosphate | 184 mg |

For the triphosphate, use may be made of the acid form or the basic form in the form of the sodium salt, the potassium salt or another salt that is compatible with an injectable formulation.

The final pH is 7.4±0.4. This clear solution is filtered through a 0.22 μm membrane and then placed at +4° C.

B31. Preparation of a 200 IU/mL Human Insulin Solution

The commercial formulation of human insulin (Humulin® R) was concentrated using Amicon Ultra-15 centrifugation tubes with a 3 kDa cut-off threshold. The Amicon tubes were first rinsed with 12 mL of deionized water. 12 mL of the commercial formulation were centrifuged for 35 minutes at 4000 g at 20° C. The volume of the retentate was measured and the concentration thus estimated. All the retentates were pooled and the overall concentration was estimated (>200 IU/mL).

The concentration of this concentrated human insulin solution was adjusted to 200 IU/mL by adding the commercial human insulin formulation (Humulin® R). The concentrated human insulin formulation has the same concentrations of excipients (m-cresol, glycerol) as the commercial formulation at 100 IU/mL.

The final pH is adjusted to 7.4±0.4. The clear solution is filtered through a 0.22 μm membrane and stored at 4° C.

B32. Preparation of a 200 IU/mL Human Insulin Solution in the Presence of Compound 1 and Citrate For a final volume of 100 mL of formulation, with a [compound 1]/[human insulin] mass ratio of 2, the various reagents are mixed in the amounts specified below:

| | |
|---|---|
| 200 IU/mL human insulin | 100 mL |
| Lyophilizate of compound 1 | 1460 mg |
| 1.188M sodium citrate solution | 1566 μL |

The final pH is adjusted to 7.4±0.4. The clear solution is filtered through a 0.22 μm membrane and stored at 4° C.

B33. Preparation of a 200 IU/mL Human Insulin Solution in the Presence of Compound 1 and the Polyanionic Compound 1

For a final volume of 100 mL of formulation, with a [compound 1]/[polyanionic compound 1]/[human insulin] mass ratio of 2/2/1, the various reagents are mixed in the amounts specified below:

| | |
|---|---|
| 200 IU/mL human insulin | 100 mL |
| Lyophilizate of compound 1 | 1460 mg |
| Lyophilizate of polyanionic compound 1 | 1460 mg |

The final pH is adjusted to 7.4±0.4. The clear solution is filtered through a 0.22 μm membrane and stored at 4° C.

B34. Preparation of a 200 IU/mL Human Insulin Solution in the Presence of Compound 1 and the Polyanionic Compound 1

For a final volume of 100 mL of formulation, with a [compound 1]/[polyanionic compound 1]/[human insulin] mass ratio of 2/4/1, the various reagents are mixed in the amounts specified below:

| | |
|---|---|
| 200 IU/mL human insulin | 100 mL |
| Lyophilizate of compound 1 | 1460 mg |
| Lyophilizate of polyanionic compound 1 | 2920 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B35. Preparation of a 200 IU/mL Human Insulin Solution in the Presence of Compound 2 and Citrate For a final volume of 100 mL of formulation, with a [compound 2]/[human insulin] mass ratio of 2, the various reagents are mixed in the amounts specified below:

| | |
|---|---|
| 200 IU/mL human insulin | 100 mL |
| Lyophilizate of compound 2 | 1460 mg |
| 1.188M sodium citrate solution | 1566 μL |

The final pH is adjusted to 7.4±0.4. The clear solution is filtered through a 0.22 μm membrane and stored at 4° C.

B36. Preparation of a 200 IU/mL Human Insulin Solution in the Presence of Compound 2 and the Polyanionic Compound 1

For a final volume of 100 mL of formulation, with a [compound 2]/[polyanionic compound 1]/[human insulin] mass ratio of 2/2/1, the various reagents are mixed in the amounts specified below:

| | |
|---|---|
| 200 IU/mL human insulin | 100 mL |
| Lyophilizate of compound 2 | 1460 mg |
| Lyophilizate of polyanionic compound 1 | 1460 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B37. Preparation of a 200 IU/mL Human Insulin Solution in the Presence of Compound 2 and the Polyanionic Compound 1

For a final volume of 100 mL of formulation, with a [compound 2]/[polyanionic compound 1]/[human insulin] mass ratio of 2/4/1, the various reagents are mixed in the amounts specified below:

| | |
|---|---|
| 200 IU/mL human insulin | 100 mL |
| Lyophilizate of compound 2 | 1460 mg |
| Lyophilizate of polyanionic compound 1 | 2920 mg |

The polyanionic compound 1 may be used in the acid form or the basic form in the form of the sodium salt, the potassium salt or another salt that is compatible with an injectable formulation.

The final pH is adjusted to 7.4±0.4. The clear solution is filtered through a 0.22 μm membrane and stored at 4° C.

B38. Preparation of a 100 IU/mL Human Insulin Solution in the Presence of Compound 2 and Citrate For a final volume of 100 mL of formulation, with a [compound 2]/[human insulin] mass ratio of 2 and 9.3 mM of citrate, the various reagents are mixed in the amounts specified below:

| | |
|---|---|
| 500 IU/mL human insulin | 20 mL |
| 36.01 mg/mL solution of compound 2 | 20.27 mL |
| 96.6 mM m-cresol/566 mM glycerol solution | 30 mL |
| Water | 28.95 mL |
| 1.188M sodium citrate solution | 783 μL |

For the citrate, use may be made of the acid form or the basic form in the form of the sodium salt, the potassium salt or another salt that is compatible with an injectable formulation.

The final pH is 7.4±0.4. This clear solution is filtered through a 0.22 μm membrane and then placed at +4° C.

B39. Preparation of a 100 IU/mL Human Insulin Solution in the Presence of Compound 1 and Citrate For a final volume of 100 mL of formulation, with a [compound 1]/[human insulin] mass ratio of 2 and 9.3 mM of citrate, the various reagents are mixed in the amounts specified below:

| | |
|---|---|
| 500 IU/mL human insulin | 20 mL |
| 36.01 mg/mL solution of compound 1 | 27 mL |
| 96.6 mM m-cresol/566 mM glycerol solution | 30 mL |
| Water | 28.95 mL |
| 1.188M sodium citrate solution | 783 µL |

For the citrate, use may be made of the acid form or the basic form in the form of the sodium salt, the potassium salt or another salt that is compatible with an injectable formulation.

The final pH is 7.4±0.4. This clear solution is filtered through a 0.22 µm membrane and then placed at +4° C.

B40. Preparation of a 100 IU/mL Aspart Insulin Solution in the Presence of Compound 1 and Citrate For a final volume of 100 mL of formulation, with a [compound 1]/[aspart insulin] mass ratio of 2.0 and a citrate concentration of 9.3 mM, the various reagents are added in the amounts specified below and in the following order:

| | |
|---|---|
| Lyophilized compound 1 | 730 mg |
| 100 IU/mL Novolog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B41. 100 IU/mL Solution of Rapid Insulin Analog Apidra®

This solution is a commercial solution of glulisine insulin from Sanofi-Aventis sold under the name Apidra®. This product is a rapid insulin analog.

B42. Preparation of a 100 IU/mL Glulisine Insulin Solution in the Presence of Compound 1 and Citrate For a final volume of 100 mL of formulation, with a [compound 1]/[glulisine insulin] mass ratio of 2.0 and a citrate concentration of 9.3 mM, the various reagents are added in the amounts specified below and in the following order:

| | |
|---|---|
| Lyophilized compound 1 | 730 mg |
| 100 IU/mL Apidra ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B43. Preparation of a 100 IU/mL Aspart Insulin Solution in the Presence of Compound 2 and Citrate For a final volume of 100 mL of formulation, with a [compound 2]/[aspart insulin] mass ratio of 2.0 and a citrate concentration of 9.3 mM, the various reagents are added in the amounts specified below and in the following order:

| | |
|---|---|
| Lyophilized compound 2 | 730 mg |
| 100 IU/mL Novolog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B44. Preparation of a 100 IU/mL Glulisine Insulin Solution in the Presence of Compound 2 and Citrate For a final volume of 100 mL of formulation, with a [compound 2]/[glulisine insulin] mass ratio of 2.0 and a citrate concentration of 9.3 mM, the various reagents are added in the amounts specified below and in the following order:

| | |
|---|---|
| Lyophilized compound 2 | 730 mg |
| 100 IU/mL Apidra ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B45. Preparation of a 100 IU/mL Lispro Insulin Solution in the Presence of Compound 5 and Citrate For a final volume of 100 mL of formulation, with a [compound 5]/[lispro insulin] mass ratio of 2.0 and a citrate concentration of 9.3 mM, the various reagents are added in the amounts specified below and in the following order:

| | |
|---|---|
| Lyophilized compound 5 | 730 mg |
| 100 IU/mL Humalog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B46. Preparation of a 100 IU/mL Lispro Insulin Solution in the Presence of Compound 6 and Citrate For a final volume of 100 mL of formulation, with a [compound 6]/[lispro insulin] mass ratio of 2.0 and a citrate concentration of 9.3 mM, the various reagents are added in the amounts specified below and in the following order:

| | |
|---|---|
| Lyophilized compound 6 | 730 mg |
| 100 IU/mL Humalog ® commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B47. Preparation of a 100 IU/mL Lispro Insulin Solution in the Presence of Compound 7 and Citrate For a final volume of 100 mL of formulation, with a [compound 7]/[lispro insulin] mass ratio of 2.0 and a citrate concentration of 9.3 mM, the various reagents are added in the amounts specified below and in the following order:

| | |
|---|---|
| Lyophilized compound 7 | 730 mg |
| 100 IU/mL Humalog ® commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B48. Preparation of a 100 IU/mL Lispro Insulin Solution in the Presence of Compound 8 and Citrate For a final volume of 100 mL of formulation, with a [compound 8]/[lispro insulin] mass ratio of 2.0 and a citrate concentration of 9.3 mM, the various reagents are added in the amounts specified below and in the following order:

| | |
|---|---|
| Lyophilized compound 8 | 730 mg |
| 100 IU/mL Humalog ® commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B49. Preparation of a 100 IU/mL Lispro Insulin Solution in the Presence of Compound 9 and Citrate For a final volume of 100 mL of formulation, with a [compound 9]/[lispro insulin] mass ratio of 2.0 and a citrate concentration of 9.3 mM, the various reagents are added in the amounts specified below and in the following order:

| | |
|---|---|
| Lyophilized compound 9 | 730 mg |
| 100 IU/mL Humalog ® commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

B50. Preparation of a 100 IU/mL Human Insulin Solution in the Presence of Compound 5 and Citrate For a final volume of 100 mL of formulation, with a [compound 5]/[human insulin] mass ratio of 2.0 and a citrate concentration of 9.3 mM, the various reagents are added in the amounts specified below and in the following order:

| | |
|---|---|
| Lyophilized compound 5 | 730 mg |
| 100 IU/mL Humulin ® R commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 μm membrane and stored at 4° C.

B51. Preparation of a 100 IU/mL Human Insulin Solution in the Presence of Compound 6 and Citrate For a final volume of 100 mL of formulation, with a [compound 6]/[human insulin] mass ratio of 2.0 and a citrate concentration of 9.3 mM, the various reagents are added in the amounts specified below and in the following order:

| | |
|---|---|
| Lyophilized compound 6 | 730 mg |
| 100 IU/mL Humulin ® R commercial solution | 100 mL |
| 1.188M sodium citrate solution | 783 μL |

For the citrate, use may be made of the acid form or the basic form in the form of the sodium salt, the potassium salt or another salt that is compatible with an injectable formulation.

B52. Preparation of a 100 IU/mL Human Insulin Solution in the Presence of Compound 7 and Citrate For a final volume of 100 mL of formulation, with a [compound 7]/[human insulin] mass ratio of 2.0 and a citrate concentration of 9.3 mM, the various reagents are added in the amounts specified below and in the following order:

| | |
|---|---|
| Lyophilized compound 7 | 730 mg |
| 100 IU/mL Humulin ® R commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B53. Preparation of a 100 IU/mL Human Insulin Solution in the Presence of Compound 8 and Citrate For a final volume of 100 mL of formulation, with a [compound 8]/[human insulin] mass ratio of 2.0 and a citrate concentration of 9.3 mM, the various reagents are added in the amounts specified below and in the following order:

| | |
|---|---|
| Lyophilized compound 8 | 730 mg |
| 100 IU/mL Humulin ® R commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B54. Preparation of a 100 IU/mL Human Insulin Solution in the Presence of Compound 9 and Citrate For a final volume of 100 mL of formulation, with a [compound 9]/[human insulin] mass ratio of 2.0 and a citrate concentration of 9.3 mM, the various reagents are added in the amounts specified below and in the following order:

| | |
|---|---|
| Lyophilized compound 9 | 730 mg |
| 100 IU/mL Humulin ® R commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B55. Preparation of a 100 IU/mL Human Insulin Solution in the Presence of Compound 2

For a final volume of 100 mL of formulation, with a [compound 2]/[human insulin] mass ratio of 2.0, the various reagents are added in the amounts specified below and in the following order:

| | |
|---|---|
| Lyophilized compound 2 | 730 mg |
| 100 IU/mL Humulin ® R commercial solution | 100 mL |

The final pH is adjusted to 7.4±0.4.

The clear solution is filtered through a 0.22 µm membrane and stored at 4° C.

B56. Preparation of a 100 IU/mL Human Insulin Solution in the Presence of Compound 7

For a final volume of 100 mL of formulation, with a [compound 7]/[human insulin] mass ratio of 2.0, the various reagents are added in the amounts specified below and in the following order:

| | |
|---|---|
| Lyophilized compound 7 | 730 mg |
| 100 IU/mL Humulin ® R commercial solution | 100 mL |

The final pH is adjusted to 7.4±0.4.

The clear solution is filtered through a 0.22 µm membrane and stored at 4° C.

B57. Preparation of a 100 IU/mL Lispro Insulin Solution in the Presence of Compound 10 and Citrate For a final volume of 100 mL of formulation, with a [compound 10]/[lispro insulin] mass ratio of 2.0 and a citrate concentration of 9.3 mM, the various reagents are added in the amounts specified below and in the following order:

| | |
|---|---|
| Lyophilized compound 10 | 730 mg |
| 100 IU/mL Humalog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B58. Preparation of a 100 IU/mL Lispro Insulin Solution in the Presence of Compound 11 and Citrate For a final volume of 100 mL of formulation, with a [compound 11]/[lispro insulin] mass ratio of 2.0 and a citrate concentration of 9.3 mM, the various reagents are added in the amounts specified below and in the following order:

| | |
|---|---|
| Lyophilized compound 11 | 730 mg |
| 100 IU/mL Humalog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

B59. Preparation of a 100 IU/mL Human Insulin Solution in the Presence of Compound 10 and Citrate For a final volume of 100 mL of formulation, with a [compound 10]/[human insulin] mass ratio of 2.0 and a citrate concentration of 9.3 mM, the various reagents are added in the amounts specified below and in the following order:

| | |
|---|---|
| Lyophilized compound 10 | 730 mg |
| 100 IU/mL Humulin ® R commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B60. Preparation of a 100 IU/mL Human Insulin Solution in the Presence of Compound 11 and Citrate For a final volume of 100 mL of formulation, with a [compound 11]/[human insulin] mass ratio of 2.0 and a citrate concentration of 9.3 mM, the various reagents are added in the amounts specified below and in the following order:

| | |
|---|---|
| Lyophilized compound 11 | 730 mg |
| 100 IU/mL Humulin ® R commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B61. Preparation of a 200 IU/mL Aspart Insulin Solution

The commercial formulation of aspart insulin (Novolog®) was concentrated using Amicon Ultra-15 centrifugation tubes with a 3 kDa cut-off threshold. The Amicon tubes were first rinsed with 12 mL of deionized water. 12 mL of the commercial formulation were centrifuged for 35 minutes at 4000 g at 20° C. The volume of the retentate was measured and the concentration thus estimated. All the retentates were pooled and the overall concentration was estimated (>200 IU/mL).

The concentration of this concentrated aspart insulin solution was adjusted to 200 IU/mL by adding the commercial aspart insulin formulation (Novolog®). The concentrated aspart insulin formulation has the same concentrations of excipients (m-cresol, glycerol) as the commercial formulation at 100 IU/mL.

By modifying the centrifugation time and the final dilution with the commercial formulation, it is possible to prepare in the same manner aspart insulin formulations at 300, 400 or 500 IU/mL.

The final pH is adjusted to 7.4±0.4. The clear solution is filtered through a 0.22 µm membrane and stored at 4° C.

B62. Preparation of a 200 IU/mL Glulisine Insulin Solution

The commercial formulation of glulisine insulin (Apidra®) was concentrated using Amicon Ultra-15 centrifugation tubes with a 3 kDa cut-off threshold. The Amicon tubes were first rinsed with 12 mL of deionized water. 12 mL of the commercial formulation were centrifuged for 35 minutes at 4000 g at 20° C. The volume of the retentate was measured and the concentration thus estimated. All the retentates were pooled and the overall concentration was estimated (>200 IU/mL).

The concentration of this concentrated glulisine insulin solution was adjusted to 200 IU/mL by adding the commercial glulisine insulin formulation (Apidra®). The concentrated glulisine insulin formulation has the same concentrations of excipients (m-cresol, NaCl, TRIS) as the commercial formulation at 100 IU/mL.

By modifying the centrifugation time and the final dilution with the commercial formulation, it is possible to prepare in the same manner glulisine insulin formulations at 300, 400 or 500 IU/mL.

The final pH is adjusted to 7.4±0.4. The clear solution is filtered through a 0.22 µm membrane and stored at 4° C.

B63. Preparation of a 200 IU/mL Aspart Insulin Solution in the Presence of Compound 1 at 14.6 mg/mL and 18.6 mM Citrate For a final volume of 100 mL of formulation, with a [compound 1]/[aspart insulin] mass ratio of 2.0, the various reagents are mixed in the amounts specified below and in the following order:

| | |
|---|---|
| Lyophilizate of compound 1 | 1460 mg |
| 200 IU/mL aspart insulin | 100 mL |
| 1.188M sodium citrate solution | 1566 µL |

The final pH is adjusted to 7.4±0.4. The clear solution is filtered through a 0.22 µm membrane and stored at 4° C.

B64. Preparation of a Human Insulin, Lispro Insulin, Aspart Insulin or Glulisine Insulin Solution at 300, 400 and 500 IU/mL Concentrated formulations of human insulin, lispro insulin, aspart insulin or glulisine insulin at 300 IU/mL, 400 IU/mL or 500 IU/mL (and also at all intermediate concentrations) are prepared on the basis of the protocol of example B62 relating to the preparation of a 200 IU/mL glulisine insulin solution. The commercial insulin formulation is concentrated using Amicon Ultra-15 centrifugation tubes with a 3 kDa cut-off threshold. The Amicon tubes are first rinsed with 12 mL of deionized water. 12 mL of the commercial formulation are centrifuged at 4000 g at 20° C. By modifying the centrifugation time, it is possible to adjust the final concentration of insulin in the formulation. The volume of the retentate is measured and the concentration is thus estimated. All the retentates are pooled and the overall concentration is estimated (>300, 400 or 500 IU/mL).

The concentration of this concentrated insulin solution is adjusted to the desired concentration (e.g. 300 IU/mL, 400 IU/mL or 500 IU/mL) by addition of the insulin formulation (Humulin® R, Novolog®, Humalog® or Apidra®). The concentrated insulin formulation has the same concentrations of excipients as the commercial formulation at 100 IU/mL.

The final pH is adjusted to 7.4±0.4. The clear solution is filtered through a 0.22 µm membrane and stored at 4° C.

B65. Preparation of a 200 IU/mL Glulisine Insulin Solution in the Presence of Compound 1 and Citrate For a final volume of 100 mL of formulation, with a [compound 1]/[glulisine insulin] mass ratio of 2, the various reagents are mixed in the amounts specified below and in the following order:

| | |
|---|---|
| Lyophilizate of compound 1 | 1460 mg |
| 200 IU/mL glulisine insulin | 100 mL |
| 1.188M sodium citrate solution | 1566 µL |

The final pH is adjusted to 7.4±0.4. The clear solution is filtered through a 0.22 µm membrane and stored at 4° C.

B66. Preparation of a 300 IU/mL Aspart Insulin Solution in the Presence of Compound 1 and Citrate For a final volume of 100 mL of formulation, with a [compound 1]/[aspart insulin] mass ratio of 2.0, the various reagents are mixed in the amounts specified below:

| | |
|---|---|
| 300 IU/mL aspart insulin | 100 mL |
| Lyophilizate of compound 1 | 2190 mg |
| Sodium citrate | 720 mg |

The final pH is adjusted to 7.4±0.4. The clear solution is filtered through a 0.22 µm membrane and stored at 4° C.

B67. Preparation of a 300 IU/mL Glulisine Insulin Solution in the Presence of Compound 1 and Citrate For a final volume of 100 mL of formulation, with a [compound 1]/[glulisine insulin] mass ratio of 2.0, the various reagents are mixed in the amounts specified below:

| | |
|---|---|
| 300 IU/mL glulisine insulin | 100 mL |
| Lyophilizate of compound 1 | 2190 mg |
| Sodium citrate | 720 mg |

The final pH is adjusted to 7.4±0.4. The clear solution is filtered through a 0.22 µm membrane and stored at 4° C.

B68. Preparation of a 400 IU/mL Aspart Insulin Solution in the Presence of Compound 1 and Citrate For a final volume of 100 mL of formulation, with a [compound 1]/[aspart insulin] mass ratio of 2, the various reagents are mixed in the amounts specified below:

| | |
|---|---|
| 400 IU/mL aspart insulin | 100 mL |
| Lyophilizate of compound 1 | 2920 mg |
| Sodium citrate | 960 mg |

The final pH is adjusted to 7.4±0.4. The clear solution is filtered through a 0.22 µm membrane and stored at 4° C.

B69. Preparation of a 400 IU/mL Glulisine Insulin Solution in the Presence of Compound 1 and Citrate For a final volume of 100 mL of formulation, with a [compound 1]/[glulisine insulin] mass ratio of 2.0, the various reagents are mixed in the amounts specified below:

| | |
|---|---|
| 400 IU/mL glulisine insulin | 100 mL |
| Lyophilizate of compound 1 | 2920 mg |
| Sodium citrate | 960 mg |

The final pH is adjusted to 7.4±0.4. The clear solution is filtered through a 0.22 µm membrane and stored at 4° C.

B70. Preparation of a 500 IU/mL Aspart Insulin Solution in the Presence of Compound 1 and Citrate For a final volume of 100 mL of formulation, with a [compound 1]/[aspart insulin] mass ratio of 2.0, the various reagents are mixed in the amounts specified below:

| | |
|---|---|
| 500 IU/mL aspart insulin | 100 mL |
| Lyophilizate of compound 1 | 3650 mg |
| Sodium citrate | 1200 mg |

The final pH is adjusted to 7.4±0.4. The clear solution is filtered through a 0.22 µm membrane and stored at 4° C.

B71. Preparation of a 500 IU/mL Glulisine Insulin Solution in the Presence of Compound 1 and Citrate For a final volume of 100 mL of formulation, with a [compound 1]/[glulisine insulin] mass ratio of 2.0, the various reagents are mixed in the amounts specified below:

| | |
|---|---|
| 500 IU/mL glulisine insulin | 100 mL |
| Lyophilizate of compound 1 | 3650 mg |
| Sodium citrate | 1200 mg |

The final pH is adjusted to 7.4±0.4. The clear solution is filtered through a 0.22 µm membrane and stored at 4° C.

B72. Preparation of a 500 IU/mL Glulisine insulin Solution in the Presence of Compound 1 and Citrate For a final volume of 100 mL of formulation, with a [compound 1]/[human insulin] mass ratio of 2.0, the various reagents are mixed in the amounts specified below:

| | |
|---|---|
| 300 IU/mL human insulin | 100 mL |
| Lyophilizate of compound 1 | 2190 mg |
| Sodium citrate | 720 mg |

The final pH is adjusted to 7.4±0.4. The clear solution is filtered through a 0.22 µm membrane and stored at 4° C.

B73. Preparation of a 300 IU/mL Lispro Insulin Solution in the Presence of Compound 1 and Citrate For a final volume of 100 mL of formulation, with a [compound 1]/[lispro insulin] mass ratio of 2.0, the various reagents are mixed in the amounts specified below:

| | |
|---|---|
| 300 IU/mL lispro insulin | 100 mL |
| Lyophilizate of compound 1 | 2190 mg |
| Sodium citrate | 720 mg |

The final pH is adjusted to 7.4±0.4. The clear solution is filtered through a 0.22 µm membrane and stored at 4° C.

B74. Preparation of a 400 IU/mL Human Insulin Solution in the Presence of Compound 1 and Citrate For a final volume of 100 mL of formulation, with a [compound 1]/[human insulin] mass ratio of 2.0, the various reagents are mixed in the amounts specified below:

| | |
|---|---|
| 400 IU/mL human insulin | 100 mL |
| Lyophilizate of compound 1 | 2920 mg |
| Sodium citrate | 960 mg |

The final pH is adjusted to 7.4±0.4. The clear solution is filtered through a 0.22 µm membrane and stored at 4° C.

B75. Preparation of a 400 IU/mL Lispro Insulin Solution in the Presence of Compound 1 and Citrate For a final volume of 100 mL of formulation, with a [compound 1]/[lispro insulin] mass ratio of 2.0, the various reagents are mixed in the amounts specified below:

| | |
|---|---|
| 400 IU/mL lispro insulin | 100 mL |
| Lyophilizate of compound 1 | 2920 mg |
| Sodium citrate | 960 mg |

The final pH is adjusted to 7.4±0.4. The clear solution is filtered through a 0.22 µm membrane and stored at 4° C.

B76. Preparation of a 500 IU/mL Human Insulin Solution in the Presence of Compound 1 and Citrate For a final volume of 100 mL of formulation, with a [compound 1]/[human insulin] mass ratio of 2.0, the various reagents are mixed in the amounts specified below:

| | |
|---|---|
| 500 IU/mL human insulin | 100 mL |
| Lyophilizate of compound 1 | 3650 mg |
| Sodium citrate | 1200 mg |

The final pH is adjusted to 7.4±0.4. The clear solution is filtered through a 0.22 µm membrane and stored at 4° C.

B77. Preparation of a 500 IU/mL Lispro Insulin Solution in the Presence of Compound 1 and Citrate For a final volume of 100 mL of formulation, with a [compound 1]/[lispro insulin] mass ratio of 2.0, the various reagents are mixed in the amounts specified below:

| | |
|---|---|
| 500 IU/mL lispro insulin | 100 mL |
| Lyophilizate of compound 1 | 3650 mg |
| Sodium citrate | 1200 mg |

The final pH is adjusted to 7.4±0.4. The clear solution is filtered through a 0.22 µm membrane and stored at 4° C.

B78. Preparation of a 200 IU/mL Lispro Insulin Solution in the Presence of Compound 2 and Citrate For a final volume of 100 mL of formulation, with a [compound 2]/[lispro insulin] mass ratio of 2.0, the various reagents are mixed in the amounts specified below:

| | |
|---|---|
| 200 IU/mL lispro insulin | 100 mL |
| Lyophilizate of compound 2 | 1460 mg |
| 1.188M sodium citrate solution | 1566 µL |

The final pH is adjusted to 7.4±0.4. The clear solution is filtered through a 0.22 µm membrane and stored at 4° C.

B79. Preparation of a 200 IU/mL Aspart Insulin Solution in the Presence of Compound 2 and Citrate For a final volume of 100 mL of formulation, with a [compound 2]/[aspart insulin] mass ratio of 2.0, the various reagents are mixed in the amounts specified below:

| | |
|---|---|
| 200 IU/mL aspart insulin | 100 mL |
| Lyophilizate of compound 2 | 1460 mg |
| 1.188M sodium citrate solution | 1566 µL |

The final pH is adjusted to 7.4±0.4. The clear solution is filtered through a 0.22 μm membrane and stored at 4° C.

B80. Preparation of a 200 IU/mL Glulisine Insulin Solution in the Presence of Compound 2 and Citrate For a final volume of 100 mL of formulation, with a [compound 2]/[glulisine insulin] mass ratio of 2.0, the various reagents are mixed in the amounts specified below:

| | |
|---|---|
| 200 IU/mL glulisine insulin | 100 mL |
| Lyophilizate of compound 2 | 1460 mg |
| 1.188M sodium citrate solution | 1566 μL |

The final pH is adjusted to 7.4±0.4. The clear solution is filtered through a 0.22 μm membrane and stored at 4° C.

B81. Preparation of a 300 IU/mL Aspart Insulin Solution in the Presence of Compound 2 and Citrate For a final volume of 100 mL of formulation, with a [compound 2]/[aspart insulin] mass ratio of 2.0, the various reagents are mixed in the amounts specified below:

| | |
|---|---|
| 300 IU/mL aspart insulin | 100 mL |
| Lyophilizate of compound 2 | 2190 mg |
| Sodium citrate | 720 mg |

The final pH is adjusted to 7.4±0.4. The clear solution is filtered through a 0.22 μm membrane and stored at 4° C.

B82. Preparation of a 300 IU/mL Glulisine Insulin Solution in the Presence of Compound 2 and Citrate For a final volume of 100 mL of formulation, with a [compound 2]/[glulisine insulin] mass ratio of 2.0, the various reagents are mixed in the amounts specified below:

| | |
|---|---|
| 300 IU/mL glulisine insulin | 100 mL |
| Lyophilizate of compound 2 | 2190 mg |
| Sodium citrate | 720 mg |

The final pH is adjusted to 7.4±0.4. The clear solution is filtered through a 0.22 μm membrane and stored at 4° C.

B83. Preparation of a 400 IU/mL Aspart Insulin Solution in the Presence of Compound 2 and Citrate For a final volume of 100 mL of formulation, with a [compound 2]/[aspart insulin] mass ratio of 2.0, the various reagents are mixed in the amounts specified below:

| | |
|---|---|
| 400 IU/mL aspart insulin | 100 mL |
| Lyophilizate of compound 2 | 2920 mg |
| Sodium citrate | 960 mg |

The final pH is adjusted to 7.4±0.4. The clear solution is filtered through a 0.22 μm membrane and stored at 4° C.

B84. Preparation of a 400 IU/mL Glulisine Insulin Solution in the Presence of Compound 2 and Citrate For a final volume of 100 mL of formulation, with a [compound 2]/[glulisine insulin] mass ratio of 2.0, the various reagents are mixed in the amounts specified below:

| | |
|---|---|
| 400 IU/mL glulisine insulin | 100 mL |
| Lyophilizate of compound 2 | 2920 mg |
| Sodium citrate | 960 mg |

The final pH is adjusted to 7.4±0.4. The clear solution is filtered through a 0.22 μm membrane and stored at 4° C.

B85. Preparation of a 500 IU/mL Aspart Insulin Solution in the Presence of Compound 2 and Citrate For a final volume of 100 mL of formulation, with a [compound 2]/[aspart insulin] mass ratio of 2.0, the various reagents are mixed in the amounts specified below:

| | |
|---|---|
| 500 IU/mL aspart insulin | 100 mL |
| Lyophilizate of compound 2 | 3650 mg |
| Sodium citrate | 1200 mg |

The final pH is adjusted to 7.4±0.4. The clear solution is filtered through a 0.22 μm membrane and stored at 4° C.

B86. Preparation of a 500 IU/mL Glulisine Insulin Solution in the Presence of Compound 2 and Citrate For a final volume of 100 mL of formulation, with a [compound 2]/[glulisine insulin] mass ratio of 2.0, the various reagents are mixed in the amounts specified below:

| | |
|---|---|
| 500 IU/mL glulisine insulin | 100 mL |
| Lyophilizate of compound 2 | 3650 mg |
| Sodium citrate | 1200 mg |

The final pH is adjusted to 7.4±0.4. The clear solution is filtered through a 0.22 μm membrane and stored at 4° C.

B87. Preparation of a 500 IU/mL Glulisine Insulin Solution in the Presence of Compound 2 and Citrate For a final volume of 100 mL of formulation, with a [compound 2]/[human insulin] mass ratio of 2, the various reagents are mixed in the amounts specified below:

| | |
|---|---|
| 300 IU/mL human insulin | 100 mL |
| Lyophilizate of compound 2 | 2190 mg |
| Sodium citrate | 720 mg |

B88. Preparation of a 300 IU/mL Lispro Insulin Solution in the Presence of Compound 2 and Citrate For a final volume of 100 mL of formulation, with a [compound 2]/[lispro insulin] mass ratio of 2.0, the various reagents are mixed in the amounts specified below:

| | |
|---|---|
| 300 IU/mL lispro insulin | 100 mL |
| Lyophilizate of compound 2 | 2190 mg |
| Sodium citrate | 720 mg |

The final pH is adjusted to 7.4±0.4. The clear solution is filtered through a 0.22 µm membrane and stored at 4° C.

B89. Preparation of a 400 IU/mL Human Insulin Solution in the Presence of Compound 2 and Citrate For a final volume of 100 mL of formulation, with a [compound 2]/[human insulin] mass ratio of 2.0, the various reagents are mixed in the amounts specified below:

| | |
|---|---|
| 400 IU/mL human insulin | 100 mL |
| Lyophilizate of compound 2 | 2920 mg |
| Sodium citrate | 960 mg |

The final pH is adjusted to 7.4±0.4. The clear solution is filtered through a 0.22 µm membrane and stored at 4° C.

B90. Preparation of a 400 IU/mL Lispro Insulin Solution in the Presence of Compound 2 and Citrate For a final volume of 100 mL of formulation, with a [compound 2]/[lispro insulin] mass ratio of 2.0, the various reagents are mixed in the amounts specified below:

| | |
|---|---|
| 400 IU/mL lispro insulin | 100 mL |
| Lyophilizate of compound 2 | 2920 mg |
| Sodium citrate | 960 mg |

The final pH is adjusted to 7.4±0.4. The clear solution is filtered through a 0.22 µm membrane and stored at 4° C.

B91. Preparation of a 500 IU/mL Human Insulin Solution in the Presence of Compound 2 and Citrate For a final volume of 100 mL of formulation, with a [compound 2]/[human insulin] mass ratio of 2.0, the various reagents are mixed in the amounts specified below:

| | |
|---|---|
| 500 IU/mL human insulin | 100 mL |
| Lyophilizate of compound 2 | 3650 mg |
| Sodium citrate | 1200 mg |

The final pH is adjusted to 7.4±0.4. The clear solution is filtered through a 0.22 µm membrane and stored at 4° C.

B92. Preparation of a 500 IU/mL Lispro Insulin Solution in the Presence of Compound 2 and Citrate For a final volume of 100 mL of formulation, with a [compound 2]/[lispro insulin] mass ratio of 2.0, the various reagents are added in the amounts specified below:

| | |
|---|---|
| 500 IU/mL lispro insulin | 100 mL |
| Lyophilizate of compound 2 | 3650 mg |
| Sodium citrate | 1200 mg |

The final pH is adjusted to 7.4±0.4. The clear solution is filtered through a 0.22 µm membrane and stored at 4° C.

B93. Preparation of a 100 IU/mL Lispro Insulin Solution in the Presence of Compound 3 and Citrate For a final volume of 100 mL of formulation, with a [compound 3]/[lispro insulin] mass ratio of 2.0 and a citrate concentration of 9.3 mM, the various reagents are added in the amounts specified below and in the following order:

| | |
|---|---|
| Lyophilized compound 3 | 730 mg |
| 100 IU/mL Humalog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B94. Preparation of a 100 IU/mL Lispro Insulin Solution in the Presence of Compound 4 and Citrate For a final volume of 100 mL of formulation, with a [compound 4]/[lispro insulin] mass ratio of 2.0 and a citrate concentration of 9.3 mM, the various reagents are added in the amounts specified below and in the following order:

| | |
|---|---|
| Lyophilized compound 4 | 730 mg |
| 100 IU/mL Humalog ® commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B95. Preparation of a 100 IU/mL Human Insulin Solution in the Presence of Compound 3 and Citrate For a final volume of 100 mL of formulation, with a [compound 3]/[human insulin] mass ratio of 2.0 and a citrate concentration of 9.3 mM, the various reagents are added in the amounts specified below and in the following order:

| Lyophilized compound 3 | 730 mg |
|---|---|
| 100 IU/mL Humulin ® R commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

B96. Preparation of a 100 IU/mL Human Insulin Solution in the Presence of Compound 4 and Citrate For a final volume of 100 mL of formulation, with a [compound 4]/[human insulin] mass ratio of 2.0 and a citrate concentration of 9.3 mM, the various reagents are added in the amounts specified below and in the following order:

| Lyophilized compound 4 | 730 mg |
|---|---|
| 100 IU/mL Humulin ® R commercial solution | 100 mL |
| 1.188M sodium citrate solution | 783 µL |

For the citrate, use may be made of the acid form or the basic form in the form of the sodium salt, the potassium salt or another salt that is compatible with an injectable formulation.

The final pH is adjusted to 7.4±0.4.

The clear solution is filtered through a 0.22 µm membrane and stored at 4° C.

C Pharmacodynamics and Pharmacokinetics

C1: Protocol for Measuring the Pharmacodynamics of the Insulin Solutions

Twelve domestic pigs weighing about 50 kg, catheterized beforehand in the jugular vein, are fasted for 2.5 hours before the start of the experiment. In the hour preceding the injection of insulin, three blood samples are taken in order to determine the basal level of glucose and of insulin.

The injection of insulin at a dose of 0.09 IU/kg for lispro insulin and at a dose of 0.125 IU/kg for human insulin and aspart insulin is performed subcutaneously into the neck, under the animal's ear, using a Novopen insulin pen equipped with a 31 G needle.

Blood samples are then taken every 4 minutes for 20 minutes and then every 10 minutes up to 3 hours. After taking each sample, the catheter is rinsed with a dilute heparin solution.

A drop of blood is taken to determine the glycemia using a glucometer.

The glucose pharmacodynamic curves are then plotted and the time required to reach the minimum glucose level in the blood for each pig is determined and reported as the glucose Tmin. The mean of the glucose Tmin values is then calculated.

The remaining blood is collected in a dry tube and is centrifuged to isolate the serum. The insulin levels in the serum samples are measured via the sandwich ELISA immunoenzymatic method for each pig.

The pharmacokinetic curves are then plotted. The time required to reach the maximum insulin concentration in the serum for each pig is determined and reported as the insulin Tmax. The mean of the insulin Tmax values is then calculated.

C2: Pharmacodynamic and Pharmacokinetic Results for the Insulin Solutions of Examples B2 and B8

| Example | Insulin | Compound | Polyanionic compound | Number of pigs |
|---|---|---|---|---|
| B2 | Lispro | — | — | 11 |
| B8 | Lispro | 1 | Citrate 9.3 mM | 10 |

The pharmacodynamic results obtained with the formulations described in examples B2 and B8 are presented in FIG. 1. According to the invention, the analysis of these curves shows that the formulation of example B8 comprising compound 1 and citrate at 9.3 mM as excipient (curve plotted with the squares corresponding to example B8, glucose Tmin=30±11 min) makes it possible to obtain more rapid action than that obtained with the Humalog® commercial formulation of example B2 (curve plotted with the triangles corresponding to example B2, glucose Tmin=44±14 min).

The pharmacokinetic results obtained with the formulations described in examples B2 and B8 are presented in FIG. 2. According to the invention, the analysis of these curves shows that the formulation of example B8 comprising compound 1 and citrate at 9.3 mM as excipients (curve plotted with the squares corresponding to example B8, insulin Tmax=11±6 min) induces more rapid absorption of the lispro insulin than that of the Humalog® commercial formulation of example B2 (curve plotted with the triangles corresponding to example B2, insulin Tmax=18±8 min).

C3: Pharmacodynamic and Pharmacokinetic Results for the Insulin Solutions of Examples B2 and B10

| Example | Insulin | Compound | Polyanionic compound | Number of pigs |
|---|---|---|---|---|
| B2 | Lispro | — | — | 11 |
| B10 | Lispro | 1 | Polyanionic compound 1 | 11 |

The pharmacodynamic results obtained with the formulations described in examples B2 and B10 are presented in FIG. 3. According to the invention, the analysis of these curves shows that the formulation of example B10 comprising compound 1 and the polyanionic compound 1 as excipients at 20 mg/mL (curve plotted with the squares corresponding to example B10, glucose Tmin=33±13 min) makes it possible to obtain more rapid action than that obtained with the Humalog® commercial formulation of example B2 (curve plotted with the triangles corresponding to example B2, glucose Tmin=44±14 min).

The pharmacokinetic results obtained with the formulations described in examples B2 and B10 are presented in FIG. 4. According to the invention, the analysis of these curves shows that the formulation of example B10 comprising compound 1 and the polyanionic compound 1 as excipients at 20 mg/mL (curve plotted with the squares corresponding to example B10, insulin Tmax=15±9 min) induces more rapid absorption of the lispro insulin than that of the Humalog® commercial formulation of example B2 (curve plotted with the triangles corresponding to example B2, insulin Tmax=18±8 min).

C4: Pharmacodynamic and Pharmacokinetic Results for the Insulin Solutions of Examples B2 and B7

| Example | Insulin | Compound | Polyanionic compound | Number of pigs |
|---|---|---|---|---|
| B2 | Lispro | — | — | 12 |
| B7 | Lispro | 1 | — | 12 |

The pharmacodynamic results obtained with the formulations described in examples B2 and B7 are presented in FIG. 5. According to the invention, the analysis of these curves shows that the formulation of example B7 comprising compound 1 as excipient (curve plotted with the squares corresponding to example B7, glucose Tmin=41±16 min) includes more rapid onset of action than that obtained with the Humalog® commercial formulation of example B2 (curve plotted with the triangles corresponding to example B2, glucose Tmin=50±14 min).

The pharmacokinetic results obtained with the formulations described in examples B2 and B7 are presented in FIG. 6. The analysis of these curves shows that the formulation comprising compound 1 as excipient (curve plotted with the squares corresponding to example B2, insulin Tmax=21±10 min) does not induce more rapid absorption of the lispro insulin than that of the Humalog® commercial formulation of example B2 (curve plotted with the triangles corresponding to example B2 (insulin Tmax=20±9 min). Compound 1 alone is therefore insufficient to induce significant acceleration of the pharmacokinetics of lispro insulin.

C5: Pharmacodynamic and Pharmacokinetic Results for the Insulin Solutions of Examples B1 and B3

| Example | Insulin | Compound | Polyanionic compound | Number of pigs |
|---|---|---|---|---|
| B1 | Aspart | — | — | 11 |
| B3 | Human | — | — | 11 |

The pharmacodynamic results obtained with the formulations described in examples B1 and B3 are presented in FIG. 7. The analysis of these curves shows that the human insulin formulation of example B3 (curve plotted with the squares corresponding to example B3, glucose Tmin=61±31 min) does indeed have slower action than that of the aspart insulin commercial formulation of example B1 (curve plotted with the triangles corresponding to example B1, glucose Tmin=44±13 min).

The pharmacokinetic results obtained with the formulations described in examples B1 and B3 are presented in FIG. 8. The analysis of these curves shows that the human insulin formulation alone of example B3 (curve plotted with the squares corresponding to example B3, insulin Tmax=36±33 min) does indeed induce slower absorption than that of the aspart insulin commercial formulation (Novolog®) of example B1 (curve plotted with the triangles corresponding to example B1, insulin Tmax=28±13 min).

These results are in accordance with the literature results, with acceleration of the lowering of glycemia and of the absorption of insulin for a rapid insulin analog relative to a human insulin.

C6: Pharmacodynamic and Pharmacokinetic Results for the Insulin Solutions of Examples B1 and B39

| Example | Insulin | Compound | Polyanionic compound | Number of pigs |
|---|---|---|---|---|
| B1 | Aspart | — | — | 14 |
| B39 | Human | 1 | Citrate 9.3 mM | 5 |

The pharmacodynamic results obtained with the formulations described in examples B1 and B39 are presented in FIG. 9. The analysis of these curves shows that the formulation based on human insulin of example B39 comprising compound 1 and citrate at 9.3 mM as excipients (curve plotted with the squares corresponding to example B39, glucose Tmin=46±9 min) makes it possible to obtain similar action to that obtained with the aspart insulin commercial formulation (Novolog®) of example B1 (curve plotted with the triangles corresponding to example B1, glucose Tmin=53±24 min).

The pharmacokinetic results obtained with the formulations described in examples B1 and B39 are presented in FIG. 10. The analysis of these curves shows that the formulation of example B39 comprising compound 1 and citrate at 9.3 mM as excipients (curve plotted with the squares corresponding to example B39, insulin Tmax=20±7 min) induces insulin absorption similar to that obtained with the aspart insulin commercial formulation (Novolog®) of example B1 (curve plotted with the triangles corresponding to example B1, insulin Tmax=22±10 min).

Since the time parameters for the aspart insulin (Novolog®) between examples C5 and C6 are similar, it may be deduced by extrapolation that the formulation of example B39 induces acceleration of the lowering of glycemia and of the absorption of human insulin relative to the commercial formulation of human insulin (example B3).

C7: Pharmacodynamic and Pharmacokinetic Results for the Insulin Solutions of Examples B2 and B11

| Example | Insulin | Compound | Polyanionic compound | Number of pigs |
|---|---|---|---|---|
| B2 | Lispro | — | — | 26 |
| B11 | Lispro | 2 | Citrate 9.3 mM | 23 |

The pharmacodynamic results obtained with the formulations described in examples B2 and B11 are presented in FIG. 13. According to the invention, the analysis of these curves shows that the formulation of example B11 comprising compound 2 and citrate at 9.3 mM as excipients (curve plotted with the squares corresponding to example B11, glucose Tmin=32±10 min) makes it possible to obtain more rapid action than that obtained with the Humalog commercial formulation of example B2 (curve plotted with the triangles corresponding to example B2, glucose Tmin=41±21 min).

The pharmacokinetic results obtained with the formulations described in examples B2 and B11 are presented in FIG. 14. According to the invention, the analysis of these curves shows that the formulation of example B11 comprising compound 2 and citrate at 9.3 mM as excipients (curve plotted with the squares corresponding to example B11, insulin Tmax=13±5 min) induces more rapid absorption of the lispro insulin than that of the Humalog® commercial formulation of example B2 (curve plotted with the triangles corresponding to example B2, insulin Tmax=22±13 min).

C8: Pharmacodynamic and Pharmacokinetic Results for the Insulin Solutions of Examples B1 and B38

| Example | Insulin | Compound | Polyanionic compound | Number of pigs |
|---|---|---|---|---|
| B1 | Aspart | — | — | 37 |
| B38 | Human | 2 | Citrate 9.3 mM | 31 |

The pharmacodynamic results obtained with the formulations described in examples B1 and B38 are presented in FIG. 15. The analysis of these curves shows that the formulation based on human insulin of example B38 comprising compound 2 and citrate at 9.3 mM as excipients (curve plotted with the squares corresponding to example B102, glucose Tmin=47±30 min) makes it possible to obtain similar action to that obtained with the aspart insulin commercial formulation (Novolog®) of example B1 (curve plotted with the triangles corresponding to example B1, glucose Tmin=47±15 min).

The pharmacokinetic results obtained with the formulations described in examples B1 and B38 are presented in FIG. 16. The analysis of these curves shows that the formulation of example B38 comprising compound 2 and citrate at 9.3 mM as excipients (curve plotted with the squares corresponding to example B38, insulin Tmax=22±21 min) induces human insulin absorption similar to that obtained with the aspart insulin commercial formulation (Novolog®) of example B1 (curve plotted with the triangles corresponding to example B1, insulin Tmax=19±12 min).

Since the time parameters for the aspart insulin (Novolog®) between examples C5 and C8 are similar, it may be deduced by extrapolation that the formulation of example B38 induces acceleration of the lowering of glycemia and of the absorption of human insulin relative to the commercial formulation of human insulin (example B3).

C9: Pharmacodynamic and Pharmacokinetic Results for the Insulin Solutions of Examples B1 and B53

| Example | Insulin | Compound | Polyanionic compound | Number of pigs |
|---|---|---|---|---|
| B1 | Aspart | — | — | 12 |
| B53 | Human | Compound 8 | Citrate 9.3 mM | 8 |

The pharmacodynamic results obtained with the formulations described in examples B1 and B53 are presented in FIG. 17. The analysis of these curves shows that the formulation based on human insulin of example B53 comprising compound 8 and citrate at 9.3 mM as excipients (curve plotted with the squares corresponding to example B53, glucose Tmin=63±36 min) makes it possible to obtain action virtually as rapid as that obtained with the aspart insulin commercial formulation (Novolog®) of example B1 (curve plotted with the triangles corresponding to example B1, glucose Tmin=53±19 min).

The pharmacokinetic results obtained with the formulations described in examples B1 and B53 are presented in FIG. 18. The analysis of these curves shows that the formulation of example B53 comprising compound 8 and citrate at 9.3 mM as excipients (curve plotted with the squares corresponding to example B53, insulin Tmax=19±12 min) induces human insulin absorption similar to that obtained with the aspart insulin commercial formulation (Novolog®) of example B1 (curve plotted with the triangles corresponding to example B1, insulin Tmax=19±6 min).

Since the time parameters for the aspart insulin (Novolog®) between examples C5 and C9 are similar, it may be deduced by extrapolation that the formulation of example B53 induces acceleration of the lowering of glycemia and of the absorption of human insulin relative to the commercial formulation of human insulin (example B3).

D Circular Dichroism

D1: Association State of Lispro Insulin Evaluated by Circular Dichroism in the Presence of Compound 1

Circular dichroism makes it possible to study the secondary and quaternary structure of insulin. The insulin monomers are organized as dimers and as hexamers. The hexamer is the physically and chemically most stable form of insulin. Two hexameric forms exist, the R6 form and the T6 form. Lispro insulin has a strong CD signal at 251 nm characteristic of the R6 hexameric form (most stable form). Loss of the CD signal at 251 nm is linked to destabilization of the hexamer (and thus the first sign of transformation of the hexamer into dimer).

EDTA and the EDTA/citrate mixture completely destructure the R6 form of lispro insulin (FIG. 11). EDTA thus has a pronounced effect on the hexamer.

In contrast, citrate alone, compound 1 alone, and also the mixture compound 1/citrate and compound 1/polyanionic compound 1, have virtually no impact on the CD signal at 251 nm. These compounds therefore have virtually no impact on the R6 structure of the hexamer and, all the less so, on the hexameric structure.

D2: Association State of Human Insulin Evaluated by Circular Dichroism in the Presence of Compound 1

Circular dichroism makes it possible to study the secondary and quaternary structure of insulin. The insulin monomers are organized as dimers and as hexamers. The hexamer is the physically and chemically most stable form of insulin. The CD signal at 275 nm is characteristic of the hexameric form of insulin (hexamer signal at about −300°, signal for the dimer between −200° and −250°, and signal for the monomer below −200°. Loss of the CD signal at 275 nm is therefore characteristic of destabilization of the hexamer into dimers or monomers.

EDTA and the EDTA/citrate combination have a very pronounced impact on the hexameric structure of human insulin (total dissociation of the hexamer into dimers, FIG. 12). In contrast, citrate alone, compound 1 alone, the polyanionic compound 1 alone and also the compound 1/citrate and compound 1/polyanionic compound 1 combinations have no impact on the hexameric structure of human insulin. Unlike EDTA, the human insulin formulations comprising compound 1 and citrate or the polyanionic compound 1 do not show any dissociation of the human insulin hexamer.

D3: Association State of Lispro Insulin Evaluated by Circular Dichroism in the Presence of Compounds 1 to 11

Circular dichroism makes it possible to study the secondary and quaternary structure of insulin. The insulin monomers are organized as dimers and as hexamers. The hexamer is the physically and chemically most stable form of insulin. Two hexameric forms exist, the R6 form and the T6 form. Lispro insulin has a strong CD signal at 251 nm characteristic of the R6 hexameric form (most stable form). Loss of the CD signal at 251 nm is linked to destabilization of the hexamer (and thus the first sign of transformation of the hexamer into dimer). The results obtained are presented in FIG. 19. This figure describes on the x-axis:
- A: lispro insulin (100 IU/mL)
- B: lispro insulin+7.3 mg/mL of compound 2
- C: lispro insulin+7.3 mg/mL of compound 2+citrate at 9.3 mM
- D: lispro insulin+7.3 mg/mL of compound 1
- E: lispro insulin+7.3 mg/mL of compound 1+citrate at 9.3 mM
- F: lispro insulin+7.3 mg/mL of compound 3
- G: lispro insulin+7.3 mg/mL of compound 3+citrate at 9.3 mM
- H: lispro insulin+7.3 mg/mL of compound 4
- I: lispro insulin+7.3 mg/mL of compound 4+citrate at 9.3 mM
- J: lispro insulin+7.3 mg/mL of compound 5
- K: lispro insulin+7.3 mg/mL of compound 5+citrate at 9.3 mM
- L: lispro insulin+7.3 mg/mL of compound 6
- M: lispro insulin+7.3 mg/mL of compound 6+citrate at 9.3 mM
- N: lispro insulin+7.3 mg/mL of compound 7
- O: lispro insulin+7.3 mg/mL of compound 7+citrate at 9.3 mM
- P: lispro insulin+7.3 mg/mL of compound 8
- Q: lispro insulin+7.3 mg/mL of compound 8+citrate at 9.3 mM
- R: lispro insulin+7.3 mg/mL of compound 9
- S: lispro insulin+7.3 mg/mL of compound 9+citrate at 9.3 mM
- T: lispro insulin+7.3 mg/mL of compound 10
- U: lispro insulin+7.3 mg/mL of compound 10+citrate at 9.3 mM
- V: lispro insulin+7.3 mg/mL of compound 11
- W: lispro insulin+7.3 mg/mL of compound 11+citrate at 9.3 mM and on the y-axis the circular dichroism signal at 251 nm (deg·cm$^2$·dmol$^{-1}$).

Compounds 1 to 11 alone and also compounds 1 to 11 in combination with citrate have no impact on the CD signal at 251 nm for lispro insulin. Compounds 1 to 11 therefore have no impact on the R6 structure of the hexamer and, all the less so, on the hexameric structure of lispro insulin.

D4: Association State of Human Insulin Evaluated by Circular Dichroism in the Presence of Compounds 1 to 11

Circular dichroism makes it possible to study the secondary and quaternary structure of insulin. The insulin monomers are organized as dimers and as hexamers. The hexamer is the physically and chemically most stable form of insulin. The CD signal at 275 nm is characteristic of the hexameric form of insulin (hexamer signal at about −300°, signal for the dimer between −200° and −250°, and signal for the monomer below −200°). Loss of the CD signal at 275 nm is therefore characteristic of destabilization of the hexamer into dimers or monomers. The results obtained are presented in FIG. 20. This figure describes on the x-axis:
- A: human insulin (100 IU/mL)
- B: human insulin+7.3 mg/mL of compound 2
- C: human insulin+7.3 mg/mL of compound 2+citrate at 9.3 mM
- D: human insulin+7.3 mg/mL of compound 1
- E: human insulin+7.3 mg/mL of compound 1+citrate at 9.3 mM
- F: human insulin+7.3 mg/mL of compound 3
- G: human insulin+7.3 mg/mL of compound 3+citrate at 9.3 mM
- H: human insulin+7.3 mg/mL of compound 4
- I: human insulin+7.3 mg/mL of compound 4+citrate at 9.3 mM
- J: human insulin+7.3 mg/mL of compound 5
- K: human insulin+7.3 mg/mL of compound 5+citrate at 9.3 mM
- L: human insulin+7.3 mg/mL of compound 6
- M: human insulin+7.3 mg/mL of compound 6+citrate at 9.3 mM
- N: human insulin+7.3 mg/mL of compound 7
- O: human insulin+7.3 mg/mL of compound 7+citrate at 9.3 mM
- P: human insulin+7.3 mg/mL of compound 8
- Q: human insulin+7.3 mg/mL of compound 8+citrate at 9.3 mM
- R: human insulin+7.3 mg/mL of compound 9
- S: human insulin+7.3 mg/mL of compound 9+citrate at 9.3 mM
- T: human insulin+7.3 mg/mL of compound 10
- U: human insulin+7.3 mg/mL of compound 10+citrate at 9.3 mM
- V: human insulin+7.3 mg/mL of compound 11
- W: human insulin+7.3 mg/mL of compound 11+citrate at 9.3 mM and on the y-axis the circular dichroism signal at 275 nm (deg·cm$^2$·dmol$^{-1}$).

Compounds 1 to 11 alone and also compounds 1 to 11 in combination with citrate have no impact on the CD signal at 275 nm for human insulin. Compounds 1 to 11 therefore have no impact on the hexameric structure of human insulin.

E Dissolution of Human Insulin and Insulin Analogs at the Isoelectric Point

E1. Dissolution of Human Insulin at its Isoelectric Point

Human insulin has an isoelectric point at 5.3. At this pH of 5.3, human insulin precipitates. A test demonstrating the formation of a complex of human insulin with the various compounds is performed at the isoelectric point. If an interaction exists, it is possible to dissolve the insulin at its isoelectric point.

A 200 IU/mL human insulin solution is prepared. Solutions of compounds at different concentrations (8, 30 or 100 mg/mL) in water are prepared. An equivolume (50/50) mixture between the human insulin solution and the solution of compound is prepared to lead to a solution containing 100

IU/mL of human insulin and the desired concentration of compound (4, 15 or 50 mg/mL). The pH of the various solutions is adjusted to pH 5.3 by adding 200 mM acetic acid.

The appearance of the solution is documented. If the solution is turbid, the compound at the test concentration does not allow dissolution of the human insulin. If the solution is translucent, the compound allows dissolution of the human insulin at the test concentration. In this way, the concentration of compound required to dissolve the human insulin at its isoelectric point may be determined. The lower this concentration, the greater the affinity of the compound for human insulin.

The results obtained are presented in Table 3. The results show that the compounds and the polysaccharides do not have the same properties in terms of human insulin dissolution.

TABLE 3

| Compounds (examples) or Polysaccharides (counterexamples) | Dissolution of human insulin at 100 IU/mL with the compound at 4 mg/mL | Dissolution of human insulin at 100 IU/mL with the compound at 15 mg/mL | Dissolution of human insulin at 100 IU/mL with the compound at 50 mg/mL |
|---|---|---|---|
| Counterexamples | | | |
| Polysaccharide 1 | Yes | Yes | Yes |
| Polysaccharide 4 | Yes | Yes | Yes |
| Polysaccharide 3 | Yes | Yes | Yes |
| Polysaccharide 2 | Yes | Yes | Yes |
| Polysaccharide 5 | Yes | Yes | Yes |
| Examples | | | |
| Compound 1 | No | No | Yes |
| Compound 2 | No | No | Yes |
| Compound 3 | No | No | Yes |
| Compound 4 | No | No | Yes |
| Compound 6 | No | No | Yes |
| Compound 8 | No | No | Yes |
| Compound 9 | No | No | Yes |
| Compound 10 | No | No | Yes |

E2. Dissolution of Lispro Insulin at its Isoelectric Point

Lispro insulin has an isoelectric point at 5.3. At this pH, lispro insulin precipitates. A test demonstrating the formation of a complex of lispro insulin with the various compounds is performed at the isoelectric point. If an interaction exists, it is possible to dissolve the lispro insulin at its isoelectric point.

The commercial formulation of lispro insulin (Humalog®) is dialyzed against 1 mM $PO_4$ buffer (pH 7). After dialysis, the lispro insulin concentration is about 90 IU/mL. The lyophilized compound is weighed out and dissolved in the lispro insulin solution to lead to formulations containing lispro insulin at 90 IU/mL and the compound at the desired concentrations (4, 15 or 50 mg/mL). The pH of the various solutions is adjusted to pH 5.3 by adding 200 mM acetic acid.

The appearance of the solution is documented. If the solution is turbid, the compound at the test concentration does not allow dissolution of the lispro insulin. If the solution is translucent, the compound allows dissolution of the lispro insulin at the test concentration. In this way, the concentration of compound required to dissolve the lispro insulin at its isoelectric point may be determined. The lower this concentration, the greater the affinity of the compound for the lispro insulin.

The results obtained are presented in Table 4. The results show that the compounds and the polysaccharides do not have the same properties in terms of lispro insulin dissolution.

TABLE 4

| Compounds (examples) or Polysaccharides (counterexamples) | Dissolution of lispro insulin at 90 IU/mL with the compound at 4 mg/mL | Dissolution of lispro insulin at 90 IU/mL with the compound at 15 mg/mL | Dissolution of lispro insulin at 90 IU/mL with the compound at 50 mg/mL |
|---|---|---|---|
| Counterexamples | | | |
| Polysaccharide 1 | Yes | Yes | Yes |
| Polysaccharide 3 | Yes | Yes | Yes |
| Polysaccharide 2 | Yes | Yes | Yes |
| Examples | | | |
| Compound 1 | No | No | Yes |
| Compound 2 | No | No | Yes |
| Compound 3 | No | No | Yes |

F Interaction with Albumin

F1: In order to determine the interactions between the various polysaccharides or compounds and a model protein such as albumin, a Centricon test (membrane with a cut-off threshold of 50 kDa) was performed. A solution of polysaccharide or of compound at 7.3 mg/mL was diluted three-fold in a solution of BSA (bovine serum albumin) at 20 mg/mL in PBS (concentration in the mixture: 2.43 mg/mL of polysaccharide or of compound, 13.3 mg/mL of albumin and about 100 mM of salts).

This mixture was centrifuged on a Centricon to make about half the volume pass through the membrane. The albumin is quantitatively retained on the Centricon membrane. The polysaccharides and compounds analyzed alone pass in large majority through the membrane (for the polysaccharides having the largest molar masses, about 20% of the polysaccharide is retained).

After centrifugation, the polysaccharide or compound is assayed by UV in the filtrate. The percentage of polysaccharide or compound bound to the albumin is calculated via the following equation:

(1−[polysaccharide or compound in the filtrate in the presence of albumin]/[polysaccharide or compound in the filtrate in the absence of albumin])*100

The results obtained are presented in Table 5. It is very clearly observed that the polysaccharides of molar mass 5-15 kDa are strongly retained by the albumin in this test. In contrast, the compounds of the invention of lower molar mass are markedly less retained by the albumin in this test.

TABLE 5

| Polysaccharide or Compound | % Polysaccharide or % Compound bound to BSA |
|---|---|
| Counterexamples | |
| Polysaccharide 4 | 97% |
| Polysaccharide 1 | 95% |
| Polysaccharide 3 | 77% |
| Polysaccharide 5 | 86% |
| Polysaccharide 2 | 82% |

TABLE 5-continued

| Polysaccharide or Compound | % Polysaccharide or % Compound bound to BSA |
|---|---|
| Examples | |
| Compound 2 | 21% |
| Compound 1 | 20% |
| Compound 3 | 27% |
| Compound 4 | 24% |
| Compound 5 | 24% |
| Compound 6 | 26% |
| Compound 7 | 27% |
| Compound 8 | 27% |
| Compound 9 | 43% |
| Compound 11 | 35% |

The invention claimed is:

1. A rapid acting insulin lispro pharmaceutical composition suitable for injection and having a pH of 7.4±0.4, comprising:
 an insulin lispro in hexameric form; wherein the insulin has a concentration between 100 to 200 IU/mL;
 a polyanionic compound in a concentration between 10 and 30 mM, wherein the polyanionic compound is citric acid or the $Na^+$, $K^+$, $Ca^{2+}$ or $Mg^{2+}$ salt thereof;
 a preservative;
 a tonicity agent;
 the insulin pharmaceutical composition having a circular dichroism signal at 251 nm at or below −300 deg $cm^2 dmol^{-1}$.

2. The rapid acting insulin lispro pharmaceutical composition of claim 1, wherein the pharmaceutical composition does not include EDTA.

3. The rapid acting insulin lispro pharmaceutical composition of claim 1, wherein the tonicity agent is selected from the group consisting of glycerol, sodium chloride (NaCl), mannitol and glycine.

4. The rapid acting insulin lispro pharmaceutical composition of claim 3, wherein the tonicity agent is sodium chloride.

5. The rapid acting insulin lispro pharmaceutical composition of claim 4, further comprising zinc salts.

6. The rapid acting insulin lispro pharmaceutical composition of claim 1, wherein the preservative is m-cresol.

7. The rapid acting insulin lispro pharmaceutical composition of claim 5, further comprising a surfactant.

* * * * *